(12) United States Patent
Marnett et al.

(10) Patent No.: US 8,168,656 B2
(45) Date of Patent: May 1, 2012

(54) INDOLEACETIC ACID AND INDENACETIC ACID DERIVATIVES AS THERAPEUTIC AGENTS WITH REDUCED GASTROINTESTINAL TOXICITY

(75) Inventors: Lawrence J. Marnett, Nashville, TN (US); Jeffery J. Prusakiewicz, Nashville, TN (US); Andrew S. Felts, Nashville, TN (US); Chuan Ji, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/319,262

(22) Filed: Jan. 5, 2009

(65) Prior Publication Data

US 2009/0118290 A1 May 7, 2009

(51) Int. Cl.
*A61K 31/47* (2006.01)
*C07D 453/02* (2006.01)
(52) U.S. Cl. ........................ 514/311; 546/134
(58) Field of Classification Search .................. 514/305, 514/311; 546/134
See application file for complete search history.

(56) References Cited

U.S. PATENT DOCUMENTS

| | | |
|---|---|---|
| 3,161,654 A | 12/1964 | Shen |
| 3,196,162 A | 7/1965 | Lewis et al. |
| 3,285,908 A | 11/1966 | Shen |
| 3,336,194 A | 8/1967 | Shen |
| 3,470,203 A | 9/1969 | Gal et al. |
| 3,654,349 A | 4/1972 | Shen et al. |
| 3,725,548 A | 4/1973 | Shen et al. |
| 4,229,447 A | 10/1980 | Porter |
| 4,412,994 A | 11/1983 | Sloan et al. |
| 4,851,426 A | 7/1989 | Ladkani et al. |
| 5,016,652 A | 5/1991 | Rose et al. |
| 5,032,588 A | 7/1991 | Brooks et al. |
| 5,093,356 A | 3/1992 | Girard et al. |
| 5,360,925 A | 11/1994 | Chabrier de Lassauniere et al. |
| 5,436,265 A | 7/1995 | Black et al. |
| 5,475,021 A | 12/1995 | Marnett et al. |
| 5,504,086 A | 4/1996 | Ellinwood, Jr. et al. |
| 5,510,368 A | 4/1996 | Lau et al. |
| 5,607,966 A | 3/1997 | Hellberg et al. |
| 5,681,964 A | 10/1997 | Ashton et al. |
| 5,811,425 A | 9/1998 | Woods et al. |
| 5,811,438 A | 9/1998 | Hellberg et al. |
| 5,861,419 A | 1/1999 | Dube et al. |
| 5,922,742 A | 7/1999 | Black et al. |
| 5,965,619 A | 10/1999 | Pamukcu et al. |
| 5,973,191 A | 10/1999 | Marnett et al. |
| 6,045,773 A | 4/2000 | Isakson et al. |
| 6,048,850 A | 4/2000 | Young et al. |
| 6,207,700 B1 | 3/2001 | Kalgutkar et al. |
| 6,277,878 B1 | 8/2001 | Nakao et al. |
| 6,284,918 B1 | 9/2001 | Marnett et al. |
| 6,306,890 B1 | 10/2001 | Kalgutkar et al. |
| 6,399,647 B2 | 6/2002 | Kalgutkar et al. |
| 6,762,182 B1 | 7/2004 | Kalgutkar et al. |
| 6,933,316 B2 | 8/2005 | Hsieh et al. |
| 7,491,744 B2 | 2/2009 | Marnett et al. |
| 2001/0034361 A1 | 10/2001 | Kalgutkar et al. |
| 2003/0195244 A1 | 10/2003 | Hsieh et al. |
| 2005/0002859 A1 | 1/2005 | Marnett et al. |
| 2005/0250839 A1 | 11/2005 | Marnett et al. |
| 2007/0292352 A1 | 12/2007 | Marnett et al. |

FOREIGN PATENT DOCUMENTS

| | | |
|---|---|---|
| CN | 1337851 A | 2/2002 |
| DE | 2735537 | 2/1979 |
| DE | 2926472 | 1/1981 |
| DE | 3145465 | 5/1983 |
| DE | 3235850 | 8/1983 |
| DE | 3206885 | 9/1983 |
| DE | 10163426 | 7/2003 |
| EP | 0051278 | 5/1982 |
| EP | 0080271 | 6/1983 |
| EP | 0144845 | 6/1985 |
| EP | 0327766 | 8/1989 |
| EP | 335164 | 10/1989 |
| EP | 335545 | 10/1989 |
| EP | 342682 | 11/1989 |
| EP | 1148783 | 6/2006 |
| ES | 432545 | 11/1976 |
| FR | 2392008 | 12/1978 |
| JP | 54090174 | 7/1979 |
| JP | 58201763 | 11/1983 |
| JP | 59161358 | 9/1984 |
| JP | 60152462 | 8/1985 |
| JP | A-60-214768 | 10/1985 |
| JP | 61060649 | 3/1986 |
| JP | 63196598 | 8/1988 |
| JP | 63275593 | 11/1988 |
| NL | 8105139 | 6/1982 |
| WO | WO 95/04030 | 2/1995 |
| WO | WO 95/20567 | 8/1995 |

(Continued)

OTHER PUBLICATIONS

Bahner et al., Anticancer compounds. Further analogs of 1-(4-Dimethulaminobenzylidene) indene. *Journal of Medicinal Chemistry*. vol. 16, No. 4 pp. 421-425 (1973).

Notice of Allowance corresponding to U.S. Appl. No. 11/114,921 dated Oct. 15, 2008.

Notification of Transmittal of the International Search Report and the Written Opinion of the International Searching Authority, or the Declaration corresponding to International Application No. PCT/US05/14328 dated Jan. 31, 2007.

(Continued)

Primary Examiner — Taofiq A Solola
(74) Attorney, Agent, or Firm — Jenkins, Wilson, Taylor & Hunt, P.A.

(57) ABSTRACT

The presently disclosed subject matter provides derivatives of non-steroidal anti-inflammatory drugs (NSAIDs) that are characterized by substantially reduced cyclooxygenase inhibiting activity, yet retain the ability to interact with and modulate the activities of other polypeptides such as the class of peroxisome proliferators-activated receptors (PPARs) and γ-secretase. Also provided are methods of using the derivatives to treat pathological disorders.

10 Claims, 10 Drawing Sheets
(1 of 10 Drawing Sheet(s) Filed in Color)

FOREIGN PATENT DOCUMENTS

| | | |
|---|---|---|
| WO | WO 95/22524 | 8/1995 |
| WO | WO 98/32718 | 7/1998 |
| WO | WO 00/40087 | 7/2000 |
| WO | WO 00/40088 | 7/2000 |
| WO | WO 01/15686 | 3/2001 |
| WO | WO 02/08188 | 1/2002 |
| WO | WO 02/20478 | 3/2002 |
| WO | WO02/028831 | 4/2002 |
| WO | WO02/060438 | 8/2002 |
| WO | WO 2004/020409 | 3/2004 |
| WO | WO 2005/002293 | 1/2005 |
| WO | WO 2005/112921 | 12/2005 |

OTHER PUBLICATIONS

Official Action corresponding to U.S. Appl. No. 11/114,921 dated Aug. 17, 2007.
Official Action corresponding to U.S. Appl. No. 11/114,921 dated Mar. 6, 2008.
Official Action corresponding to U.S. Appl. No. 11/114,921 dated Jun. 24, 2008.
Touhey et al., Structure-activity relationship of indomethacin analogues for MRP-1, COX-1 and COX-2 inhibition identification of novel chemotherapeutic drug resistance modulators. *European Journal of Cancer*. vol. 38, No. 12 pp. 1661-1670 (2002).
Allison et al., Gastrointestinal Damage Asssociated with the Use of Nonsteroidal Antiinflammatory Drug. *The New England Journal of Medicine*. vol. 327, No. 11 pp. 749-754 (1992).
Archibald et al., Synthesis and Hypotensive Activity of Benzamidopiperidylethylindoles. *Journal of Medicinal Chemistry*. vol. 14, No. 11 pp. 1054-1059 (1971).
Barasoain et al., Immunosuppressive Effects of Some Organic Compounds with Anti-Inflammatory Activity. *Proceedings of the International Congress of Chemotherapy*. vol. 8 pp. 21-26 (1976) (Abstract).
Barasoain et al., Indomethacin Esters Acting as Anti-Inflammatory and Immunosuppressive Drugs. *International Journal of Clinical Pharmacology Biopharm*. vol. 16, No. 5 pp. 235-239 (1978) (Abstract).
Black et al., From Indomethacin to a Selective COX-2 Inhibitor: Development of Indolalkanoic Acids as Potent and Selective COX-2 Inhibitors. *Bioorganic & Medicinal Chemistry Letters*. vol. 6, No. 6 pp. 725-730 (1996).
Boltze et al., Chemical Structure and Antiinflammatory Activity in the Group of Substituted Indole-3-Acetic Acids. *Arzneim-Forsch*. vol. 30, No. 8A pp. 1314-1325 (1980) (English Abstract).
Bonina et al., In Vitro and In Vivo Evaluation of Polyoxyethylene Indomethacin Esters as Dermal Prodrugs. *Journal of Controlled Release*. vol. 34, No. 3 pp. 223-232 (1995) (Abstract).
Bonina et al., Pharmacokinetic and pharmacodynamic profile of triethylene glycol indomethacin ester as a new oral prodrug. *Journal of Controlled Release*. vol. 41, No. 3 pp. 187-193 (1996) (Abstract).
Chan et al., Pharmacology of a Selective Cyclooxygenase-2 Inhibitor, L-745, 337: A Novel Nonsteroidal Anti-inflammatory Agent with an Ulcerogenic Sparing Effect in Rat and Nonhuman Primate Stomach. *The Journal of Pharmacology and Experimental Therapeutics*. vol. 274, No. 3 pp. 1531-1537 (1995).
Chinery et al., Prostaglandin $J_2$ and 15-Deoxy-$\Delta^{12,14}$-prostaglandin $J_2$ Induce Proliferation of Cyclooxygenase-depleted Colorectal Cancer Cells. *Cancer Research*. vol. 59 pp. 2739-2746 (1999).
Correspondence from foreign patent attorney regarding Notice of Allowance corresponding to Israeli Patent Application No. 144,126 dated Aug. 9, 2007.
Correspondence from foreign patent attorney regarding Official Action corresponding to Chinese Patent Application No. 00814912.7 dated Mar. 11, 2004.
Correspondence from foreign patent attorney regarding Official Action corresponding to Chinese Patent Application No. 00814912.7 dated Aug. 11, 2004.
Correspondence from foreign patent attorney regarding Official Action corresponding to Chinese Patent Application No. 00814912.7 dated May 10, 2006.
Correspondence from foreign patent attorney regarding Official Action corresponding to Chinese Patent Application No. 99816452.6 dated Sep. 30, 2003.
Correspondence from foreign patent attorney regarding Official Action corresponding to Chinese Patent Application No. 99816452.6 dated Jul. 29, 2004.
Correspondence from foreign patent attorney regarding Official Action corresponding to Chinese Patent Application No. 99816452.6 dated Jan. 26, 2005.
Correspondence from foreign patent attorney regarding Official Action corresponding to Israeli Patent Application No. 144,126 dated Sep. 14, 2005.
Davaran et al., Acrylic type polymers containing ibuprofen and indomethacin with disfunctional spacer group: synthesis and hydrolysis. *Journal of Controlled Release*. vol. 47 pp. 41-49 (1997).
De Caprariis et al., Synthesis and Pharmacological Evaluation of Oligoethylene Ester Derivatives as Indomethacin Oral Prodrugs. *Journal of Pharmaceutical Science*. vol. 83, No. 11 pp. 1578-1581 (1994) (Abstract).
Decision of Granting Patent Right for Invention corresponding to Chinese Patent Application No. 00814912.7 dated May 30, 2008.
Devane et al., Isolation and Structure of a Brain Constituent That Binds to the Cannabinoid Receptor. *Science*. vol. 258 pp. 1946-1949 (1992).
Dewitt et al., Primary structure of prostaglandin G/H synthase from sheep vesicular gland determined from the complementary DNA sequence. *PNAS. USA* vol. 85 pp. 1412-1416 (1988).
Diago-Meseguer et al., A New Reagent for Activating Carboxyl Groups; Preparation and Reactions of N,N-Bis[2-oxo-3-oxazolidinyl]phosphorodiamidic Chloride. *Communication*. pp. 547-551 (1980).
Downing et al., Enzyme Inhibition by Acetylenic Compounds. *Biochemical and Biophysical Research Communications*. vol. 40, No. 1 pp. 218-223 (1970).
Downing et al., Structural Requirements of Acetylenic Fatty Acids for Inhibition of Soybean Lipoxygenase and Prostaglandin Synthetase. *Biochimica et Biophysica Acta*. vol. 280 pp. 343-347 (1972).
Fan et al., Membrane effects of antiinflammatory agents. 1. Interaction of sulindace and its metabolites with phospholipid membrane, a magnetic resonance study. *Journal of Medicinal Chemistry*. vol. 24, No. 10 pp. 1197-1202 (1981). [Abstract].
Fisnerova et al., Esters of 1-(p-chlorobenzoyl)-5-methoxy-2-methyl-3-indolylacetic Acid. *Heterocycles*. vol. 95 p. 667 (1981).
Fisnerova et al., Pharmacologically Interesting Indomethacin Derivatives. *Heterocycles*. vol. 88 p. 373 (1978).
Flynn et al., Nonsteroidal Anti-inflammatory Drug Hydroxamic Acids. Dual Inhibitors of Both Cyclooxygenase and 5-lipoxygenase. *Journal of Medicinal Chemistry*. vol. 33, No. 8 pp. 2070-2072 (1990).
Futaki et al., NS-398, A new anti-inflammatory agent, selectivity inhibits prostaglandin G/H synthase/cyclooxygenase (COX-2) activity in vitro. *Prostaglandins*. vol. 47 pp. 55-59 (1994).
Gan et al., Anti-inflammatory and Safety Profile of DuP 697, a Novel Orally Effective Prostaglandin Synthesis Inhibitor. *The Journal of Pharmacology and Experimental Therapeutics*. vol. 254, No. 1 pp. 180-187 (1990).
Grant of Canadian Patent Application No. 2,382,296 dated Nov. 17, 2009.
Graedon et al., Pills Promise Relief Without Ulcers. *The News and Observer*. p. 8D (Sep. 13, 1998) (Newspaper article).
Heasley et al., Induction of Cytosolic Phospholipase $A_2$ by Oncogenic Ras in Human Non-small Cell Lung Cancer. *The Journal of Biological Chemistry*. vol. 272, No. 23, pp. 14501-14504 (1997).
Hla et al., Human cyclooxygenase-2 cDNA. *PNAS USA*. vol. 89 pp. 7384-7388 (1992).
Hong et al., Relationship of Archidonic Acid Metabolizing Enzyme Expresson in Epithelial Cancer Cell Lines to the Growth Effect of Selective Biochemical Inhibitors. *Cancer Research*. vol. 59 pp. 2223-2228 (1999).
Hwang et al., Expression of Cyclooxygenase-1 and Cyclooxygenase-2 in Human Breast Cancer. Journal of the National Cancer Institute. vol. 90, No. 6 pp. 455-460 (1998).

Issued Patent corresponding to Israeli Patent No. 144126 dated Apr. 21, 2008.

Kalgutkar et al., Amide Derivatives of Meclofenamic Acid as Selective Cyclooxygenase-2 Inhibitors. *Bioorganic and Medicinal Chemistry Letters*. vol. 12 pp. 521-524 (2002).

Kalgutkar et al., Aspirin-Like Molecules that Covalently Inactivate Cyclooxygenase-2. *Science*. vol. 280 pp. 1268-1270 (1998).

Kalgutkar et al., Biochemically based design of cyclooxygenase-2 (COX-2) inhibitors: Facile conversion of nonsteroidal antiinflammatory drugs to potent and highly selective COX-2 inhibitors. *PNAS*. vol. 97, No. 2 pp. 925-930 (2000).

Kappe et al., *Non-steroidal Antiinflammatory Agents. V. Basic Esters of Indomethacin*. Journal für Praktische Chemie. vol. 332, No. 4 pp. 475-478 (1990) (Abstract).

Katori et al., Induction of Prostaglandin H Synthase-2 in Rat Carrageenin-induced Pleurisy and Effect of a Selective Cox-2 Inhibitor. *Advances in Prostaglandin Thromboxane and Leukotriene Research*. vol. 23 pp. 345-347 (1995).

Kennedy et al., Cloning and Expression of Rat Prostaglandin Endoperoxide Synthase (Cyclooxygenase)-2 cDNA. *Biochemical and Biophysical Research Communications*. vol. 197, No. 2 pp. 494-500 (1993).

Khanna et al., 1,2-Diarylimidazoles as Potent Cyclooxygenase-2 Selective, and Orally Active Antiinflammatory Agents. *Journal of Medicinal Chemistry*. vol. 40, No. 11 pp. 1634-1647 (1997).

Khanna et al., 1,2-Diarylpyrroles as Potent, and Selective Inhibitors of Cyclooxygenase-2. *Journal of Medicinal Chemistry*. vol. 40, No. 11 pp. 1619-1633 (1997).

Kolasa et al., Nonsteroidal Anti-Inflammatory Drugs as Scaffolds for the Design of 5-Lipoxygenase Inhibitors. *Journal of Medicinal Chemistry*. vol. 40 pp. 819-924 (1997).

Kozak et al., Enantiospecific, Selective Cyclooxygenase-2 Inhibitors. Bioorganic & Medicinal Chemistry Letters. vol. 12 pp. 1315-1318 (2002).

Kujubu et al., TIS10, a Phorbol Ester Tumor Promoter-inducible mRNA from Swiss 3T3 Cells, Encodes a Novel Prostaglandin Synthase/Cyclooxgenase Homologue. *The Journal of Biological Chemistry*. vol. 266, No. 20 pp. 12866-12872 (1991).

Kumar, J.S.D., et al., Synthesis of[11C]-TMI: A potential PET tracer for imaging COX-2 expression. Abstracts of Papers, 228th ACS National Meeting; Philadelphia, PA, United States, Aug. 22-26, 2004 (Abstract).

Kwapiszewski et al., Synthesis of N-[1-(p-chlorobenzoyl)-5-methoxy-2-methyl-3-indoleacetyl] Amino Acids and their Esters. *Acta. Pol. Pharm*. vol. 39, No. 5-6 pp. 327-336 (1982) (Abstract).

Lee et al., Selective Expression of Mitogen-inducible Cyclooxygenase in Macrophages Stimulated with Lipopolysaccharide. *The Journal of Biological Chemistry*. vol. 267 pp. 25934-25938 (1992).

Li et al., 1,2-Diarylcyclopentenes as Selective Cyclooxygenase-2 Inhibitors and Orally Active Anti-inflammatory Agents. *Journal of Medicinal Chemistry*. vol. 38, No. 22 pp. 4570-4578 (1995).

Li et al., Cyclooxygenase-2 Inhibitors. Synthesis and Pharmacological Activities of 5-Methanesulfonamido-1-indanone Derivatives. *Journal of Medicinal Chemistry*. vol. 38, No. 25 pp. 4897-4905 (1995).

Li et al., Novel Terphenyls as Selective Cyclooxygenase-2 Inhibitors and Orally Active Anti-inflammatory Agents. *Journal of Medicinal Chemistry*. vol. 39, No. 9 pp. 1846-1856 (1996).

Linari et al., Substituted Anilides of 1-(p-Chlorobenzoyl)-5-methoxy-2-methyl-indole-3-acetic Acid. *Arzneim-Foprsch*. (Drug Research) vol. 23, No. 1 pp. 89-91 (1973).

Luong et al., The Structure of Human Cyclooxygenase-2: Conservation and Flexibility of the NSAID Binding Site. *Nature Structural Biology*. vol. 3 pp. 927-933 (1996).

Makovec et al., Pharmacokinetics and metabolism of[14C]-proglumetacin after oral administration in the rat. *Arzneim-Forsch*. vol. 37, No. 7 pp. 806-813 (1987) (Abstract).

Marnett et al., Mechanism of the Stimulation of Prostaglandin H Synthase and Prostacyclin Synthase by the Antithromotic and Antimetastatic Agent, Nafazatrom. *Molecular Pharmacology*. vol. 26 pp. 328-335 (1984).

Masferrer et al., Selective inhibition of inducible cyclooxygenase 2 in vivo is antiinflammatory and nonulcerogenic. *PNAS USA*. vol. 91 pp. 3228-3232 (1994).

Mclean et al., Synthesis and pharmacological evaluation of congugates of prednisolone and non-steroidal anti-inflammatory agents. *Steroids*. vol. 54, No. 4 pp. 421-439 (1989) (Abstract).

McMurry, Carboxylic Acid Derivatives. *Organic Chemistry*. pp. 742-745 (1988).

Meade et al., Differential Inhibition of Prostaglandin Endoperoxide Synthase (Cyclooxygenase) Isozymes by Aspirin and Other Nonsteroidal Anti-inflammatory Drugs. *The Journal of Biological Chemistry*. vol. 238, No. 9 pp. 6610-6614 (1993).

Mulders, Indole Acid Amides. *Heterocyclic Compounds*. vol. 62 pp. 16198-16199 (1965).

Nakamura et al., Studies on Antiinflammatory Agents II. Synthesis and Pharmacological Properties of 2'-(Phenylthio)methanesulfonanilides and Related Derivatives. *Chemical and Pharmaceutical Bulletin*. vol. 41, No. 5 pp. 894-906 (1993).

Notice of Allowance corresponding to Canadian Patent Application No. 2,358,289 dated Mar. 16, 2009.

Notice of Allowance corresponding to Canadian Patent Application No. 2,382,296 dated Feb. 3, 2009.

Notification Concerning Transmittal of International Preliminary Report on Patentability (Chapter I of the Patent Cooperation Treaty) corresponding to International Application No. PCT/US2004/020455 dated Jan. 12, 2006.

Notification Concerning Transmittal of International Preliminary Report on Patentability (Chapter I of the Patent Cooperation Treaty) corresponding to International Application No. PCT/US2005/014328 dated Mar. 15, 2007.

Notification Concerning Transmittal of International Preliminary Report on Patentability (Chapter I of the Patent Cooperation Treaty) corresponding to International Application No. PCT/US2007/014315 dated Jan. 8, 2009.

Notification of Transmittal of the International Preliminary Examination Report corresponding to International Application No. PCT/US00/23153 dated Apr. 13, 2001.

Notification of Transmittal of the International Preliminary Examination Report corresponding to International Application No. PCT/US99/30219 dated Dec. 5, 2000.

Notification of Transmittal of the International Preliminary Examination Report corresponding to International Application No. PCT/US99/30220 dated Dec. 7, 2000.

Notification of Transmittal of the International Search Report and the Written Opinion of the International Searching Authority, or the Declaration corresponding to International Application No. PCT/US04/20455 dated Feb. 22, 2005.

Notification of Transmittal of the International Search Report and the Written Opinion of the International Searching Authority, or the Declaration corresponding to International Application No. PCT/US07/14315 dated Aug. 14, 2008.

Notification of Transmittal of the International Search Report or the Declaration corresponding to International Application No. PCT/US99/30219 dated Apr. 5, 2000.

Notification of Transmittal of the International Search Report or the Declaration corresponding to International Application No. PCT/US99/30220 dated Apr. 4, 2000.

Notification of Transmittal of the International Search Report or the Declaration corresponding to International Application No. PCT/US00/23153 dated Oct. 26, 2000.

Odenwaller et al., Preparation and Proteolytic Cleavage of Apoprostaglandin Endoperoxide Synthase. *Methods in Enzymology*. vol. 187 pp. 479-485 (1990).

Official Action corresponding to Canadian Patent Application No. 2,358,241 dated Aug. 28, 2008.

Official Action corresponding to Canadian Patent Application No. 2,358,289 dated Apr. 15, 2008.

Official Action corresponding to Canadian Patent Application No. 2,358,289 dated Sep. 2, 2009.

Official Action corresponding to Canadian Patent Application No. 2,382,296 dated Sep. 17, 2007.

Official Action corresponding to Canadian Patent Application No. 2,382,296 dated Apr. 1, 2008.
Official Action corresponding to Chinese Patent Application No. 200580021387.8 dated Oct. 9, 2009.
Official Action corresponding to European Patent Application No. 99 967 417.9-1521 dated Apr. 6, 2004.
Official Action corresponding to European Patent Application No. 99 967 417.9-1521 dated Feb. 11, 2005.
Official Action corresponding to European Patent Application No. 99 967 417.9-1521 dated Nov. 8, 2005.
Official Action corresponding to European Patent Application No. 99 967 416.1-2107 dated Aug. 31, 2005.
Official Action corresponding to U.S. Appl. No. 10/877,303 dated Jul. 24, 2007.
Official Action corresponding to U.S. Appl. No. 10/877,303 dated Apr. 3, 2008.
Official Action corresponding to U.S. Appl. No. 10/877,303 dated Oct. 16, 2008.
Official Action corresponding to U.S. Appl. No. 11/820,481 dated Jun. 23, 2008.
Official Action corresponding to U.S. Appl. No. 11/820,481 dated Dec. 15, 2008.
Official Action corresponding to U.S. Appl. No. 11/820,481 dated May 11, 2009.
Official Action corresponding to U.S. Appl. No. 11/820,481 dated Aug. 17, 2009.
Official Action corresponding to U.S. Appl. No. 11/820,481 dated Nov. 20, 2009.
Ogiso et al., Pharmacokinetics of indomethacin ester prodrugs: gastrointestinal and hepatic toxicity and hydrolytic capacity of various tissues in rats. *Biological and Pharmaceutical Bulletin*. vol. 19, No. 9 pp. 1178-1183 (1996) (Abstract).
O'Sullivan et al., Lipopolysaccharide-induced expression of prostaglandin H synthase-2 in alveolar macrophages is inhibited by dexamethasone but not by aspirin. *Biochemical and Biophysical Research Communications*. vol. 191, No. 3 pp. 1294-1300 (1993).
Otis et al., Synthesis and Pharmacological Evaluation of Amide Derivatives of Non-steroidal Anti-Inflammatory Drugs. *Inflammopharmacology*. vol. 1, No. 3 pp. 201-212 (1992).
Pal et al., 7-Oxabicycloheptylprostanoic Acids: Potent, Time-Dependent Cyclooxygenase Inhibitors that Induce a Conformational Change in the Prostaglandin Endoperoxide Synthase Protein. *Journal of Medicinal Chemistry*. vol. 35, No. 12 pp. 2340-2342 (1992).
Penning et al., Synthesis and Biological Evaluation of the 1,5-Diarylpyrazole Class of Cyclooxygenase-2 Inhibitors: Indentification of 4-[5(4-Methylphenyl)-3- (trifluoromethyl)-1H-pyrazol-1yl]benzenesulfonamide (SC-58635, Celecoxib). *Journal of Medicinal Chemistry*. vol. 40 pp. 1347-1365 (1997).
Phelan et al., Improved Delivery Through Biological Membranes. XXXVII. Synthesis and Stability of Novel Redox Derivatives of Naproxen and Indomethacin. *Pharmaceutical Research*. vol. 6, No. 8 pp. 667-676 (1989).
Physician's Desk Reference, 41st Edition, pp. 1305-1310 (1987) Indocin® (Indomethacin, MSD).
Prasit et al., L-745,337: A Selective Cyclooxygenase-2 Inhibitor. *Medicinal Chemistry Research*. vol. 5 pp. 364-374 (1995).
Prusakiewicz et al., Molecular basis of the time-dependent inhibition of cyclooxygenases by indomethacin. *Biochemistry*. vol. 43, No. 49 pp. 15439-15445 (2004).
Ramesha, Human and Rat Cyclooxygenases are Pharmacologically Distinct. *Eicosanoids Other Bioactive Lipids in Cancer Inflammation and Radiation Injury*. Chp. 10 pp. 67-71 (1997).
Reitz et al., Novel 1,2-Diarylcyclopentenes are Selective, Potent, and Orally Active Cyclooxygenase Inhibitors. *Medicinal Chemistry Research*. vol. 5, No. 3 pp. 351-363 (1995).
Riendeau et al., Biochemical and pharmacological profile of a tetrasubstituted furanone as a higly selective COX-2 inhibitor. *British Journal of Pharmacology*. vol. 121 pp. 105-117 (1997).
Rojo et al., Variable Effects of Indomethacin and Four Related Compounds on Lymphocyte Blastogenesis and Cell-mediated Cytotoxicity. *International Journal of Clinical Pharmacology, Therapy, and Toxicology*. vol. 19, No. 9 pp. 420-424 (1981) (Abstract).
Rojo et al., Variation in the immunosuppressive activity by structural modifications of a series of non-steroidal antiinflammatory drugs (indomethacin esters). *Arch. Farmacol. Toxicol.* vol. 4 No. 3 pp. 287-292 (1978) (Abstract).
Rouzer et al., Cyclooxygenase-1-dependent Prostaglandin Synthesis Modulates Tumor Necrosis Factor-α Secretion in Lipopolysaccharide-challenged Murine Resident Peritoneal Macrophages. *The Journal of Biological Chemistry*. vol. 279, No. 33 pp. 34256-34268 (2004).
Roy et al., A New Series of Selective COX-2 Inhibitors; 5,6-Diarylthiazolo[3,2-b][1,2,4]Triazoles. *Bioorganic & Medicinal Chemistry Letters*. vol. 7, No. 1 pp. 57-62 (1997).
Sauvaire et al., Pharmacological activity and toxicity of apyramide: comparison with non-steroidal anti-inflammatory agents. *Drugs Under Experimental and Clinical Research*. vol. 13, No. 5 pp. 247-252 (1987) (Abstract).
Shaw, The Synthesis of Tryptamines Related to Serotonin. *Journal of the American Chemical Society*. vol. 77 pp. 4319-4324 (1955).
Sheng et al., Inhibition of Human Colon Cancer Cell Growth by Selective Inhibition of Cyclooxygenase-2. The Journal of Clinical Investigation. vol. 99, No. 9 pp. 2254-2259 (1997).
Smith et al., Prostaglandin Endoperoxide H Synthases (Cyclooxygenases)-1 and -2. *The Journal of Biological Chemistry*. vol. 271, No. 52 pp. 33157-33160 (1996).
Soai et al., Mixed Solvents Containing Methanol as Useful Reaction Media for Unique Chemoselective Reductions with Lithium Borohydride. *Journal of Organic Chemistry*. vol. 51, No. 21 pp. 4000-4005 (1986).
Supplementary European Search Report corresponding to International Patent Application No. 05778497.7-2123/1744747 dated Nov. 2, 2009.
Svoboda et al., Potential Anti-inflammatory Agents on the Basis of Indomethacin Esters. *Ceskoslovenska Farmacie*. vol. 40, No. 2, pp. 71-74 (1991) (Abstract).
Tammara et al., Synthesis and Evaluation of Morpholinoalkyl Ester Prodrugs of Indomethacin and Naproxen. *Pharmaceutical Research*. vol. 10, No. 8 pp. 1191-1199 (1993).
Tanaka et al., Pharmacological Studies of the New Antiinflammatory Agent 3-Formylamino-7-Methylsulfonylamino-6-Phenoxy-4H-1-Benzopyran-4-One. *Arzneim-Forsch/Drug Res*. vol. 42(II), No. 7 pp. 935-944 (1992).
Therien et al., Synthesis and Biological Evaluation of 5,6-Diarylimidazo[2.1-b]Thiazole as Selective COX-2 Inhibitors. *Bioorganic & Medicinal Chemistry Letters*. vol. 7, No. 1 pp. 47-52 (1997).
Timofeevski et al., Isoform-Selective Interaction of Cyclooxygenase-2 with Indomethacin Amides Studied by Real-Time Fluorescence, Inhibition Kinetics, and Site-Directed Mutagenesis. *Biochemistry*. vol. 41 pp. 9654-9662 (2002).
Tsuji et al., Studies of Anti-inflammatory Agents. IV. Synthesis and Pharmacological Properties of 1,5-Diarylpyrazoles and Related Derivatives. *Chemical Pharmacology Bulletin*. vol. 45, No. 6 pp. 987-995 (1997).
Ueda et al., Design, synthesis and antiinflammatory activity of a new indomethacin ester, 2-[N-[3-{3-(piperidinomethyl)phenoxy}propyl]carbamoylmethylthio]ethyl 1-(p-chlorobenzoyl)-5-methoxy-2-methyl-indole-3-acetate. *Chemical Pharmacology Bulletin*. vol. 39, No. 3 pp. 679-684 (1991) (Abstract).
Vane et al., Inducible isoforms of cyclooxygenase and nitric-oxide synthase in inflammation. *PNAS USA*. vol. 91 pp. 2046-2050 (1994).
Wang et al., A Selective Method for the Preparation of Primary Amides: Synthesis of Fmoc-L-4- Carboxamidophenylalanine and Other Compounds. *Tetrahedron Letters*. vol. 40 pp. 2501-2504 (1999).
Whitehouse et al., Esterification of acidic antiinflammatory drugs suppresses their gastrotoxicity without adversely affecting their antiinflammatory activity in rats. Journal of Pharmacy and Pharmacology. vol. 32, No. 11, pp. 795-796 (1980). [Abstract].
Wiesenberg-Boettcher et al., The Pharmacological Profile of CGP 28238, a Novel Highly Potent Anti-Inflammatory Compound. *Drugs Under Experimental and Clinical Research*. vol. 15, No. 11-12 pp. 501-509 (1989) (Abstract).

Yamawaki et al., Piperazinealkanol ester derivatives of indomethacin as dual inhibitors of 5-lipoxygenase and cyclooxgenase. *Chemical Pharmacology Bulletin.* vol. 42, No. 4, pp. 963-971 (1994) (Abstract).

Yokoyama et al., Cloning of Human Gene Encoding Prostaglandin Endoperoxide Synthase and Primary Structure of the Enzyme. *Biochemical and Biophysical Research Communications.* vol. 165, No. 2 pp. 888-894 (1989).

Yoneda et al., Expression of Angiogeneis-Related Genes and Progression of Human Ovarian Carcinomas in Nude Mice. *Journal of the National Cancer Institute.* vol. 90, No. 6 pp. 447-454 (1998).

Yu et al., Synthesis of Prostaglandin E2 Ethanolamide from Anandamide by Cyclooxygenase-2. *The Journal of Biological Chemistry.* vol. 272, No. 34 pp. 21181-21186 (1997).

Zimmermann et al., Cyclooxygenase-2 Expression in Human Esophageal Carcinoma. Cancer Research. vol. 59 pp. 198-204 (1999).

Besselievre et al., Structural Immunochemistry of Melatonin-BSA Binding, Model of Amino and Indole Groups Cross-Linking. *Biomedicine Express.* vol. 33, No. 7 pp. 226-228 (1980).

Correspondence from foreign patent attorney regarding Chinese Patent Application No. 99816425.9 dated Jun. 21, 2004.

Correspondence from foreign patent attorney regarding Israel Patent Application No. 144,127 dated May 26, 2005.

Correspondence from foreign patent attorney regarding Israel Patent Application No. 144,127 dated Dec. 11, 2005.

Correspondence from foreign patent attorney regarding Notice of Allowance corresponding to Israel Patent Application No. 144,127 dated Jul. 5, 2006.

Decision to grant a European patent pursuant to article 97(2) EPC corresponding to European Patent Application No. 00957717.2-2117 dated Sep. 20, 2007.

Decision to grant a European patent pursuant to article 97(2) EPC corresponding to European Patent Application No. 99967416.1-2107 dated May 11, 2006.

Decision to grant a European patent pursuant to article 97(2) EPC corresponding to European Patent Application No. 99967417.9-1521 dated Apr. 26, 2007.

Del Rosario et al., Synthesis of [C-11]indomethacin methyl ester for in vivo brain studies of cyclooxygenase 2. *Journal of Nuclear Medicine.* vol. 37, No. 5 (1996) [Abstract].

European Search Report corresponding to European Patent Application No. 00957717.2-2123 dated Nov. 16, 2004.

European Search Report corresponding to European Patent Application No. 99967416.1-2107 dated Apr. 8, 2003.

Faust et al., Mapping the Melatonin Receptor. 6. Melatonin Agonists and Antagonists Derived from 6H-lsoindolo[2,1-a]indoles, 5,6-Dihydroindolo[2,1-a]isoquinolines, and 6,7-Dihydro-5H-benzo[c]azepino[2,1-a]indoles. *Journal of Medicinal Chemistry.* vol. 43 pp. 1050-1061 (2000).

Flaugh et al., Synthesis and Evaluation of the Antiovulatory Activity of a Variety of Melatonin Analogues. *Journal of Medicinal Chemistry.* vol. 22, No. 1 pp. 63-69 (1979).

Frohn et al., Structure—Activity Relationship of Melatonin Analogues. *Life Sciences.* vol. 27, No. 22, pp. 2043-2046 (1980).

Issued Patent corresponding to Chinese Patent No. ZL 99816425.9 dated Apr. 6, 2005.

Issued Patent corresponding to Israel Patent No. 144127 dated Nov. 3, 2007.

Issued Patent corresponding to Republic of China Invention Patent No. I286474 dated Sep. 11, 2007.

Kalgutkar et al., Ester and Amide Derivatives of the Nonsteroidal Antiinflammatory Drug, Cyclooxygenase-2 Inhibitors. *Journal of Medicinal Chemistry.* vol. 43, No. 15 pp. 2860-2870 (2000).

McMurray, R.W., and Hardy, K.J., Cox-2 Inhibitors: Today and Tomorrow. *The American Journal of the Medical Sciences.* vol. 323, No. 4 pp. 181-189 (2002).

Mor et al., Melatonin Receptor Ligands: Synthesis of New Melatonin Derivatives and Comprehensive Comparative Molecular Field Analysis (CoMFA) Study. *Journal of Medicinal Chemistry.* vol. 41, No. 20 pp. 3831-3844 (1998).

Notice of Acceptance corresponding to Australian Patent Application No. 23697/00 dated Mar. 19, 2004.

Notice of Acceptance corresponding to Australian Patent Application No. 23698/00 dated Apr. 1, 2003.

Notice of Acceptance corresponding to Australian Patent Application No. 69297/00 dated Mar. 9, 2004.

Notice of Allowance corresponding to U.S. Appl. No. 09/226,693 dated Oct. 24, 2000.

Notice of Allowance corresponding to U.S. Appl. No. 09/385,748 dated Jun. 5, 2001.

Notice of Allowance corresponding to U.S. Appl. No. 09/818,201 dated Jan. 15, 2002.

Notice of Allowance corresponding to U.S. Appl. No. 09/869,384 dated Nov. 6, 2003.

Notice of Allowance corresponding to U.S. Appl. No. 11/820,481 dated Jan. 29, 2010.

Notice of Decision of Granting Patent Right for Invention corresponding to Chinese Patent Application No. 99816425.9 dated Dec. 3, 2004.

Official Action corresponding to Australian Patent Application No. 23697/00 dated Nov. 15, 2002.

Official Action corresponding to Australian Patent Application No. 23697/00 dated Dec. 16, 2003.

Official Action corresponding to Australian Patent Application No. 23698/00 dated Nov. 15, 2002.

Official Action corresponding to Australian Patent Application No. 69297/00 dated Nov. 17, 2003.

Official Action corresponding to Chinese Patent Application No. 99816425.9 dated Aug. 20, 2003.

Official Action corresponding to European Patent Application No. 99 967 416.1-2107 dated May 27, 2004.

Official Action corresponding to European Patent Application No. 00 957 717.2-2117 dated Jul. 13, 2006.

Official Action corresponding to European Patent Application No. 05 778 497.7-2123 dated Mar. 12, 2010.

Official Action corresponding to Japanese Patent Application No. 2000-591862 dated May 6, 2010.

Official Action corresponding to Republic of China (Taiwan) Patent Application No. 89117582 dated Dec. 20, 2003.

Official Action corresponding to Republic of China (Taiwan) Patent Application No. 89117582 dated Jul. 1, 2005.

Official Action corresponding to Republic of China (Taiwan) Patent Application No. 89117582 dated May 19, 2006.

Official Action corresponding to Republic of China (Taiwan) Patent Application No. 89117582 dated Jan. 26, 2007.

Official Action corresponding to U.S. Appl. No. 09/226,693 dated Mar. 27, 2000.

Official Action corresponding to U.S. Appl. No. 09/385,748 dated Aug. 7, 2000.

Official Action corresponding to U.S. Appl. No. 09/385,748 dated Nov. 13, 2000.

Official Action corresponding to U.S. Appl. No. 09/869,384 dated Nov. 22, 2002.

Official Action corresponding to U.S. Appl. No. 09/869,384 dated Apr. 8, 2003.

Supplementary European Search Report corresponding to European Patent Application No. 99967417.9 dated Jul. 25, 2003.

European Search Report corresponding to European Patent Application No. 04777110.0-1216 / 163862 dated Aug. 31, 2010.

Kalgutkar et al., "Covalent Modification of Cyclooxygenase-2 (COX-2) by 2-Acetoxyphenyl Alkyl Sulfides, A New Class of Selective COX-2 Inactivators," J. Med. Chem., vol. 41, pp. 4800-4818 (1998).

Kurumbail et al., "Structural basis for selective inhibition of cylooxygenase-2 by anti-inflammatory agents," Nature, vol. 384, pp. 644-648 (1996).

Official Action corresponding to Chinese Patent Application No. 200780030881.X dated Feb. 24, 2011.

Official Action corresponding to European Patent Application No. 05 778 497.7-2123 dated Nov. 29, 2010.

Official Action corresponding to European Patent Application No. 04777 110.0-1216 dated Jan. 26, 2011.

Official Action corresponding to Japanese Patent Application No. 2000-591861 dated Aug. 3, 2010.
Official Action corresponding to Japanese Patent Application No. 2006-517674 dated Aug. 27, 2010.
Official Action corresponding to Japanese Patent Application No. 2001-519900 dated Dec. 21, 2010.
Official Action corresponding to U.S. Appl. No. 12/423,358 dated May 27, 2011.
Official Action corresponding to U.S. Appl. No. 12/814,143 dated Jan. 14, 2011.
Official Action corresponding to U.S. Appl. No. 12/814,143 dated Oct. 8, 2010.

Indomethacin    DM-INDO

INDOLEACETIC ACID AND INDENACETIC ACID DERIVATIVES AS THERAPEUTIC AGENTS WITH REDUCED GASTROINTESTINAL TOXICITY

GRANT STATEMENT

This work was supported by grant number CA89450 from the U.S. National Institutes of Health. Thus, the U.S. government has certain rights in the presently disclosed subject matter.

CROSS REFERENCE TO RELATED APPLICATIONS

The present patent application claims benefit of U.S. patent application Ser. No. 11/114,921, filed Apr. 26, 2005, the contents of which is incorporated herein by reference in its entirety, which itself claims the benefit of U.S. Provisional Application Ser. No. 60/565,489, filed Apr. 26, 2004, the contents of which is also incorporated herein by reference in its entirety.

TECHNICAL FIELD

The presently disclosed subject matter generally relates to derivatives of non-steroidal anti-inflammatory drugs (NSAIDs) that have been modified to decrease their ability to inhibit cyclooxygenase enzymes. Also provided are methods for altering the specificity of a cyclooxygenase-inhibiting compound and methods of using the altered compounds to modulate various biological activities.

TABLE OF ABBREVIATIONS

15d-PGJ$_2$—15-deoxy-$\Delta^{12,14}$-prostaglandin J$_2$
AA—arachidonic acid
AD—Alzheimer's disease
APP—amyloid precursor protein
ATCC—American Type Culture Collection
CCDB—Cambridge Crystallographic Data Bank
CNS—central nervous system
COX—cyclooxygenase
COX-1—cyclooxygenase-1
COX-2—cyclooxygenase-2
DMAP—dimethylaminopyridine
DMEM—Dulbecco's modified Eagle's medium
DM-INDO—2-Des-methylindomethacin
DMSO—dimethyl sulfoxide
DTT—dithiothreitol
EBA—ethyl bromoacetate
ED$_{50}$—the concentration of an compound that reduces cell viability by 50%
EDCI—N-(3-dimethylaminopropyl)-N'-ethyl carbodiimide
EDTA—ethylenediamine tetraacetic acid
ESI-MS—electrospray ionization
Et$_2$O—diethyl ether
EtOAc—ethyl acetate
FBS—fetal bovine serum
GI—gastrointestinal
HOAc—acetic acid
IC$_{50}$—the concentration of an inhibitor that reduces enzyme or cellular activity by 50%
INDO—indomethacin
mCOX-2—murine COX-2
MODY—maturity onset diabetes of the young
NSAIDs—non-steroidal anti-inflammatory drugs
oCOX-1—ovine COX-1
PG—prostaglandin
PMA—phosphomolybdic acid
PMTBA—p-methylthiobenzaldehyde
PPA—polyphosphoric acid
PPARs—peroxisome proliferator[s]-activated receptors
ppm—parts per million
PTSA—p-toluene sulfonic acid.H$_2$O
SDS—sodium dodecyl sulfate
SDS-PAGE—sodium dodecyl sulfate-polyacrylamide gel electrophoresis
S.E.—standard error
TMS—tetramethylsilane

BACKGROUND

Non-steroidal anti-inflammatory drugs (NSAIDs) are a class of therapeutic agents that are widely used for their anti-inflammatory and anti-pyretic properties to treat human distress and disease. Exemplary NSAIDs include aspirin, ibuprofen, acetaminophen, indomethacin, naproxen, and others.

The anti-inflammatory and anti-pyretic activities of NSAIDs derive from the ability of these compounds to bind to and inhibit the actions of the cyclooxygenase (COX) enzymes. COX activity originates from two distinct and independently regulated enzymes, termed cyclooxygenase-1 (COX-1) and cyclooxygenase-2 (COX-2; see Dewitt & Smith, 1988; Yokoyama & Tanabe, 1989; Hla & Neilson, 1992). COX-1 is a constitutive isoform and is mainly responsible for the synthesis of cytoprotective prostaglandin in the gastrointestinal (GI) tract and for the synthesis of thromboxane, which triggers aggregation of blood platelets (Allison et al., 1992). On the other hand, COX-2 is inducible and short-lived. Its expression is stimulated in response to endotoxins, cytokines, and mitogens (Kujubu et al., 1991; Lee et al., 1992; O'Sullivan et al., 1993). NSAIDs exhibit varying selectivity for COX-1 and COX-2 but, in general, most display inhibitory activity towards both enzymes (Meade et al., 1993).

Inflammation and inflammatory responses have been associated with various diseases and disorders. For example, the brains of subjects with Alzheimer's disease (AD) are characterized by the accumulation of amyloid plaques accompanied by cellular and molecular markers of inflammatory responses. AD is the most common cause of dementia in the elderly, resulting in enormous costs to individuals and to society, both in terms of medical care and non-economic losses. As the population ages, it is undeniable that AD and related neurological disorders will become an ever-increasing medical and societal burden. What is needed, then, are new and better therapeutics that can be used to prevent and treat age-related neurological disorders.

Interestingly, epidemiological studies have suggested that long-term treatment with NSAIDs might provide a protective effect against the development of AD. Initially, it was believed that the protective effect derived from the anti-inflammatory actions of NSAIDs, but this hypothesis has recently been questioned. Several recent reports suggest instead that the protective effects are independent of the ability of NSAIDs to inhibit cyclooxygenases. Thus, treatment with NSAIDs might be useful to decrease the incidence and/or the severity of AD and related disorders.

Long-term use of NSAIDs is not without risks, however. In particular, most NSAIDs, particularly those that are inhibitors of COX-1, are associated with significant GI toxicities. As such, the long-term use of these drugs must be approached with caution. This requires a careful balance between the use of NSAIDs for their potential benefits vis-à-vis neurological disorders and the GI toxicity associated with their use. A more favorable approach would be to find or create new derivatives of NSAIDs that retain their protective effects but do not cause debilitating and potentially fatal toxicities.

One potential approach would be to employ NSAIDs that are specific for COX-2. Several such NSAIDs have been produced, including celecoxib, valdecoxib (CELEBREX™ and BEXTRA™, respectively; Pfizer Inc., New York, N.Y., United States of America), rofecoxib, etoricoxib (VIOXX™ and ARCOXIA™, respectively; Merck and Co., Inc., Whitehouse Station, N.J., United States of America), and lumiracoxib (PREXIGE®; Novartis Pharmaceuticals Corporation, East Hanover, N.J., United States of America). Unfortunately, recent evidence indicates that these COX-2-specific inhibitors do not provide any protective effect against the development of AD. In both in vivo and in vitro assays, neither celecoxib nor rofecoxib appeared capable of inhibiting the production of the Aβ42 protein, the cleavage product of the amyloid precursor protein (APP) believed to be responsible for the formation of amyloid plaques. Accordingly, it appears that simply using COX-2-specific NSAIDs is unlikely to provide the protective effects currently seen with other non-specific NSAIDs.

Additional evidence seems to suggest that the protective effects afforded by certain NSAIDs, such as ibuprofen, sulindac sulfide, and indomethacin (all non-specific NSAIDs), might not be related to their COX-inhibition activities, and thus might be related to the abilities of these NSAIDs to interact with other polypeptides present in the central nervous system (CNS). Two such polypeptides are the class of peroxisome proliferators-activated receptors (PPARs) and γ-secretase. For example, PPARs, particularly PPARγ, have been implicated in mediating differentiation of adipocytes and regulating fat metabolism. Additionally, PPARγ has been associated with various pathological conditions related to atherosclerosis, inflammation, obesity, diabetes, cancer, the immune response, and ageing. See Kersten et al., 2000; Celi & Shuldiner, 2002. γ-secretase, on the other hand, appears to be the main enzyme responsible for the production of Aβ42 from APP, and thus has a critical role in the pathogenesis of AD.

What are needed, then, are new derivatives of NSAIDs that are less toxic than the parent NSAIDs, yet retain the abilities of the parents to modulate the activities of, for example, PPARs and/or γ-secretase. This and other needs are addressed by the compositions and methods of the presently disclosed subject matter.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides a method for inhibiting growth of a cell. In some embodiments, the method comprises contacting the cell with a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl. In some embodiments, the cyclooxygenase inhibitor comprises an indenacetic acid functional group and the moiety is selected from the group consisting of hydrogen and fluorine. In some embodiments, the cell is present in a subject. In some embodiments, the cell is a tumor cell. In some embodiments, the subject is a mammal. In some embodiments, the mammal is a human.

In some embodiments, the compound is a non-steroidal anti-inflammatory drug. In some embodiments, the non-steroidal anti-inflammatory drug is selected from the group consisting of indomethacin, sulindac, pharmaceutically acceptable salts thereof, and combinations thereof. In some embodiments, the derivative of the compound is an amide or ester derivative.

The presently disclosed subject matter also provides a method for treating a disease in a subject selected from the group consisting of a cancer, a neurodegenerative disease, and diabetes. In some embodiments, the method comprises administering to the subject a treatment effective amount of a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl. In some embodiments, the cyclooxygenase inhibitor comprises an indenacetic acid functional group and the moiety is selected from the group consisting of hydrogen and fluorine. In some embodiments, the subject is a mammal. In some embodiments, the mammal is a human. In some embodiments, the neurodegenerative disease is Alzheimer's disease.

In some embodiments, the compound is a non-steroidal anti-inflammatory drug. In some embodiments, the non-steroidal anti-inflammatory drug is selected from the group consisting of indomethacin and sulindac, and pharmaceutically acceptable salts thereof, and combinations thereof. In some embodiments, the derivative of the compound is an amide or ester derivative. In some embodiments, the derivative causes substantially less gastrointestinal toxicity than does the compound. In some embodiments, the derivative of the compound is an amide or ester derivative.

The presently disclosed subject matter also provides a method for suppressing tumor growth in a subject. In some embodiments, the method comprises administering to a subject bearing a tumor a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl. In some embodiments, the cyclooxygenase inhibitor comprises an indenacetic acid functional group and the moiety is selected from the group consisting of hydrogen and fluorine. In some embodiments, the subject is a mammal. In some embodiments, the mammal is a human.

In some embodiments, the compound is a non-steroidal anti-inflammatory drug. In some embodiments, the non-steroidal anti-inflammatory drug is selected from the group consisting of indomethacin and sulindac, and pharmaceutically acceptable salts thereof, and combinations thereof. In some embodiments, the derivative of the compound is an amide or ester derivative. In some embodiments, the derivative causes substantially less gastrointestinal toxicity than does the compound.

The presently disclosed subject matter also provides a method for inducing apoptosis in a cell. In some embodiments, the method comprises contacting the cell with a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl. In some embodiments, the cyclooxygenase inhibitor comprises an indenacetic acid functional group and the moiety is selected from the group consisting of hydrogen and fluorine. In some embodiments, the cell is a cell in culture. In some embodiments, the cell is a cancer cell. In some embodiments, the cell is present within a subject. In some embodiments, the subject is a mammal. In some embodiments, the mammal is a human.

In some embodiments, the compound is a non-steroidal anti-inflammatory drug. In some embodiments, the non-steroidal anti-inflammatory drug is selected from the group consisting of indomethacin and sulindac, and pharmaceutically acceptable salts thereof, and combinations thereof. In some embodiments, the derivative of the compound is an amide or ester derivative.

The presently disclosed subject matter also provides a method for modulating the activity of a peroxisome proliferators-activated receptor (PPAR) isoform. In some embodiments, the method comprises contacting the PPAR isoform with a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl. In some embodiments, the cyclooxygenase inhibitor comprises an indenacetic acid functional group and the moiety is selected from the group consisting of hydrogen and fluorine. In some embodiments, the PPAR isoform is PPARγ. In some embodiments, the PPAR isoform is present within a subject. In some embodiments, the subject is a mammal. In some embodiments, the mammal is a human.

In some embodiments, the compound is a non-steroidal anti-inflammatory drug. In some embodiments, the non-steroidal anti-inflammatory drug is selected from the group consisting of indomethacin, sulindac, pharmaceutically acceptable salts thereof, and combinations thereof. In some embodiments, the derivative of the compound is an amide or ester derivative. In some embodiments, the derivative causes substantially less gastrointestinal toxicity than does the compound.

The presently disclosed subject matter also provides a method for altering specificity of a cyclooxygenase-inhibiting compound. In some embodiments, the method comprises (a) providing a compound having cyclooxygenase inhibitory activity, the compound comprising an indoleacetic acid or indenacetic acid functional group having a 2' methyl group; and (b) replacing the 2' methyl group with a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl to create a derivative, wherein the derivative substantially lacks cyclooxygenase inhibitory activity. In some embodiments, the compound is a non-steroidal anti-inflammatory drug. In some embodiments, the non-steroidal anti-inflammatory drug is selected from the group consisting of indomethacin and sulindac, and pharmaceutically acceptable salts thereof, and combinations thereof. In some embodiments, the derivative is selected from the group consisting of 2-Des-methylindomethacin and eindenic acid sulfide, eindenic acid sulfoxide, and eindenic acid sulfone. In some embodiments, the derivative is eindenic acid sulfide. In some embodiments, the present method further comprises derivatizing a carboxylic acid moiety present on the compound to an ester or an amide.

The presently disclosed subject matter also provides compositions that can be used in conjunction with any or all of the disclosed methods. In some embodiments, the presently disclosed subject matter provides a compound of the following formula:

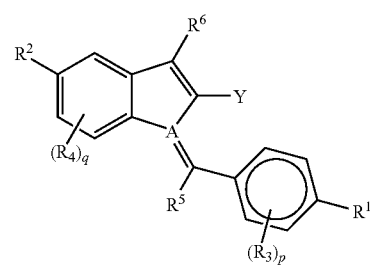

Formula I wherein
  $R^1$ is selected from the group consisting of hydrogen, halo, $CF_3$; $SCH_3$; $SOCH_3$; $SO_2CH_3$; $SO_2NH_2$; $C_1$ to $C_6$ alkyl, branched alkyl, or substituted alkyl; $C_1$ to $C_6$ alkoxy, branched alkoxy, or substituted alkoxy; $C_1$ to $C_6$ alkylcarboxylic acid, branched alkylcarboxylic acid, or substituted alkylcarboxylic acid; and $CH_2N_3$;
  $R^2$ is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;
  $R^3$ and $R^4$ are each independently selected from the group consisting of hydrogen; halo; $CF_3$; $C_1$ to $C_6$ alkyl, branched alkyl, or substituted alkyl; $C_1$ to $C_6$ alkoxy, branched alkoxy, or substituted alkoxy; aryl; substituted aryl; benzyloxy; $SCH_3$; $SOCH_3$; $SO_2CH_3$; and $SO_2NH_2$;
  $R^5$ is selected from the group consisting of hydrogen, $C_1$ to $C_6$ alkyl, branched alkyl, or substituted alkyl, and =O;
  $R^6$ is selected from the group consisting of hydrogen; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and the following structure:

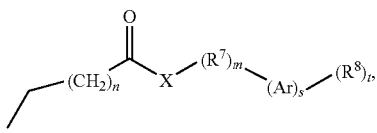

wherein
Ar is cyclohexyl or phenyl;
$R^7$ is hydrogen; $C_1$ to $C_6$ alkyl, branched alkyl, or substituted alkyl;
$R^8$ is hydrogen, halo, $C_1$ to $C_6$ alkyl, branched alkyl, and substituted alkyl; $C_1$ to $C_6$ alkoxy, branched alkoxy, and substituted alkoxy; $C_1$ to $C_6$ alkylcarboxylic acid, branched alkylcarboxylic acid, or substituted alkylcarboxylic acid; amino; nitro; $CF_3$; bromoacetamidyl; benzoyl; or 2-phenyl-oxiranyl;
X is O or $NR^9$, wherein $R^9$ is hydrogen or alkyl; and
m, n, s, and t are each individually 0, 1, 2, 3, 4, or 5;
Y is selected from the group consisting of hydrogen, halo, $CF_3$, and $C_2$ to $C_6$ alkyl or branched alkyl;
A is selected from the group consisting of carbon and nitrogen;
p and q are both individually 0, 1, 2, 3, or 4;
the bond between the carbon bound to $R^5$ and the indene ring and is a single bond or a double bond; and
the six-membered ring to which $R^1$ is bound is cyclohexyl or phenyl.

In some embodiments, $R^1$ is selected from the group consisting of halo, $C_1$ to $C_6$ alkyl or branched alkyl, $SCH_3$, $SOCH_3$, $SO_2CH_3$, and $SO_2NH_2$; $R^2$ is selected from the group consisting of hydrogen; halo; $C_1$ to $C_6$ alkyl or branched alkyl; $C_1$ to $C_6$ alkoxy or branched alkoxy; benzyloxy; $SCH_3$; $SOCH_3$; $SO_2CH_3$; $SO_2NH_2$; and $CONH_2$; $R^3$ and $R^4$ are each independently selected from the group consisting of hydrogen, $C_1$ to $C_6$ alkyl or branched alkyl, and halo; $R^5$ is selected from the group consisting of hydrogen, $C_1$ to $C_6$ alkyl or branched alkyl, and carbonyl; $R^6$ is selected from the group consisting of $C_1$ to $C_6$ alkylcarboxylic acid and branched $C_1$ to $C_6$ alkylcarboxylic acid; Y is selected from the group consisting of hydrogen, halo, and $C_2$ to $C_6$ alkyl or branched alkyl; A is selected from the group consisting of carbon and nitrogen; and the bond between the carbon bound to $R^5$ and the indene ring is a single bond or a double bond. In some embodiments, the derivative is selected from the group consisting of 2-Desmethylindomethacin and eindenic acid sulfide, eindenic acid sulfoxide, and eindenic acid sulfone. In some embodiments, the derivative is eindenic acid sulfide.

In some embodiments, the compound has the following formula:

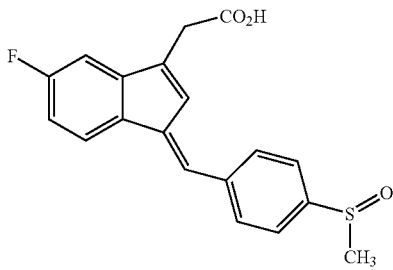

Eindenic acid sulfoxide

In some embodiments, the compound has the following formula:

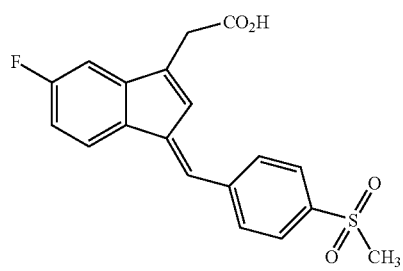

Eindenic acid sulfone

In some embodiments, the compound has the following formula:

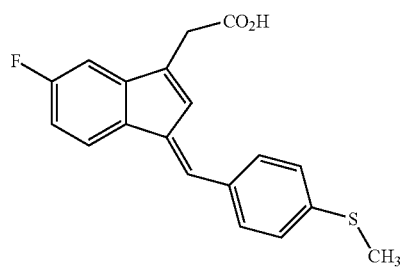

Eindenic acid sulfide

In some embodiments, the presently disclosed subject matter provides a compound of one of the following formulas:

Formula Ia

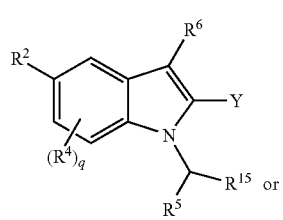

Formula Ib

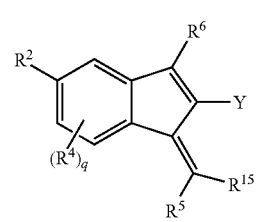

wherein
$R^2$ is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;
$R^4$ is selected from the group consisting of hydrogen; halo; $CF_3$; $C_1$ to $C_6$ alkyl, branched alkyl, or substituted alkyl;

$C_1$ to $C_6$ alkoxy, branched alkoxy, or substituted alkoxy; aryl; substituted aryl; benzyloxy; $SCH_3$; $SOCH_3$; $SO_2CH_3$; and $SO_2NH_2$;

$R^5$ is selected from the group consisting of hydrogen, $C_1$ to $C_6$ alkyl, $C_1$ to $C_6$ branched alkyl, and $C_1$ to $C_6$ substituted alkyl, and in the case of Formula Ia, =O;

$R^6$ is selected from the group consisting of hydrogen; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and the following structure:

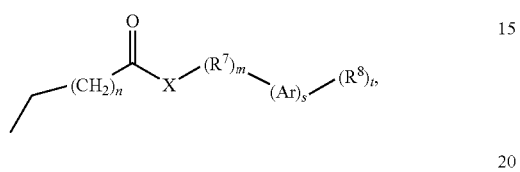

wherein
Ar is cyclohexyl or phenyl;
$R^7$ is hydrogen; $C_1$ to $C_6$ alkyl, branched alkyl, or substituted alkyl;
$R^8$ is hydrogen, halo, $C_1$ to $C_6$ alkyl, branched alkyl, and substituted alkyl; $C_1$ to $C_6$ alkoxy, branched alkoxy, and substituted alkoxy; $C_1$ to $C_6$ alkylcarboxylic acid, branched alkylcarboxylic acid, or substituted alkylcarboxylic acid; amino; nitro; $CF_3$; bromoacetamidyl; benzoyl; or 2-phenyl-oxiranyl;
X is O or $NR^9$, wherein $R^9$ is hydrogen or alkyl; and
m, n, and t are each individually 0, 1, 2, 3, 4, or 5;

$R^{15}$ is selected from the group consisting of cyclohexyl and an aromatic substituent, wherein the aromatic substituent comprises an aryl, a heteroaryl, and singly or multiply substituted derivatives thereof;

Y is selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl; and
q is 0, 1, 2, 3, or 4.

In some embodiments, $R^{15}$ comprises an aryl comprising multiple aromatic rings that are fused together or covalently linked. In some embodiments, the multiple aromatic rings are covalently linked by a moiety selected from the group consisting of an alkylene moiety, a carbonyl, oxygen, diphenylether, and nitrogen. In some embodiments, the multiple aromatic rings are selected from the group consisting of naphthyl, biphenyl, diphenylether, diphenylamine, and benzophenone.

In some embodiments, $R^2$ is selected from the group consisting of halo, $C_1$ to $C_6$ alkyl or branched alkyl, $SCH_3$, $SOCH_3$, $SO_2CH_3$, and $SO_2NH_2$. In some embodiments, $R^2$ is F.

In some embodiments, $R^{15}$ is in the E orientation with respect to the indene ring. In some embodiments, $R^3$ comprises one of the following formulas:

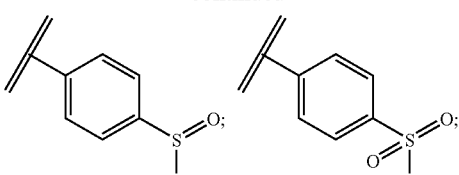
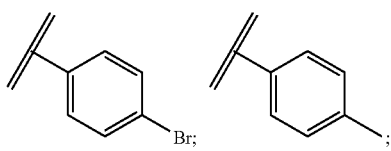
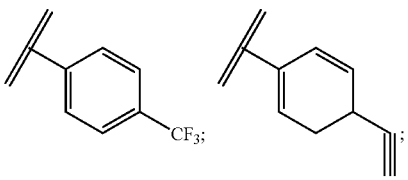
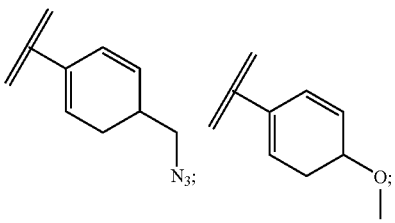
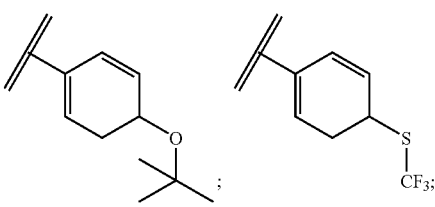
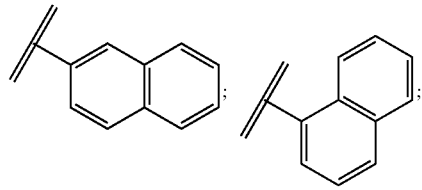
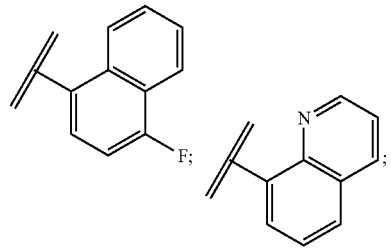
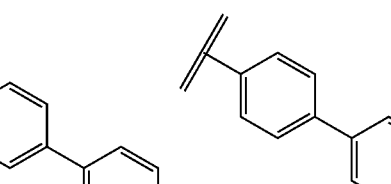
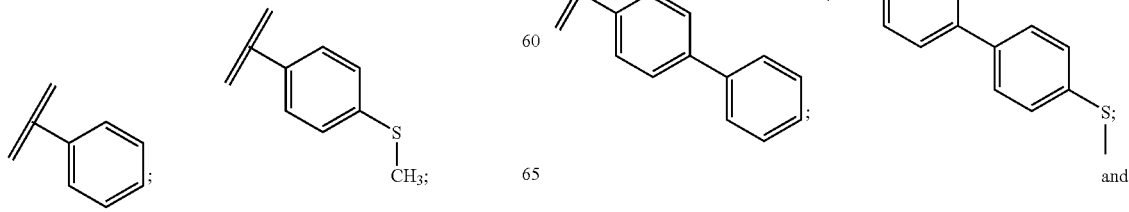

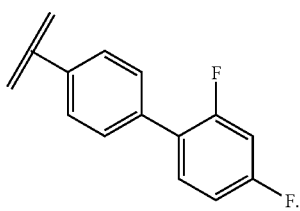
In some embodiments, the compound has one of the following formulas:
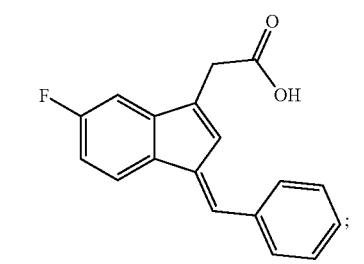
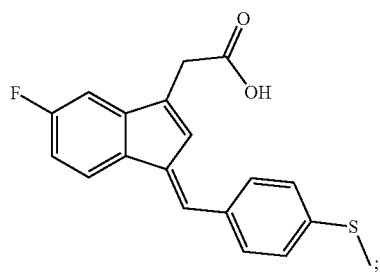
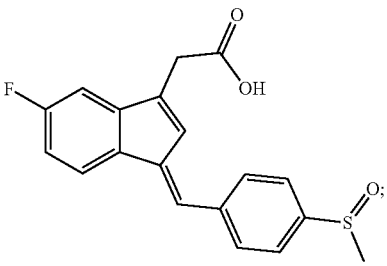
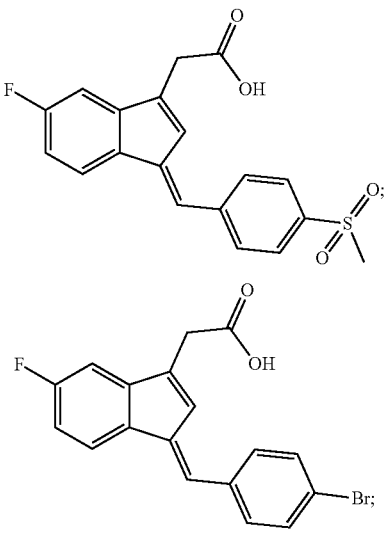
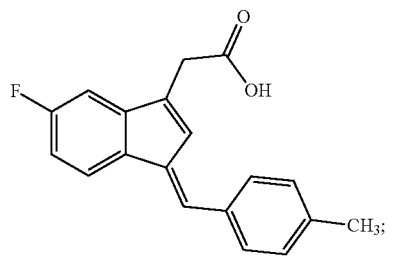
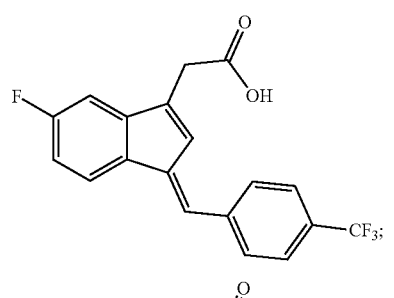
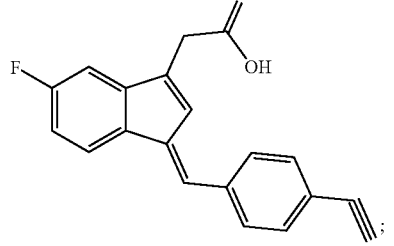
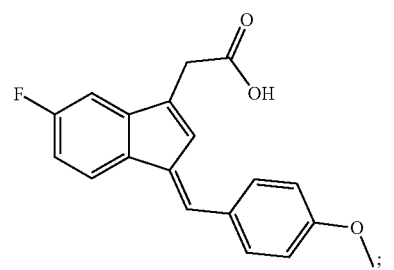
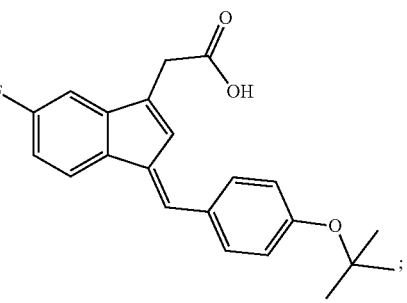

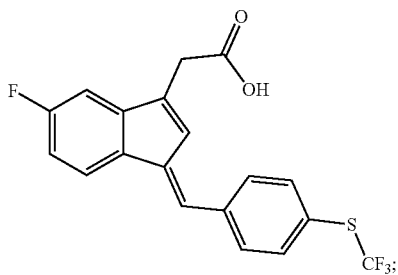

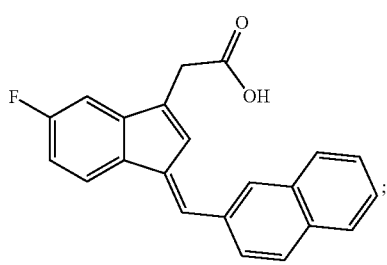

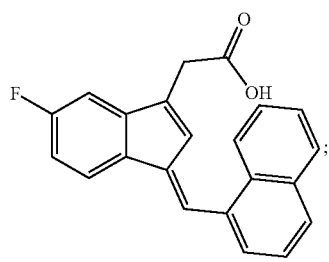

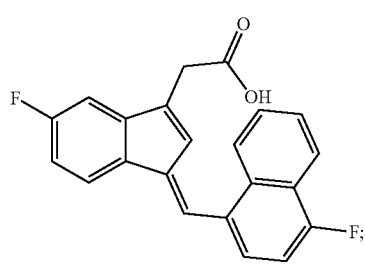

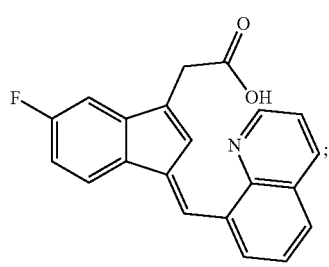

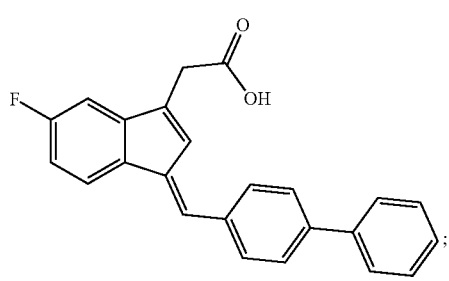

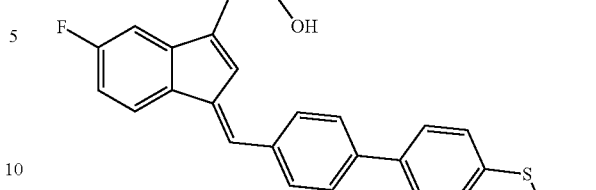

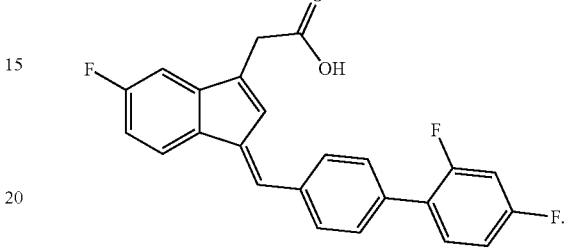

In some embodiments, the method further comprises derivatizing a carboxylic acid moiety present on the compound to an amide. In some embodiments, the amide derivative has the following general formula:

Formula II

In some embodiments, $R^{11}$ is selected from the group consisting of $C_1$ to $C_6$ alkyl, branched alkyl, and cyclic alkyl. In some embodiments, $R^{11}$ is selected from the group consisting of $C_1$ to $C_6$ alkylcarboxylic acid, branched alkylcarboxylic acid, and cyclic alkylcarboxylic acid. In some embodiments, $R^{11}$ is selected from the group consisting of $C_1$ to $C_6$ aryl and $C_1$ to $C_6$ substituted aryl. In some embodiments of the substituted aryl, the substitution is at least one position, and each substitution is selected from the group consisting of a halogen, $NH_2$, $OCH_3$, $CF_3$, $OH$, $C_1$ to $C_4$ alkyl or branched alkyl, $NO_2$, benzoyl, 2-phenyl-oxirane, and $NH-CO-CH_2Br$.

In some embodiments, the amide derivative has the following general formula:

Formula III

wherein $R^{12}$ is selected from the group consisting of phenyl-$SOCH_3$, phenyl-$SO_2CH_3$, phenyl, phenyl methyl ester, phenyl-COOH, phenyl-halo, and $C_3$ to $C_6$ cycloalkyl. Representative amide derivatives are presented in Tables 1 and 2.

In some embodiments, the method further comprises derivatizing a carboxylic acid moiety present on the compound to an ester or an amide. In some embodiments, the ester or amide has the following general formula:

Formula IV

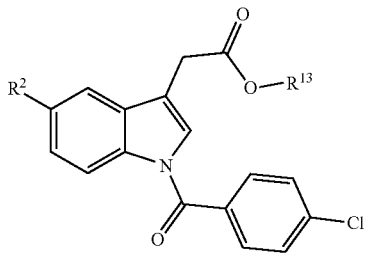

wherein $R^2$ is defined as above, $R^{13}$ is selected from the group consisting of $C_1$ to $C_6$ alkyl, $C_1$ to $C_6$ branched alkyl, and $C_1$ to $C_6$ substituted alkyl. In some embodiments, the ester derivative has the following formula:

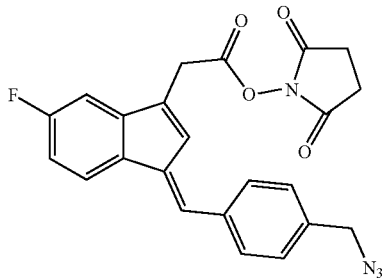

Accordingly, it is an object of the presently disclosed subject matter to provide new therapeutic agents for use in treating and/or preventing disease. This object is achieved in whole or in part by the presently disclosed subject matter.

An object of the presently disclosed subject matter having been stated hereinabove, other objects will be evident as the description proceeds and as best described hereinbelow.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

FIGS. 1A and 1B depict stereo views of INDO co-crystallized with COX-2 (Protein Data Bank code 4COX; Kurumbail et al., 1996). In FIG. 1A, key active site residues for catalysis and the binding of ligands are shown. FIG. 1B is a space-filling model of the 2' methyl substituent of INDO (green) inserted into the hydrophobic pocket formed by Val-349, Ala-527, Ser-530, and Leu-531.

FIG. 1C depicts the chemical structures of INDO and DM-INDO.

FIGS. 2A and 2C depict representative data expressed as percent activity of the uninhibited control with non-linear regression curves. The curves drawn as secondary plots for FIG. 2B and FIG. 2D were generated by fitting the data presented in FIGS. 2A and 2C, respectively, to equation (2), disclosed hereinbelow.

FIG. 5A depicts the results obtained with an mCOX-$2^{V349A}$ polypeptide. FIG. 5B depicts the results obtained with a wild type mCOX-2 polypeptide. FIG. 5C depicts the results obtained with an mCOX-$2^{V349I}$ polypeptide. FIG. 5D depicts the results obtained with an mCOX-$2^{V349L}$ polypeptide. The final concentrations of INDO and DM-INDO employed were 1 μM (FIG. 5A), 2 μM (FIG. 5B),) 3 μM (FIG. 5C), and 5 μM (FIG. 5D).

DETAILED DESCRIPTION

Figure 1:
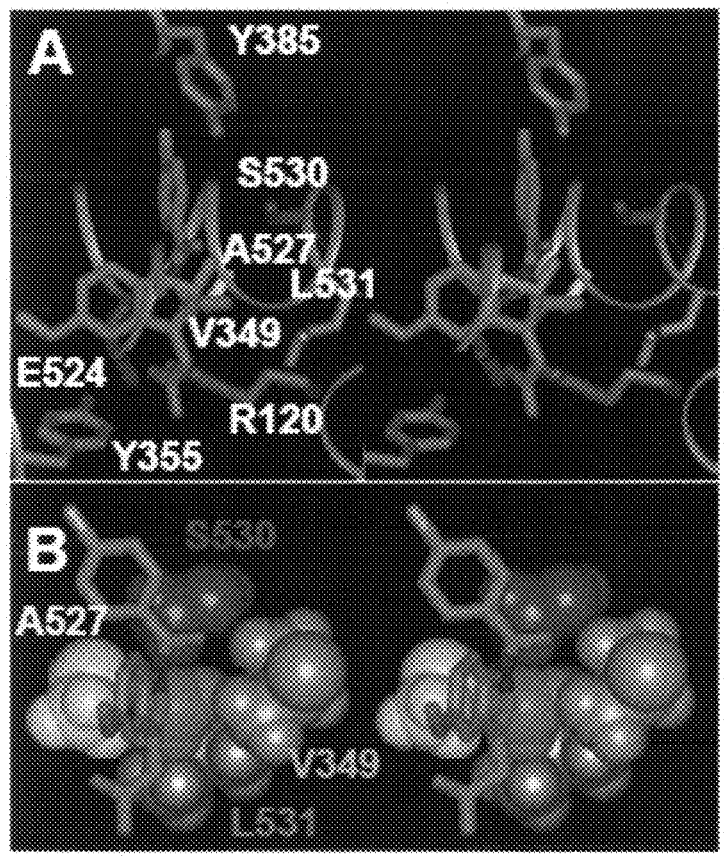
FIGS. 1A-1C depict a crystal structure of indomethacin (INDO) bound in the COX-2 active site.
Figure 1:
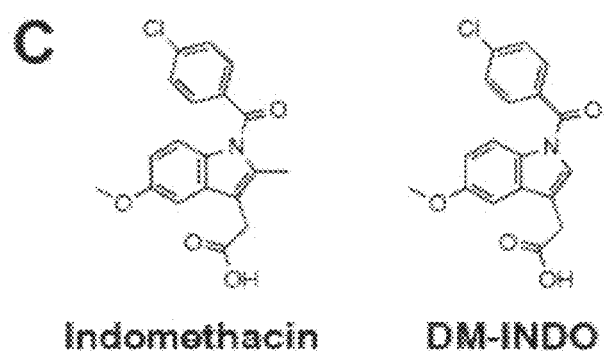

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

All publications, patent applications, patents, and other references mentioned herein are incorporated by reference in their entirety.

Throughout the specification and claims, a given chemical formula or name shall encompass all optical isomers and stereoisomers as well as racemic mixtures where such isomers and mixtures exist.

I. GENERAL CONSIDERATIONS

Non-steroidal anti-inflammatory drugs (NSAIDs) exert a range of biological activities including inhibition of inflammation, inhibition of pain, lowering of fever, inhibition of tumor growth, inhibition of Alzheimer's disease, and improvement of cognitive function in neurodegenerative diseases, inter alia. Some of these effects are mediated by inhibition of cyclooxygenase enzymes (COX-1 and COX-2) whereas others are mediated by modulation of other molecular targets. The latter include, but are not limited to activation of peroxisome proliferators-activated receptors (PPARs), modulation of γ-secretase, inhibition of c-GMP phosphodiesterase subtypes, and inhibition of Rho activation. Two compounds that exhibit activities in both cyclooxygenase-related and non-cyclooxygenase-related responses are indomethacin and sulindac sulfide. Indomethacin is directly active following administration to humans whereas sulindac sulfide is administered as the inactive prodrug sulindac. Sulindac is converted to the active drug, sulindac sulfide, by reduction in the gastrointestinal tract.

Indomethacin and sulindac sulfide are structurally related molecules that contain substituted indoleacetic acid and indeneacetic acid functional groups, respectively. Both molecules contain a methyl group at the 2-position of the indole or indene ring. Molecular modeling suggests that this 2' methyl group is an important determinant of the ability of indomethacin and sulindac sulfide to bind tightly to COX enzymes and, thereby, inhibit their function. This hypothesis has been verified by site-directed mutagenesis of the COX-2 enzyme and by synthesis of indomethacin and sulindac sulfide derivatives that lack the 2' methyl group (2-Des-methyl derivatives) as described herein. These derivatives are poor inhibitors of both COX enzymes compared to the parent drugs.

The inability of 2-Des-methyl derivatives of indole acetic acids and indene acetic acids to inhibit COX enzymes provides a strategy to develop drugs that display COX-independent effects but minimally inhibit COX enzymes and, therefore, have a higher safety margin by virtue of reduced gastrointestinal toxicity. This enables higher doses of these drugs to be given, which should increase their efficacy at non-COX targets. These compounds would be expected to exhibit the ability to prevent, treat, or inhibit cancer, neurodegenerative diseases, and diabetes inter alia.

II. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

Following long-standing patent law convention, the terms "a", "an", and "the" refer to "one or more" when used in this application, including the claims. Thus, for example, reference to "a vector" includes a plurality of such vectors, and so forth.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the terms "amino acid" and "amino acid residue" are used interchangeably and mean any of the twenty naturally occurring amino acids. An amino acid is formed upon chemical digestion (hydrolysis) of a polypeptide at its peptide linkages. The amino acid residues described herein are in some embodiments in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented hereinabove.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

In certain instances herein, amino acids are indicated by a one- or three-letter code followed by a number (for example, Val-349). As used herein, this numbering system refer to the positions of corresponding amino acids in ovine COX-1, the amino acid sequence of which can be found at GENBANK® Accession No. P05979. As a result of this convention, a given amino acid and number combination might not be found in a given polypeptide, depending on the particular COX enzyme and species. For example, "Val-349" refers to the valine residue that forms part of the binding pocket for the 2'-methyl group of indomethacin or sulindac. Looking at GENBANK® Accession No. P05979, one can find a valine at position 349. However, when looking at GENBANK® Accession No. Q05769, which is the mouse COX-2 amino acid sequence, one finds that the corresponding valine is not at amino acid 349, but rather at amino acid 335. Similarly, Ala-527, Ser- 530, and Leu-531 refer not only to amino acids at positions 527, 530, and 531 of ovine COX-1, respectively, but also to alanine, serine, and leucine residues found in mouse COX-2 at positions 513, 516, and 517, respectively. The human COX-2 amino acid sequence can be found at GENBANK® Accession No. P35354, and in human COX-2, Val-349, Ala-527, Ser-530, and Leu-531 also refer to the valine, alanine, serine, and leucine amino acids that are present at amino acids 335, 513, 516, and 517, respectively.

As used herein, the term "cell" refers not only to the particular subject cell (e.g., a living biological cell), but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the term "enzyme activity" refers to the ability of an enzyme to catalyze the conversion of a substrate into a product. A substrate for the enzyme can comprise the natural substrate of the enzyme but also can comprise analogues of the natural substrate, which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme can also be measured by determining the amount of an unused co-factor of the reaction remaining in the reaction mixture after a certain period of time or by determining the amount of used co-factor in the reaction mixture after a certain period of time. The activity of the enzyme can also be measured by determining the amount of a donor of free energy or energy-rich molecule (e.g., ATP, phosphoenolpyruvate, acetyl phosphate, or phosphocreatine) remaining in the reaction mixture after a certain period of time or by determining the amount of a used donor of free energy or energy-rich molecule (e.g., ADP, pyruvate, acetate, or creatine) in the reaction mixture after a certain period of time.

As used herein, the term "inhibitor" refers to a chemical substance that inactivates or decreases the biological activity of a polypeptide such as a biosynthetic and catalytic activity, receptor, signal transduction polypeptide, structural gene product, or transport polypeptide.

As used herein, the term "interact" includes "binding" interactions and "associations" between molecules. Interactions can be, for example, protein-protein, protein-small molecule, protein-nucleic acid, and nucleic acid-nucleic acid in nature.

As used herein, the term "modulate" refers to an increase, decrease, or other alteration of any, or all, chemical and biological activities or properties of a biochemical entity, e.g., a wild type or mutant polypeptide. As such, the term "modulate" can refer to a change in the expression level of a gene (or a level of RNA molecule or equivalent RNA molecules encoding one or more proteins or protein subunits), or of an activity of one or more proteins or protein subunits, such that expression, level, or activity is greater than or less than that observed in the absence of the modulator. For example, the term "modulate" can mean "inhibit" or "suppress", but the use of the word "modulate" is not limited to this definition.

The term "modulation" as used herein refers to both upregulation (i.e., activation or stimulation) and downregulation (i.e., inhibition or suppression) of a response. Thus, the term "modulation", when used in reference to a functional property or biological activity or process (e.g., enzyme activity or receptor binding), refers to the capacity to upregulate (e.g., activate or stimulate), downregulate (e.g., inhibit or suppress), or otherwise change a quality of such property, activity, or process. In certain instances, such regulation can be contingent on the occurrence of a specific event, such as activation of a signal transduction pathway, and/or can be manifest only in particular cell types.

The term "modulator" refers to a polypeptide, nucleic acid, macromolecule, complex, molecule, small molecule, compound, species, or the like (naturally occurring or non-naturally occurring) that can be capable of causing modulation. Modulators can be evaluated for potential activity as inhibitors or activators (directly or indirectly) of a functional property, biological activity or process, or a combination thereof, (e.g., agonist, partial antagonist, partial agonist, inverse agonist, antagonist, anti-microbial agents, inhibitors of microbial infection or proliferation, and the like) by inclusion in assays. In such assays, many modulators can be screened at one time. The activity of a modulator can be known, unknown, or partially known.

Modulators can be either selective or non-selective. As used herein, the term "selective" when used in the context of a modulator (e.g., an inhibitor) refers to a measurable or otherwise biologically relevant difference in the way the modulator interacts with one molecule (e.g., an enzyme or receptor) versus another similar but not identical molecule (e.g., a member of the same enzyme or receptor family).

It must be understood that it is not required that the degree to which the interactions differ be completely opposite. Put another way, the term selective modulator encompasses not only those molecules that only bind to a given polypeptide and not to related family members. The term is also intended to include modulators that are characterized by interactions with polypeptides of interest and from related family members that differ to a lesser degree. For example, selective modulators include modulators for which conditions can be found (such as the nature of the substituents present on the modulator) that would allow a biologically relevant difference in the binding of the modulator to the polypeptide of interest versus polypeptides derived from different family members.

When a selective modulator is identified, the modulator will bind to one molecule (for example a polypeptide of interest) in a manner that is different (for example, stronger) than it binds to another molecule (for example, a polypeptide related to the polypeptide of interest). As used herein, the modulator is said to display "selective binding" or "preferential binding" to the molecule to which it binds more strongly.

As used herein, the term "mutation" carries its traditional connotation and means a change, inherited, naturally occurring or introduced, in a nucleic acid or polypeptide sequence, and is used in its sense as generally known to those of skill in the art.

As used herein, the terms "nucleic acid" and "nucleic acid molecule" mean any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally-occurring nucleotides), or a combination of both. Nucleic acids can be either single stranded or double stranded.

As used herein, the term "polypeptide" means any polymer comprising any of the 20 protein amino acids, or amino acid analogs, regardless of its size or function. Although "protein"

is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably. The term "polypeptide" encompasses proteins of all functions, including enzymes.

As used herein, the terms "polypeptides of interest" and "target polypeptide" are used interchangeably to refer to a polypeptide the activity of which the compositions and methods of the presently disclosed subject matter are intended to modulate. For example, polypeptides of interest include, but are not limited to cyclooxygenase enzymes, PPARs (e.g., PPARγ), and secretases (e.g., γ-secretase). The compositions disclosed herein are intended to differentially modulate these enzymes relative to one or more of the others. For example, the NSAID derivatives disclosed herein are intended to have reduced cyclooxygenase-binding activities, while their binding activities to other polypeptides might or might not be affected by the derivitization. While not wishing to be limited to any particular theory of operation, the reduction in COX-binding activity might enhance the bioavailability of these derivatives to other, non-COX polypeptides of interest because the derivatives either do not bind to COX enzymes or bind to COX enzymes to a lesser degree than do the non-derivatized NSAIDs upon which they are based.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in another example less than 0.01, in another example less than 0.005, and in yet another example less than 0.001, are regarded as significant.

As used herein, the term "significant increase" refers to an increase in activity (for example, enzymatic activity) that is larger than the margin of error inherent in the measurement technique, in some embodiments an increase by about 2 fold or greater over a baseline activity (for example, the activity of the wild type enzyme in the presence of the inhibitor), in some embodiments an increase by about 5 fold or greater, and in still some embodiments an increase by about 10 fold or greater.

With respect to the binding of one or more molecules (for example, a modulator) to one or more polypeptides (for example, a PPAR, a COX, or a secretase), a significant increase can also refer to: (a) a biologically relevant difference in binding of two or more related compounds to the same polypeptide; and/or (b) a biologically relevant difference in binding of the same compound to two different polypeptides. In this aspect, "significant" is to be thought of in its ordinary meaning: namely, a difference between two occurrences that is important (i.e., biologically or medically relevant). By way of example, a significant increase can also refer to an increase in the amount of a derivative of an NSAID (for example, a 2-Des-methyl derivative of the presently disclosed subject matter) that interacts with a non-COX polypeptide (for example, a PPARγ or a γ-secretase) per unit dose of the derivative administered as compared to the amount of the non-derivatized NSAID that interacts with the same non-COX polypeptide per unit dose of the non-derivatized NSAID. In this example, because the derivative binds to COX enzymes less strongly than the parent NSAID, on a mole-for-mole basis, more of the derivative should be available to interact with non-COX polypeptides than would the parent NSAID.

As used herein, the terms "significantly less" and "significantly reduced" refer to a result (for example, an amount of a product of an enzymatic reaction) that is reduced by more than the margin of error inherent in the measurement technique, in some embodiments a decrease by about 2 fold or greater with respect to a baseline activity (for example, the activity of the wild type enzyme in the absence of the inhibitor), in some embodiments, a decrease by about 5 fold or greater, and in still some embodiments a decrease by about 10 fold or greater.

As used herein, the phrases "treatment effective amount", "therapeutically effective amount", and "treatment amount" are used interchangeably and refer to an amount of a therapeutic composition sufficient to produce a measurable response (e.g., a biologically or clinically relevant response in a subject being treated). Actual dosage levels of active ingredients in the pharmaceutical compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate modulator of the presently disclosed subject matter and adjust the therapeutic regimen accordingly.

After review of the disclosure herein of the presently disclosed subject matter, one of ordinary skill in the art can tailor the dosages to an individual subject, taking into account the particular formulation, method of administration to be used with the composition, and other factors. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

III. DERIVATIZATION OF NSAIDs

III.A. General Considerations

Cyclooxygenases (COXs) are the therapeutic targets of non-steroidal anti-inflammatory drugs. Indomethacin (INDO) was one of the first non-steroidal anti-inflammatory drugs to be characterized as a functionally irreversible, time-dependent inhibitor, but the molecular basis underlying this phenomenon is uncertain. In the crystal structure of INDO bound to COX-2, a small hydrophobic pocket was identified that surrounds the 2' methyl group of INDO. The pocket is formed by the residues Ala-527, Val-349, Ser-530, and Leu-531. The contribution of this pocket to inhibition was evalu ated by altering its volume by mutagenesis of Val-349. The V349A mutation expanded the pocket and increased the potency of INDO, whereas the V349L mutation reduced the size of the pocket and decreased the potency of INDO. Particularly striking was the reversibility of INDO inhibition of the V349L mutant.

NSAIDs have been found to have various activities, including the ability to modulate the activities of cyclooxygenases (e.g., COX-1 and/or COX-2), PPARs (e.g., PPARγ), and secretases (e.g., γ-secretase). The ability to create different derivatives of NSAIDs can be exploited to differentially modulate the activities of these polypeptides, which can be used to treat different diseases and disorders.

The use of an NSAID to modulate a PPAR and/or a secretase in vivo is compromised by the presence of significant gastrointestinal toxicities induced by high dosage administration of the NSAID. This effect appears to be due to the inhibition of COX-1, resulting in a reduction in the production and release of cytoprotective prostaglandins in the gastrointestinal (GI) tract. One approach to reducing GI toxicity is to reduce the ability of the NSAID to bind to COX-1 and/or COX-2, yet maintain the ability to modulate other target polypeptides.

Thus, in some embodiments, the presently disclosed subject matter provides a method for altering the specificity of a cyclooxygenase-inhibiting compound. In some embodiments, the method comprises (a) providing a compound having cyclooxygenase inhibitory activity, the compound comprising an indoleacetic acid or indenacetic acid functional group having a 2' methyl group; and (b) replacing the 2' methyl group with a moiety selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl to create a derivative, wherein the derivative substantially lacks cyclooxygenase inhibitory activity. In some embodiments of this method, the compound is a non-steroidal anti-inflammatory drug. Thus, in some embodiments, the derivative is a derivative of an NSAID, and comprises an indoleacetic acid or indeneacetic acid functional group having a hydrogen or a fluorine substituent at the 2' position. Representative NSAIDs comprising an indoleacetic acid or indenacetic acid functional group include, but are not limited to indomethacin and sulindac, as well as pharmaceutically acceptable salts thereof and combinations thereof.

The structures of indomethacin and sulindac are presented below.

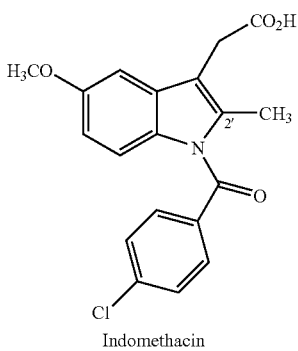
Indomethacin

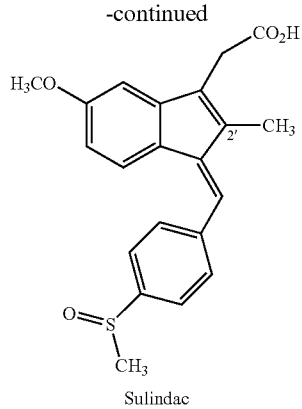
Sulindac

The 2' methyl groups are shown attached to the indoleacetic acid and indenacetic acid functional groups, respectively. These 2' methyl groups play an important role in binding of these NSAIDs to COX enzymes, and thus removal of the 2' methyl groups to form 2-Des-methyl derivatives can be used to reduce the ability of the 2-Des-methyl derivatives to bind to COX enzymes without negatively affecting the ability of the derivatives to bind to and/or interact with PPARs, secretases, and other target polypeptides. Accordingly, in some embodiments, the derivative is selected from the group consisting of 2-Des-methylindomethacin, eindenic acid sulfide, eindenic acid sulfoxide, and eindenic acid sulfone. In some embodiments, the derivative is eindenic acid sulfide.

Additionally, all positions corresponding to positions where hydrogen is present in the parent compounds can also be derivatized, and should be viewed as R groups (e.g., $R^1$, $R^2$, $R^3$, etc.). As such, in some embodiments a generic structure for the presently disclosed derivatives is presented as Formula I:

Formula I

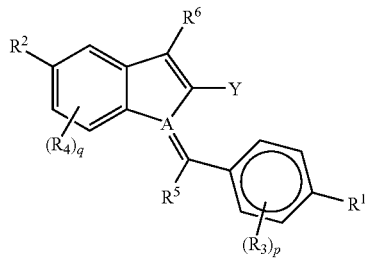

wherein
$R^1$ is selected from the group consisting of hydrogen, halo, $CF_3$; $SCH_3$; $SOCH_3$; $SO_2CH_3$; $SO_2NH_2$; $C_1$ to $C_6$ alkyl, branched alkyl, or substituted alkyl; $C_1$ to $C_6$ alkoxy, branched alkoxy, or substituted alkoxy; $C_1$ to $C_6$ alkylcarboxylic acid, branched alkylcarboxylic acid, or substituted alkylcarboxylic acid; and $CH_2N_3$;
$R^2$ is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;
$R^3$ and $R^4$ are each independently selected from the group consisting of hydrogen; halo; $CF_3$; $C_1$ to $C_6$ alkyl, branched alkyl, or substituted alkyl; $C_1$ to $C_6$ alkoxy, branched alkoxy, or substituted alkoxy; aryl; substituted aryl; benzyloxy; SCH$_3$; SOCH$_3$; SO$_2$CH$_3$; and SO$_2$NH$_2$;

R$^5$ is selected from the group consisting of hydrogen, C$_1$ to C$_6$ alkyl, branched alkyl, or substituted alkyl, and =O;

R$^6$ is selected from the group consisting of hydrogen; C$_1$ to C$_6$ alkyl, branched alkyl, or substituted alkyl; C$_1$ to C$_6$ alkoxy, branched alkoxy, or substituted alkoxy; benzyloxy; C$_1$ to C$_6$ alkylcarboxylic acid, branched alkylcarboxylic acid, or substituted alkylcarboxylic acid; and the following structure:

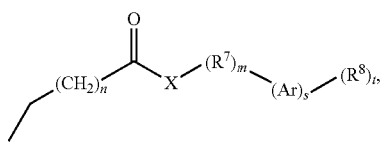

wherein
Ar is cyclohexyl or phenyl;
R$^7$ is hydrogen; C$_1$ to C$_6$ alkyl, branched alkyl, or substituted alkyl;
R$^8$ is hydrogen, halo, C$_1$ to C$_6$ alkyl, branched alkyl, and substituted alkyl; C$_1$ to C$_6$ alkoxy, branched alkoxy, and substituted alkoxy; C$_1$ to C$_6$ alkylcarboxylic acid, branched alkylcarboxylic acid, or substituted alkylcarboxylic acid; amino; nitro; CF$_3$; bromoacetamidyl; benzoyl; or 2-phenyl-oxiranyl;
X is O or NR$^9$, wherein R$^9$ is hydrogen or alkyl; and
m, n, s, and t are each individually 0, 1, 2, 3, 4, or 5;
Y is selected from the group consisting of hydrogen, halo, CF$_3$, and C$_2$ to C$_6$ alkyl, branched alkyl, or substituted alkyl;
A is selected from the group consisting of carbon and nitrogen;
p and q are both individually 0, 1, 2, 3, or 4;
the bond between the carbon bound to R$^5$ and the indene ring and is a single bond or a double bond; and
the six-membered ring to which R$^1$ is bound is cyclohexyl or phenyl.

Continuing with reference to Formula I, in some embodiments, R$^1$ is selected from the group consisting of halo, C$_1$ to C$_6$ alkyl or branched alkyl, SCH$_3$, SOCH$_3$, SO$_2$CH$_3$, and SO$_2$NH$_2$; R$^2$ is selected from the group consisting of hydrogen; halo; C$_1$ to C$_6$ alkyl or branched alkyl; C$_1$ to C$_6$ alkoxy or branched alkoxy; benzyloxy; SCH$_3$; SOCH$_3$; SO$_2$CH$_3$; SO$_2$NH$_2$; and CONH$_2$; R$^3$ and R$^4$ are each independently selected from the group consisting of hydrogen, C$_1$ to C$_6$ alkyl or branched alkyl, and halo; R$^5$ is selected from the group consisting of hydrogen, C$_1$ to C$_6$ alkyl or branched alkyl, and carbonyl; R$^6$ is selected from the group consisting of C$_1$ to C$_6$ alkylcarboxylic acid and branched C$_1$ to C$_6$ alkylcarboxylic acid; Y is selected from the group consisting of hydrogen, halo, and C$_2$ to C$_6$ alkyl or branched alkyl; A is selected from the group consisting of carbon and nitrogen; and the bond between the carbon bound to R$^5$ and the indene ring is a single bond or a double bond.

In some embodiments, a generic structure for the presently disclosed derivatives is presented as Formula Ia or Formula Ib:

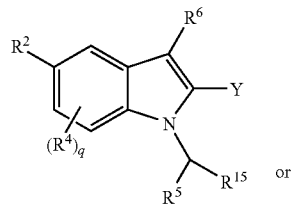
Formula Ia

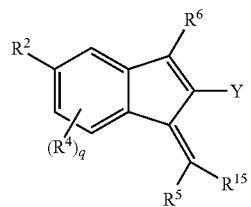
Formula Ib wherein:
R$^2$ is selected from the group consisting of hydrogen, halo, CF$_3$; SCH$_3$; SOCH$_3$; SO$_2$CH$_3$; SO$_2$NH$_2$; CONH$_2$; C$_1$ to C$_6$ alkyl, branched alkyl, or substituted alkyl; C$_1$ to C$_6$ alkoxy, branched alkoxy, or substituted alkoxy; benzyloxy; C$_1$ to C$_6$ alkylcarboxylic acid, branched alkylcarboxylic acid, or substituted alkylcarboxylic acid; and CH$_2$N$_3$;

R$^4$ is selected from the group consisting of hydrogen; halo; CF$_3$; C$_1$ to C$_6$ alkyl, branched alkyl, or substituted alkyl; C$_1$ to C$_6$ alkoxy, branched alkoxy, or substituted alkoxy; aryl; substituted aryl; benzyloxy; SCH$_3$; SOCH$_3$; SO$_2$CH$_3$; and SO$_2$NH$_2$;

R$^5$ is selected from the group consisting of hydrogen, C$_1$ to C$_6$ alkyl, C$_1$ to C$_6$ branched alkyl, and C$_1$ to C$_6$ substituted alkyl, and in the case of Formula Ia, =O;

R$^6$ is selected from the group consisting of hydrogen; C$_1$ to C$_6$ alkyl, branched alkyl, or substituted alkyl; C$_1$ to C$_6$ alkoxy, branched alkoxy, or substituted alkoxy; benzyloxy; C$_1$ to C$_6$ alkylcarboxylic acid, branched alkylcarboxylic acid, or substituted alkylcarboxylic acid; and the following structure:

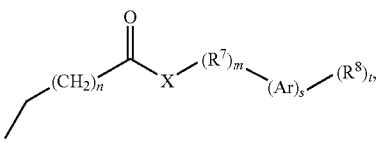

wherein
Ar is cyclohexyl or phenyl;
R$^7$ is hydrogen; C$_1$ to C$_6$ alkyl, branched alkyl, or substituted alkyl;
R$^8$ is hydrogen, halo, C$_1$ to C$_6$ alkyl, branched alkyl, and substituted alkyl; C$_1$ to C$_6$ alkoxy, branched alkoxy, and substituted alkoxy; C$_1$ to C$_6$ alkylcarboxylic acid, branched alkylcarboxylic acid, or substituted alkylcarboxylic acid; amino; nitro; CF$_3$; bromoacetamidyl; benzoyl; or 2-phenyl-oxiranyl;
X is O or NR$^9$, wherein R$^9$ is hydrogen or alkyl; and
m, n, and t are each individually 0, 1, 2, 3, 4, or 5;

R$^{15}$ is selected from the group consisting of cyclohexyl and an aromatic substituent, wherein the aromatic substituent comprises an aryl, a heteroaryl, and singly or multiply substituted derivatives thereof;

Y is selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl; and
q is 0, 1, 2, 3, or 4.

In some embodiments, $R^{15}$ comprises an aryl comprising multiple aromatic rings that are fused together or covalently linked. In some embodiments, the multiple aromatic rings are covalently linked by a moiety selected from the group consisting of an alkylene moiety, a carbonyl, oxygen, diphenylether, and nitrogen. In some embodiments, the multiple aromatic rings are selected from the group consisting of naphthyl, biphenyl, diphenylether, diphenylamine, and benzophenone.

In some embodiments, the derivative is selected from the group consisting of 2-Des-methylindomethacin, eindenic acid sulfide, eindenic acid sulfoxide, and eindenic acid sulfone. In some embodiments, the derivative is eindenic acid sulfide.

In some embodiments, the compound is a compound of Formula Ib, wherein:
  $R^2$ is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;
  $R^4$ is selected from the group consisting of hydrogen; halo; $CF_3$; $C_1$ to $C_6$ alkyl, branched alkyl, or substituted alkyl; $C_1$ to $C_6$ alkoxy, branched alkoxy, or substituted alkoxy; aryl; substituted aryl; benzyloxy; $SCH_3$; $SOCH_3$; $SO_2CH_3$; and $SO_2NH_2$;
  $R^5$ is selected from the group consisting of hydrogen, $C_1$ to $C_6$ alkyl, $C_1$ to $C_6$ branched alkyl, and $C_1$ to $C_6$ substituted alkyl;
  $R^6$ is selected from the group consisting of $C_1$ to $C_6$ alkylcarboxylic acid, branched alkylcarboxylic acid, and substituted alkylcarboxylic acid;
  $R^{15}$ is selected from the group consisting of cyclohexyl and an aromatic substituent, wherein the aromatic substituent comprises an aryl, a heteroaryl, and singly or multiply substituted derivatives thereof;
  Y is selected from the group consisting of hydrogen; halo; halomethyl, wherein at least one hydrogen of the methyl group is substituted with a halogen; $C_2$ to $C_6$ alkyl; $C_2$ to $C_6$ branched alkyl; and $C_2$ to $C_6$ substituted alkyl; and
  q is 0, 1, 2, 3, or 4.

In some embodiments, $R^{15}$ comprises an aryl comprising multiple aromatic rings that are fused together or covalently linked. In some embodiments, the multiple aromatic rings are covalently linked by a moiety selected from the group consisting of an alkylene moiety, a carbonyl, oxygen, diphenylether, and nitrogen. In some embodiments, the multiple aromatic rings are selected from the group consisting of naphthyl, biphenyl, diphenylether, diphenylamine, and benzophenone.

In some embodiments, $R^2$ is selected from the group consisting of halo, $C_1$ to $C_6$ alkyl or branched alkyl, $SCH_3$, $SOCH_3$, $SO_2CH_3$, and $SO_2NH_2$. In some embodiments, $R^2$ is F.

In some embodiments, $R^{15}$ is in the E orientation with respect to the indene ring. In some embodiments, $R^{15}$ can be selected from the group including, but not limited to:

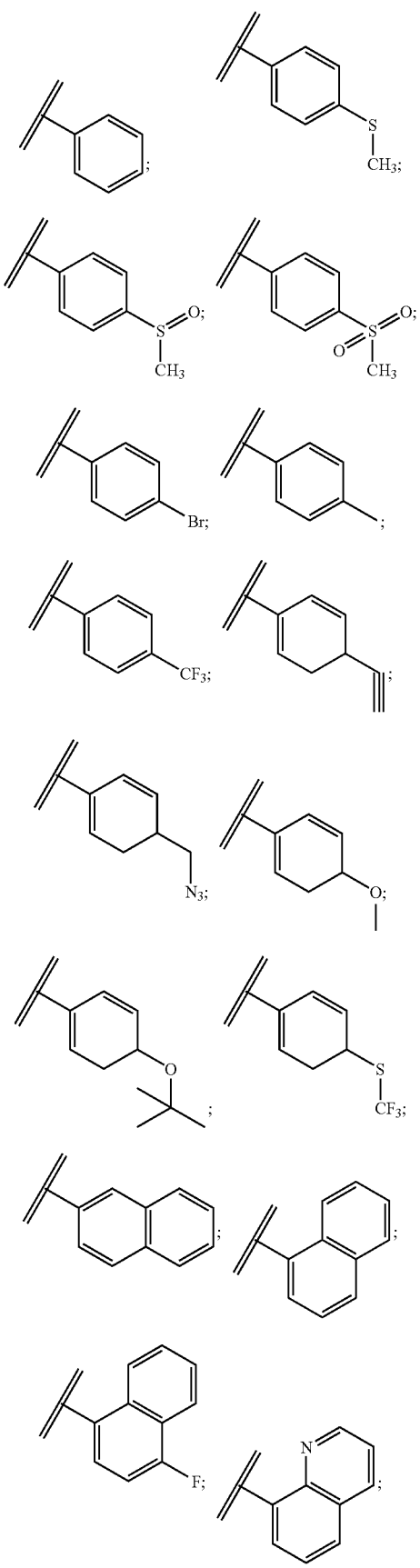

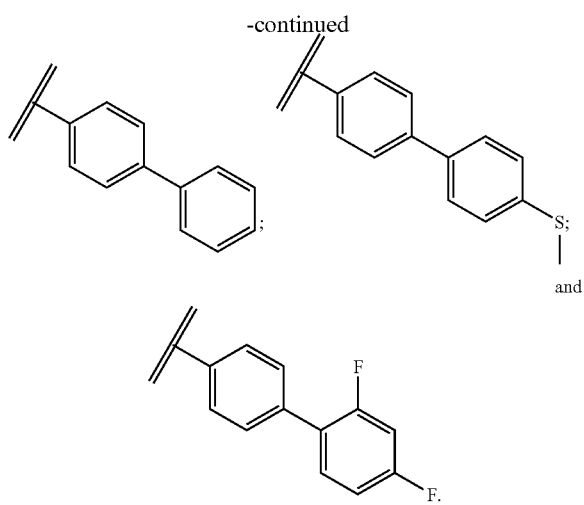

In derivatizing the R groups, each R group can be independently selected, such that any number of R groups (i.e., from zero R groups to all R groups present in a structure) can be derivatized. The term "independently selected" is used herein to indicate that the R groups, e.g., $R^1$, $R^2$, $R^3$, etc. can be identical or different (e.g., $R^1$, $R^2$ and $R^3$ can all be substituted alkyls, or $R^1$ and $R^4$ can be a substituted alkyl and $R^3$ can be an aryl, etc.). Moreover, "independently selected" means that in a multiplicity of R groups with the same name, each group can be identical to or different from each other (e.g., one $R^3$ can be an alkyl, while another $R^3$ group in the same compound can be aryl; one $R^4$ group can be H, while another $R^4$ group in the same compound can be alkyl, etc.).

A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

As used herein, the term "alkyl" means $C_{1-10}$ inclusive (i.e., carbon chains comprising 1, 2, 3, 4, 5, 6, 7, 8, 9, or 10 carbon atoms; also, in some embodiments, $C_{1-6}$ inclusive) linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, ethenyl, propenyl, butenyl, pentenyl, hexenyl, butadienyl, propynyl, butynyl, pentynyl, hexynyl, and allenyl groups.

The alkyl group can be optionally substituted with one or more alkyl group substituents which can be the same or different, where "alkyl group substituent" includes alkyl, halo, aryl, arylamino, acyl, hydroxy, aryloxy, alkoxyl, alkylthio, arylthio, aralkyloxy, aralkylthio, carboxy, alkoxycarbonyl, oxo and cycloalkyl. In this case, the alkyl can be referred to as a "substituted alkyl". Representative substituted alkyls include, for example, benzyl, trifluoromethyl, and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. Thus, the term "alkyl" can also include esters and amides. "Branched" refers to an alkyl group in which an alkyl group, such as methyl, ethyl, or propyl, is attached to a linear alkyl chain.

The term "aryl" is used herein to refer to an aromatic substituent, which can be a single aromatic ring or multiple aromatic rings that are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine, and benzophenone among others. In particular embodiments, the term "aryl" means a cyclic aromatic comprising about 5 to about 10 carbon atoms, including 5 and 6-membered hydrocarbon and heterocyclic aromatic rings. As used herein, the term "aryl" also encompasses "heteroaryl" (i.e., aryl groups containing ring atoms other than carbon). Also, the term "aryl" can also included esters and amides related to the underlying aryl group.

An aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl. In this case, the aryl can be referred to as a "substituted aryl".

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the $-OZ^1$ radical, where $Z^1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy, and the like.

The term "amino" is used herein to refer to the group $-NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group can be represented as $-N^+Z^1Z^2Z^3$, with the previous definitions applying and $Z^3$ being either H or alkyl.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Aroyl" means an aryl-CO— group wherein aryl is as previously described. Exemplary aroyl groups include benzoyl and 1- and 2-naphthoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur, or substituted or unsubstituted nitrogen atoms, wherein the nitrogen substituent is hydrogen, lower alkyl, or aryl, thus providing a heterocyclic group. Representative monocyclic cycloalkyl rings include cyclopropyl, cyclobutyl, cyclopentyl, cyclohexyl, and cycloheptyl. Multicyclic cycloalkyl rings include adamantyl, octahydronaphthyl, decalin, camphor, camphane, and noradamantyl.

"Aralkyl" refers to an aryl-alkyl-group wherein aryl and alkyl are as previously described. Exemplary aralkyl groups include benzyl, phenylethyl, and naphthylmethyl. Similarly, the term "alkylaryl" refers to an alkyl-aryl-group, wherein aryl and alkyl are as previously described. As such, the terms "aralkyl" and "alkylaryl" can be used interchangeably, although in some instances the use of one term versus the other is intended to express the order of a group in a chemical structure when read from left-to-right. By way of example, an "ethylphenyl" substituent might be distinguished from a "phenylethyl" substituent in that in the former case, the ethyl moiety is bound to the main body of the molecule while in the latter it would be the phenyl moiety that is bound to the main body of the molecule.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl as previously described.

"Dialkylcarbamoyl" refers to a R'RN—CO— group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "halomethyl" refers to a methyl group wherein at least one hydrogen has been substituted with a halogen.

The term "hydroxyl" refers to the —OH group.

The term "hydroxyalkyl" refers to an alkyl group substituted with an —OH group.

The term "mercapto" refers to the —SH group.

The term "nitro" refers to the —$NO_2$ group.

The term "oxo" refers to a compound described previously herein wherein a carbon atom is replaced by an oxygen atom.

The term "thio" refers to a compound described previously herein wherein a carbon or oxygen atom is replaced by a sulfur atom.

The term "sulfate" refers to the —$SO_4$ group.

A "heteroatom", as used herein, is an atom other than carbon. Exemplary heteroatoms are heteroatoms selected from the group consisting of N, O, P, S, Si, B, Ge, Sn, and Se. In some embodiments, a heteroatom is N. In some embodiments a heteroatom is O. In some embodiments, a heteroatom is S.

As shown in Formula I, "A" depicts a carbon or a nitrogen.

A dashed line representing a bond in a structure indicates that the bond can either be present or absent in the structure. Thus, the dashed bond in Formula I that links the A atom to the carbon atom to which $R^5$ binds indicates that this bond can be a single bond or a double bond. The same is true for the dashed bond depicted inside the six-membered ring to which $R^1$ is bound in Formula I. For the six-membered ring, the individual bonds can all be single, double, or a mixture of the two (e.g., the six-membered ring could be a cyclohexane ring, a benzene ring, or a ring with any combination of single and/or double bonds).

As used herein, the term "eindenic acid" refers to the following structure:

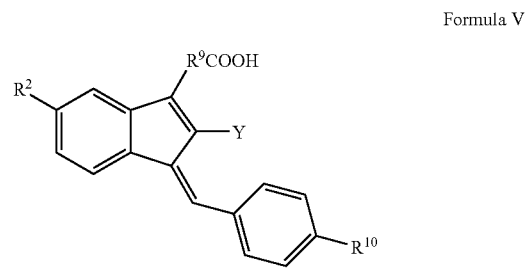

Formula V

Compounds having the general structure of eindenic acid as depicted in Formula V can be generated by 2'-desmethylation of sulindac, sulindac sulfide, etc. While the present co-inventors do not wish to be restricted to any particular theory of operation, they have observed that the double bond of the p-substituted benzylidene moiety, which is in a Z-orientation in sulindac, can adopt an E-orientation when the 2'-methyl group of sulindac is modified to a hydrogen or a fluorine. Thus, the term "eindenic acid" refers to an "E form indenacetic acid" to reflect the fact that in some embodiments this double bond is in the E-orientation. However and as indicated hereinabove, each chemical formula or name disclosed herein encompasses all optical isomers and stereoisomers, as well as racemic mixtures where such isomers and mixtures exist. Thus, eindenic acids can adopt either the E-orientation or the Z-orientation. In some embodiments, $R^2$ and Y are defined as before and $R^9$ and $R^{10}$ are each independently selected from the group consisting of $C_1$ to $C_6$ alkyl, $C_1$ to $C_6$ branched alkyl, and substituted (for example, halogen-substituted) or unsubstituted aryl.

In addition to modification of the 2' methyl position, several NSAIDs have carboxylic acid groups that can be modified. In some embodiments, the carboxylic acid moiety of indomethacin or sulindac is derivatized to an amide. In some embodiments, an amide derivative has the following general formula:

Formula II

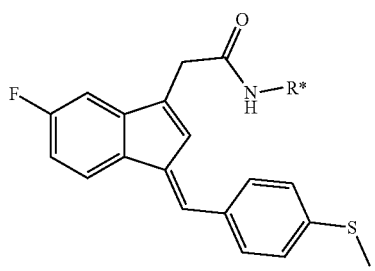

In some embodiments, R* is selected from the group consisting of aryl, alkylaryl, branched alkylaryl, and substituted aryl, wherein the substituted aryl comprises one or more substituents selected from the group consisting of halo, amino, nitro, alkoxy, hydroxyl, $CF_3$, haloacetamidyl (e.g. bromoacetamidyl), benzoyl, and 2-phenyl-oxiranyl. In some embodiments, the amide derivative has the following general formula:

Formula III

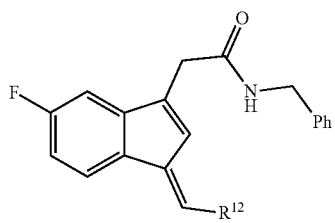

wherein $R^{12}$ is selected from the group consisting of phenyl-$SOCH_3$, phenyl-$SO_2CH_3$, phenyl, phenyl methyl ester, phenyl-COOH, phenyl-halo, and $C_3$ to $C_6$ cycloalkyl. Representative amide derivatives are presented in Table 1.

TABLE 1

Representative Amide Derivatives

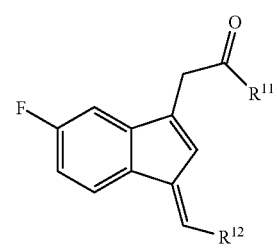

| Compound | $R^{11}$ | $R^{12}$ |
|---|---|---|
| 2 | 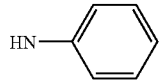 | 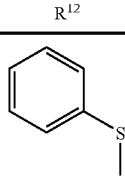 |
| 3 | 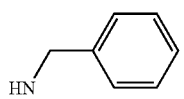 | 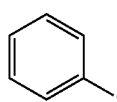 |

TABLE 1-continued

Representative Amide Derivatives

| Compound | $R^{11}$ | $R^{12}$ |
|---|---|---|
| 4 | 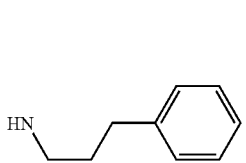 | 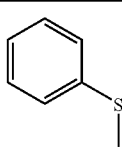 |
| 5 | 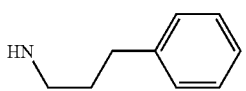 | 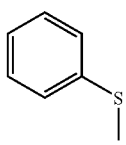 |
| 6 | 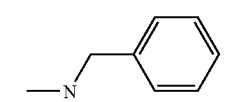 | 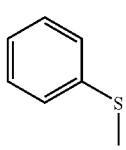 |
| 7 | 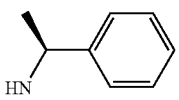 | 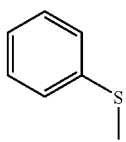 |
| 8 | 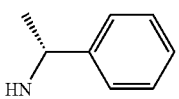 | 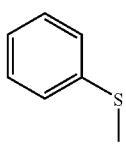 |
| 9 | 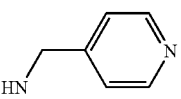 | 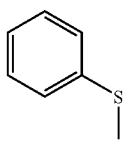 |
| 10 | 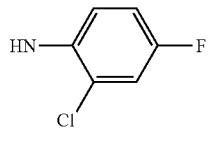 | 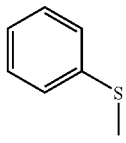 |
| 11 | 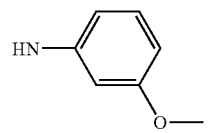 | 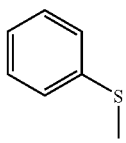 |

TABLE 1-continued

Representative Amide Derivatives

| Compound | R¹¹ | R¹² |
|---|---|---|
| 12 | 4-aminobenzyl-NH- | phenylthio |
| 13 | 3-aminobenzyl-NH- | phenylthio |
| 14 | 2-aminobenzyl-NH- | phenylthio |
| 15 | 4-hydroxybenzyl-NH- | phenylthio |
| 16 | 3-hydroxybenzyl-NH- | phenylthio |
| 17 | 4-methylbenzyl-NH- | phenylthio |
| 18 | 3-methylbenzyl-NH- | phenylthio |
| 19 | 2-methylbenzyl-NH- | phenylthio |
| 20 | 4-chlorobenzyl-NH- | phenylthio |
| 21 | 3-chlorobenzyl-NH- | phenylthio |
| 22 | 4-bromobenzyl-NH- | phenylthio |
| 23 | 3-bromobenzyl-NH- | phenylthio |
| 24 | 4-trifluoromethylbenzyl-NH- | phenylthio |
| 25 | 3-trifluoromethylbenzyl-NH- | phenylthio |
| 26 | 4-nitrobenzyl-NH- | phenylthio |
| 27 | 3-nitrobenzyl-NH- | phenylthio |

TABLE 1-continued

Representative Amide Derivatives

[Structure: fluoro-indene with R11 carbonyl and R12 methylidene substituents]

| Compound | R11 | R12 |
|---|---|---|
| 28 | [2-nitrobenzylamino] | [phenyl-SMe] |
| 29 | [4-(bromoacetamido)benzylamino] | [benzyl-N3] |
| 30 | [4-benzoylbenzylamino] | [phenyl-SMe] |
| 31 | [4-(2-phenyloxiranyl)benzylamino] | [benzyl-N3] |
| 32 | [benzylamino] | [phenyl-S(=O)Me] |
| 33 | [benzylamino] | [phenyl-S(=O)2Me] |
| 34 | [benzylamino] | [phenyl] |
| 35 | [benzylamino] | [4-methoxyphenyl] |
| 36 | [benzylamino] | [4-carboxyphenyl-COOH] |
| 37 | [benzylamino] | [4-bromophenyl] |
| 38 | [benzylamino] | [cyclohexyl] |

In some embodiments, a carboxylic acid moiety present on the compound is derivatized to an ester. In some embodiments, the ester derivative has the following general formula:

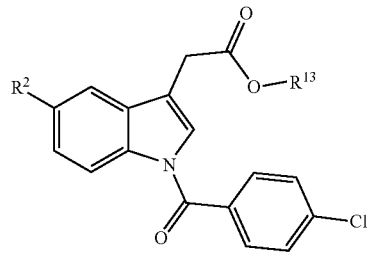

Formula IV wherein $R^2$ is defined as above and $R^{13}$ is defined as in Table 2. In some embodiments, the ester derivative has the following formula:

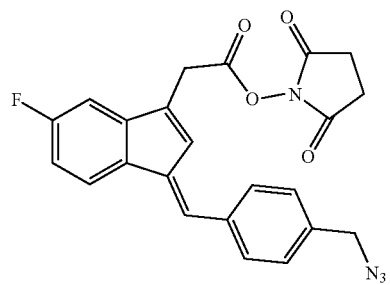

TABLE 2

Representative Ester Derivatives

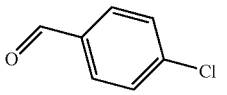

| Compound | $R^2$ | $R^{13}$ | $R^{14}$ |
|---|---|---|---|
| 39 | $SO_2CH_3$ | $CH_2CH_3$ | (4-chlorobenzoyl) |

TABLE 2-continued

Representative Ester Derivatives

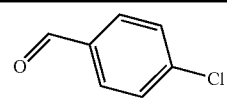

| Compound | $R^2$ | $R^{13}$ | $R^{14}$ |
|---|---|---|---|
| 40 | $OCH_3$ | $CH_3$ | (4-chlorobenzoyl) |

These and other representative derivatives of indomethacin and sulindac are presented in Table 3.

TABLE 3

Representative Derivatives

| Compound No. | Structure | Formula Mol. Wt. |
|---|---|---|
| 1 | 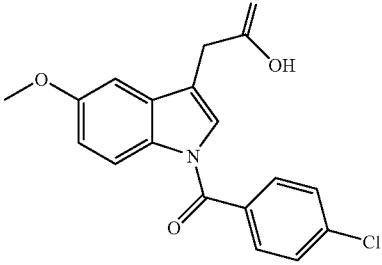 | $C_{18}H_{14}ClNO_4$ 343.76 |
| 2 | 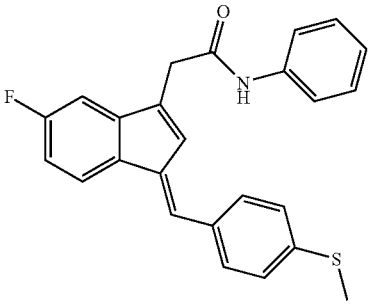 | $C_{25}H_{20}FNOS$ 401.5 |
| 3 | 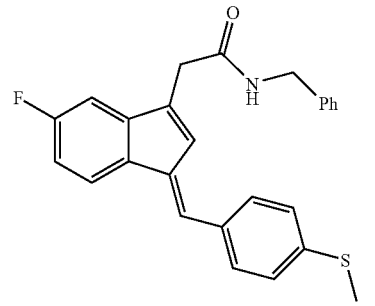 | $C_{26}H_{22}FNOS$ 415.52 |

TABLE 3-continued

Representative Derivatives

| Compound No. | Structure | Formula Mol. Wt. |
|---|---|---|
| 4 | 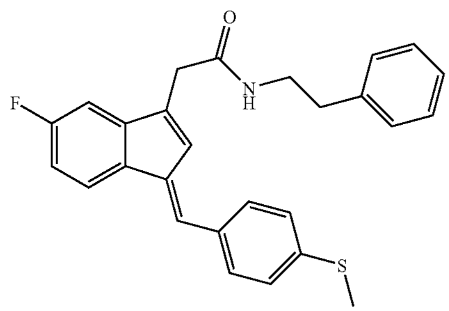 | $C_{27}H_{24}FNOS$ 429.55 |
| 5 | 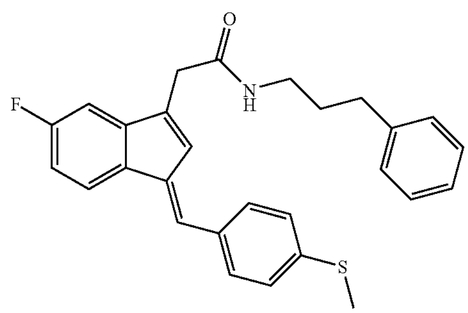 | $C_{28}H_{26}FNOS$ 443.58 |
| 6 | 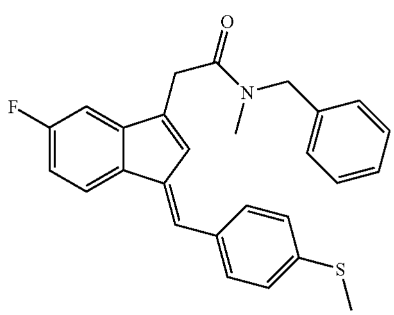 | $C_{27}H_{24}FNOS$ 429.55 |
| 7 | 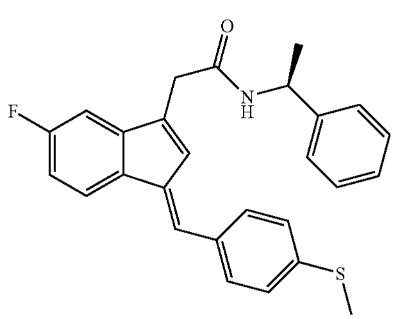 | $C_{27}H_{24}FNOS$ 429.55 |

TABLE 3-continued

Representative Derivatives

| Compound No. | Structure | Formula Mol. Wt. |
|---|---|---|
| 8 | 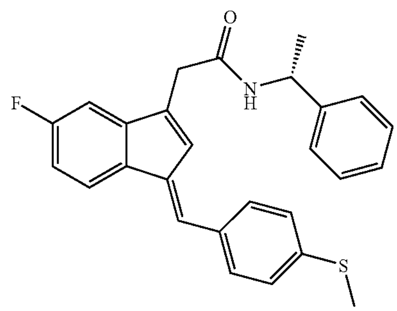 | $C_{27}H_{24}FNOS$ 429.55 |
| 9 | 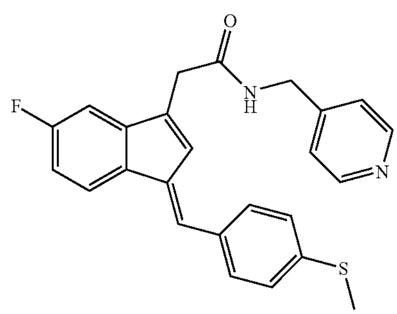 | $C_{25}H_{21}FN_2OS$ 416.51 |
| 10 | 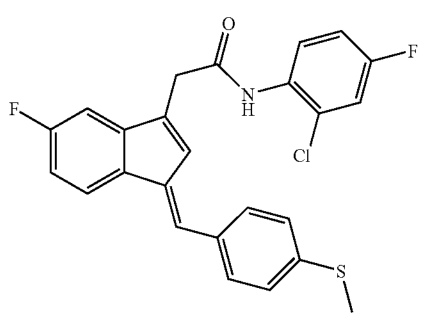 | $C_{25}H_{18}ClF_2NOS$ 453.93 |
| 11 | 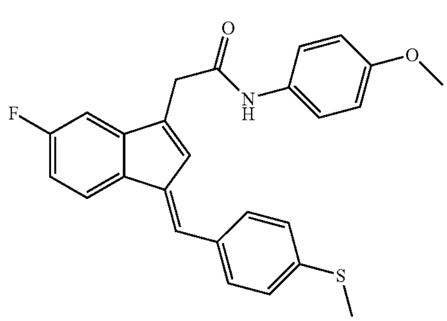 | $C_{26}H_{22}FNO_2S$ 431.52 |

TABLE 3-continued

Representative Derivatives

| Compound No. | Structure | Formula Mol. Wt. |
|---|---|---|
| 12 | 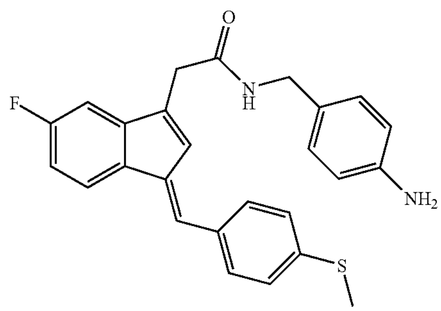 | $C_{26}H_{23}FN_2OS$ 430.54 |
| 13 | 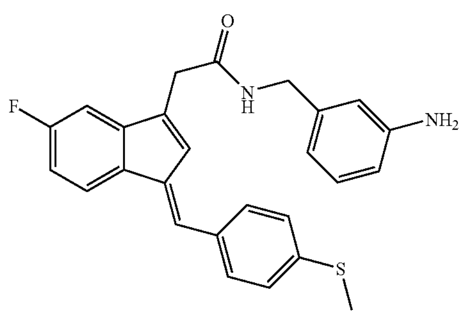 | $C_{26}H_{23}FN_2OS$ 430.54 |
| 14 | 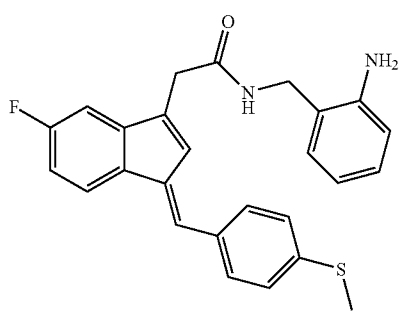 | $C_{26}H_{23}FN_2OS$ 430.54 |
| 15 | 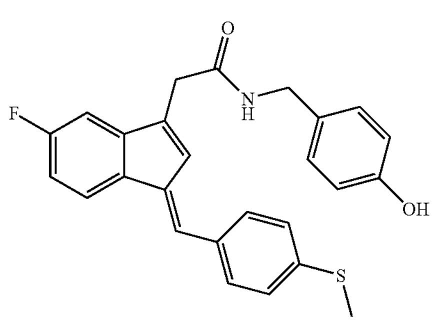 | $C_{26}H_{22}FNO_2S$ 431.52 |

TABLE 3-continued
Representative Derivatives
| Compound No. | Structure | Formula Mol. Wt. |
|---|---|---|
| 16 | 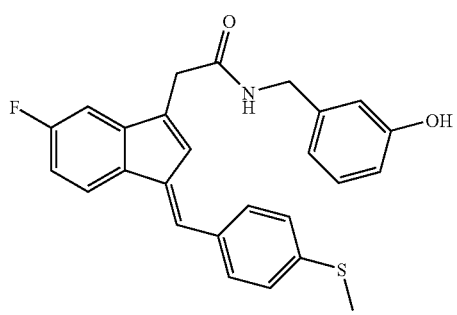 | $C_{26}H_{22}FNO_2S$ 431.52 |
| 17 | 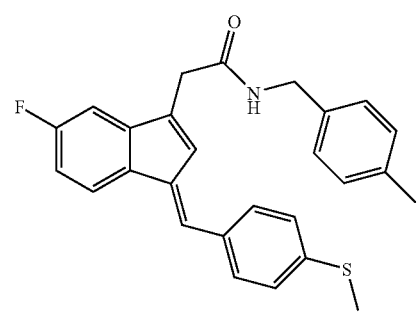 | $C_{27}H_{24}FNOS$ 429.55 |
| 18 | 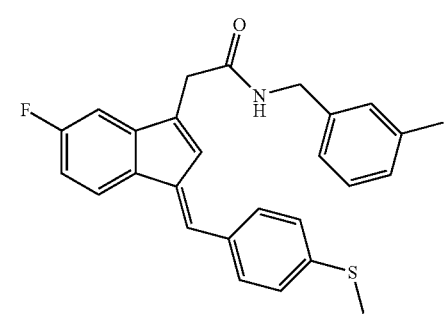 | $C_{27}H_{24}FNOS$ 429.55 |
| 19 | 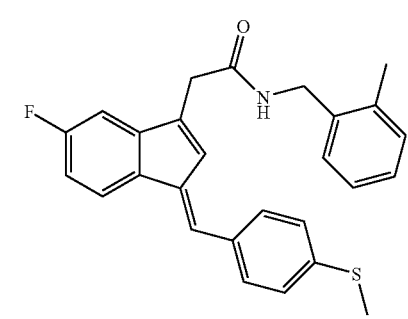 | $C_{27}H_{24}FNOS$ 429.55 |

TABLE 3-continued

Representative Derivatives

| Compound No. | Structure | Formula Mol. Wt. |
|---|---|---|
| 20 | 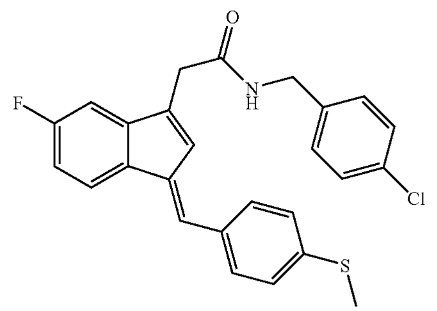 | $C_{26}H_{21}ClFNOS$ 449.97 |
| 21 | 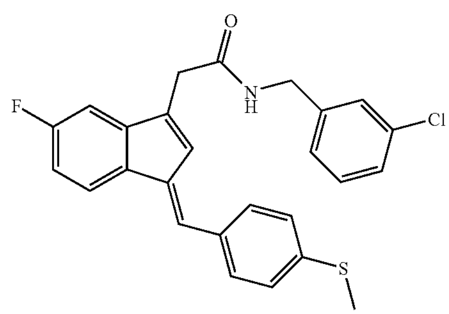 | $C_{26}H_{21}ClFNOS$ 449.97 |
| 22 | 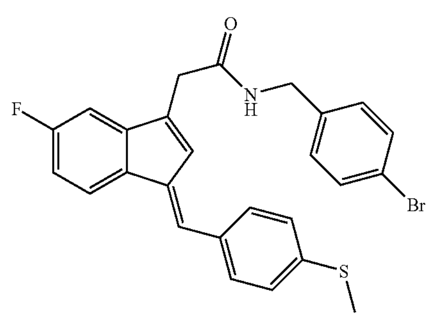 | $C_{26}H_{21}BrFNOS$ 494.42 |
| 23 | 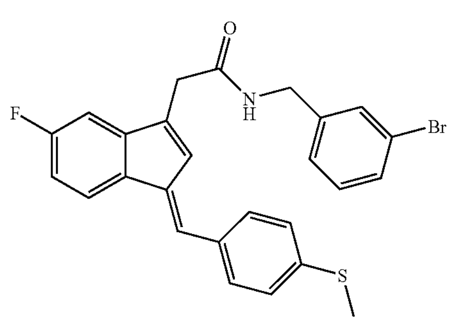 | $C_{26}H_{21}BrFNOS$ 494.42 |

TABLE 3-continued

Representative Derivatives

| Compound No. | Structure | Formula Mol. Wt. |
|---|---|---|
| 24 | 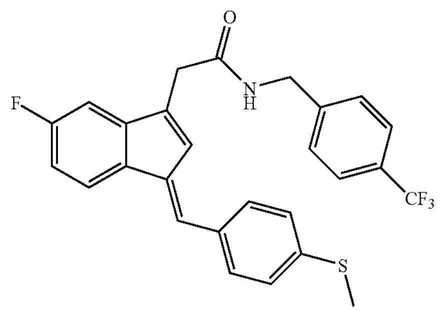 | $C_{27}H_{21}F_4NOS$ 483.52 |
| 25 | 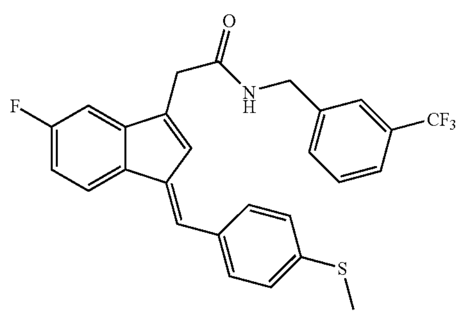 | $C_{27}H_{21}F_4NOS$ 483.52 |
| 26 | 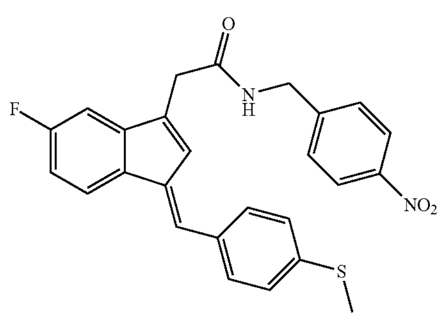 | $C_{26}H_{21}FN_2O_3S$ 460.52 |
| 27 | 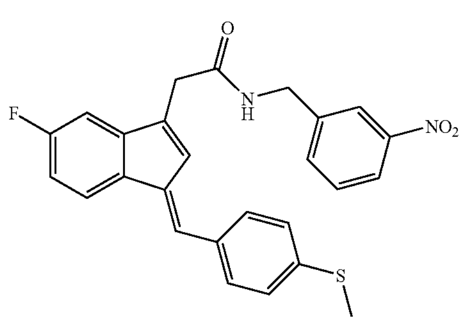 | $C_{26}H_{21}FN_2O_3S$ 460.52 |

TABLE 3-continued
Representative Derivatives
| Compound No. | Structure | Formula Mol. Wt. |
|---|---|---|
| 28 | 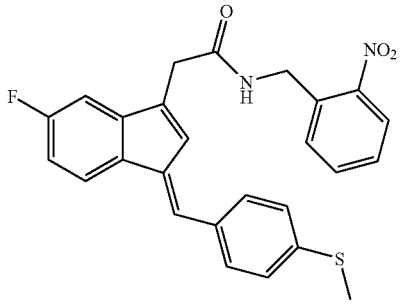 | C$_{26}$H$_{21}$FN$_2$O$_3$S<br>460.52 |
| 29 | 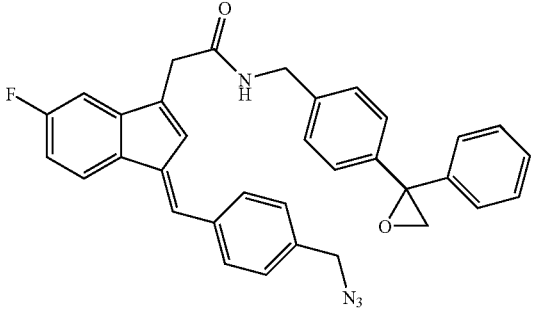 | C$_{34}$H$_{27}$FN$_4$O$_2$<br>542.6 |
| 30 | 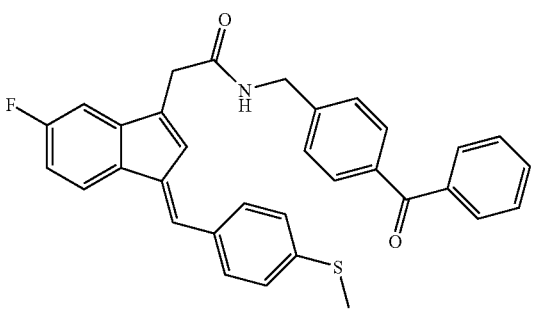 | C$_{33}$H$_{26}$FNO$_2$S<br>519.63 |
| 31 | 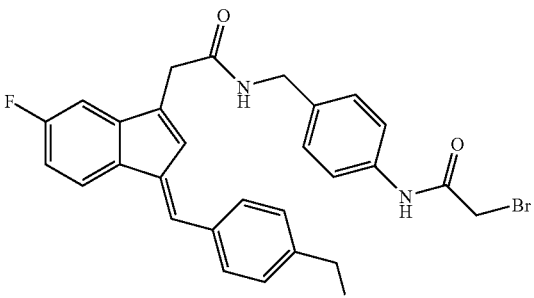 | C$_{28}$H$_{23}$BrFN$_5$O$_2$<br>560.42 |

TABLE 3-continued

Representative Derivatives

| Compound No. | Structure | Formula Mol. Wt. |
|---|---|---|
| 32 | 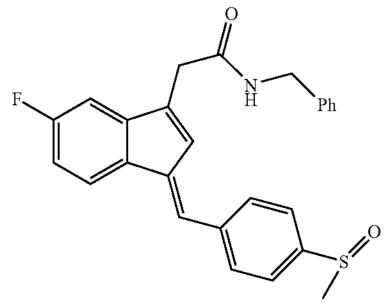 | $C_{26}H_{22}FNO_2S$ 431.52 |
| 33 | 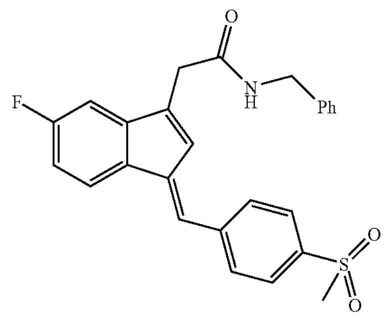 | $C_{26}H_{22}FNO_3S$ 447.52 |
| 34 | 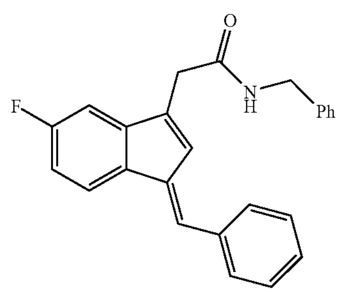 | $C_{25}H_{20}FNO$ 369.43 |
| 35 | 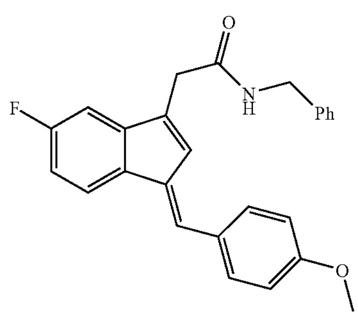 | $C_{26}H_{22}FNO_2$ 399.46 |
| 36 | 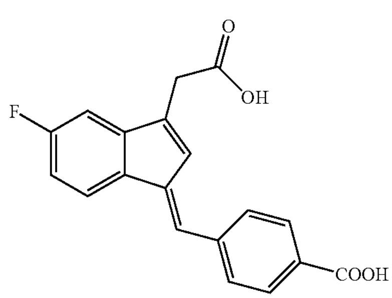 | $C_{19}H_{13}FO_4$ 324.30 |

TABLE 3-continued

Representative Derivatives

| Compound No. | Structure | Formula Mol. Wt. |
|---|---|---|
| 37 | 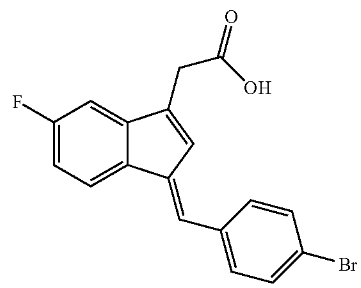 | $C_{18}H_{12}BrFO_2$ 359.19 |
| 38 | 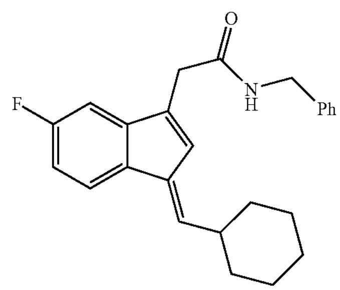 | $C_{25}H_{26}FNO$ 375.48 |
| 39 | 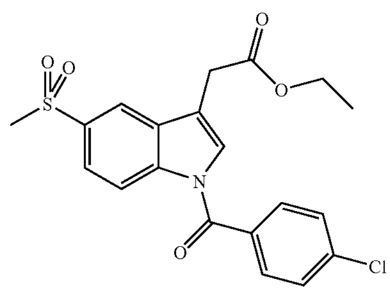 | $C_{20}H_{18}ClNO_5S$ 419.88 |
| 40 | 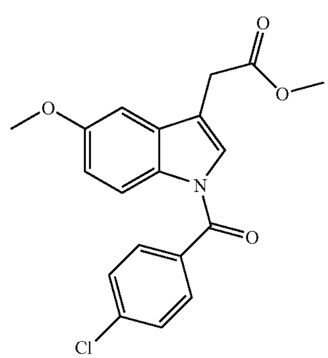 | $C_{19}H_{16}ClNO_4$ 357.79 |
| 41 | 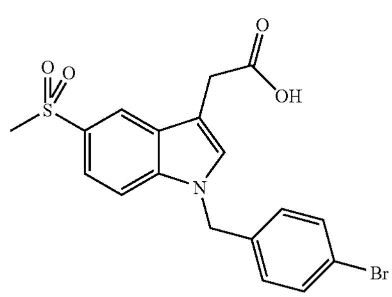 | $C_{18}H_{16}BrNO_4S$ 422.29 |

TABLE 3-continued

Representative Derivatives

| Compound No. | Structure | Formula Mol. Wt. |
|---|---|---|
| 42 | 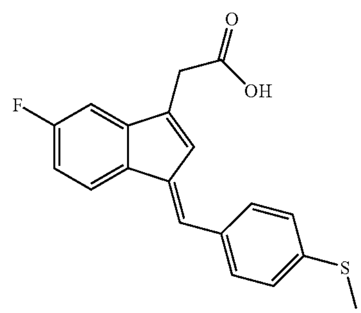 | $C_{19}H_{15}FO_2S$ 326.38 |
| 43 | 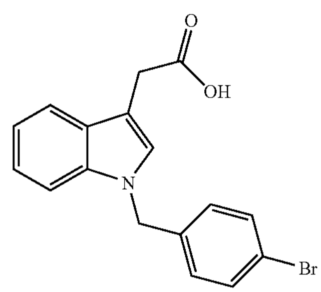 | $C_{17}H_{14}BrNO_2$ 344.20 |
| 44 | 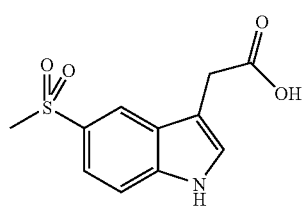 | $C_{11}H_{11}NO_4S$ 253.27 |
| 45 | 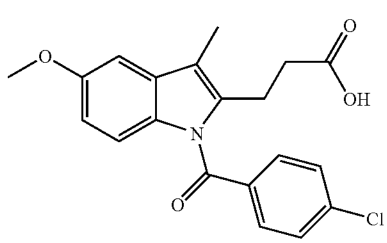 | $C_{20}H_{18}ClNO_4$ 371.81 |
| 46 | 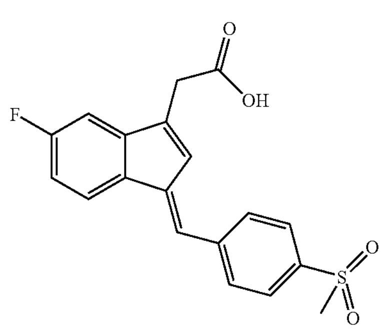 | $C_{19}H_{15}FO_4S$ 358.38 |

TABLE 3-continued
Representative Derivatives
| Compound No. | Structure | Formula Mol. Wt. |
|---|---|---|
| 47 | 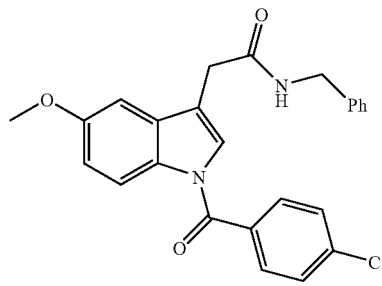 | $C_{25}H_{21}ClN_2O_3$<br>432.90 |
| 48 | 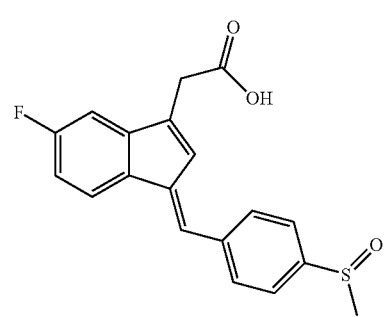 | $C_{19}H_{15}FO_3S$<br>342.38 |
| 49 | 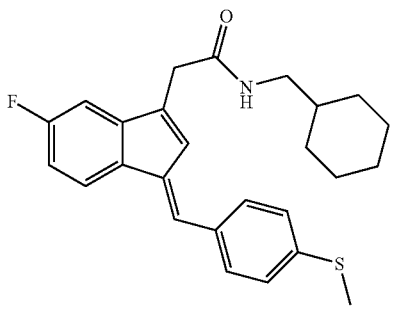 | $C_{26}H_{28}FNOS$<br>421.57 |
| 50 | 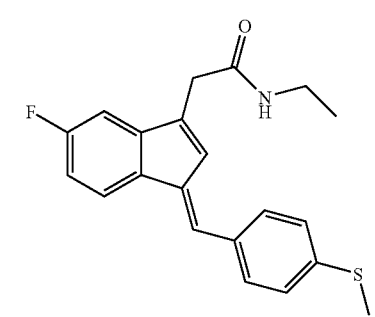 | $C_{21}H_{20}FNOS$<br>353.45 |
| 51 | 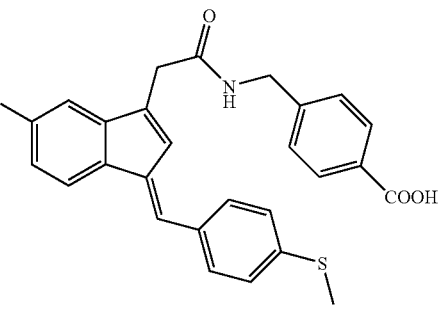 | $C_{27}H_{22}FNO_3S$<br>459.53 |

TABLE 3-continued

Representative Derivatives

| Compound No. | Structure | Formula Mol. Wt. |
|---|---|---|
| 52 | 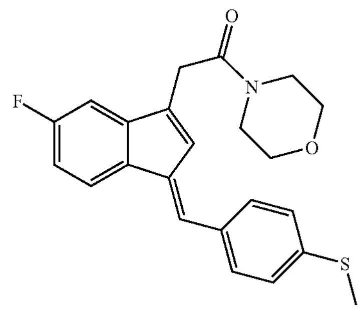 | $C_{23}H_{22}FNO_2S$<br>395.49 |
| 53 | 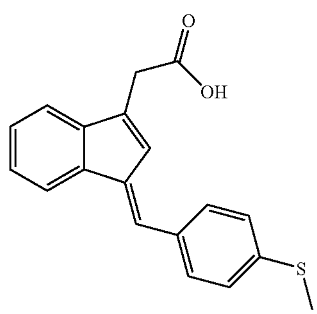 | $C_{19}H_{16}FNO_2S$<br>308.39 |
| 54 | 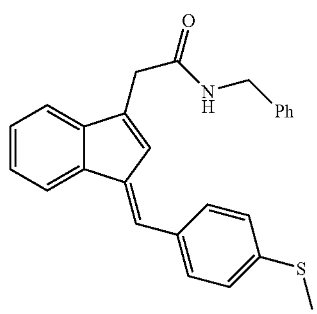 | $C_{26}H_{23}NOS$<br>397.53 |
| 55 | 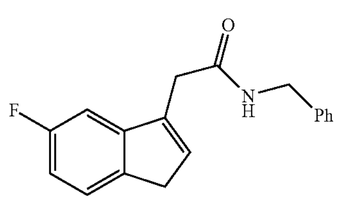 | $C_{18}H_{16}FNO$<br>281.32 |
| 56 | 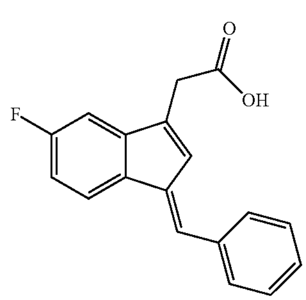 | $C_{18}H_{13}FO_2$<br>280.29 |

TABLE 3-continued

Representative Derivatives

| Compound No. | Structure | Formula Mol. Wt. |
|---|---|---|
| 57 | 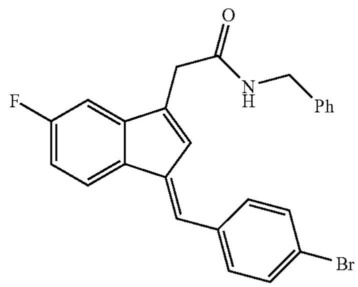 | $C_{25}H_{19}BrFNO$ 448.33 |
| 58 | 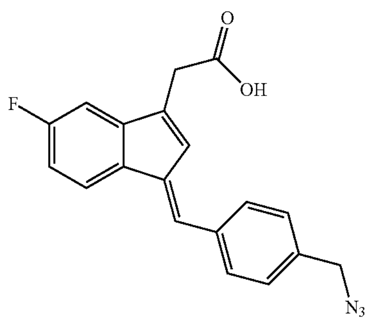 | $C_{19}H_{14}FN_3O_2$ 335.33 |
| 59 | 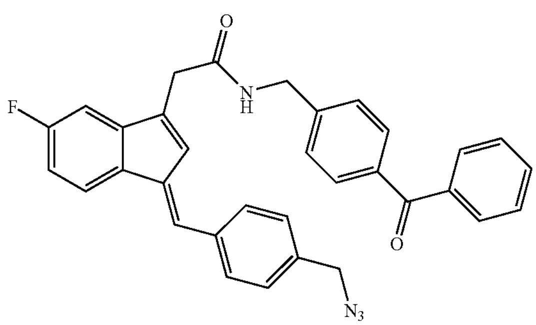 | $C_{33}H_{25}FN_4O_2$ 528.58 |
| 60 | 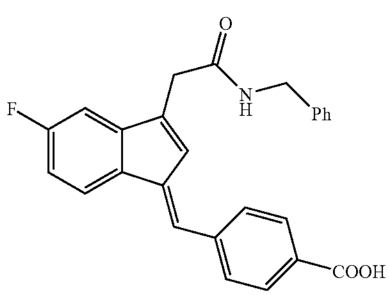 | $C_{26}H_{20}FNO_3$ 413.44 |
| 61 | 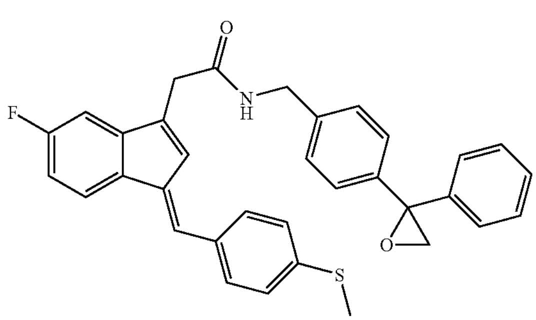 | $C_{34}H_{28}FNO_2S$ 533.67 |

TABLE 3-continued
Representative Derivatives
| Compound No. | Structure | Formula Mol. Wt. |
|---|---|---|
| 62 | 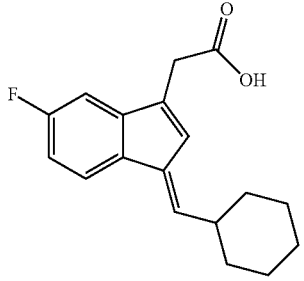 | C₁₈H₁₉FO₂<br>286.14 |
| 63 | 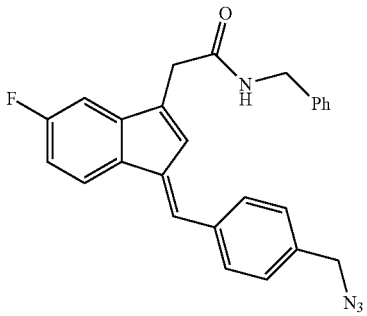 | C₂₆H₂₁FN₄O<br>424.47 |
| 64 | 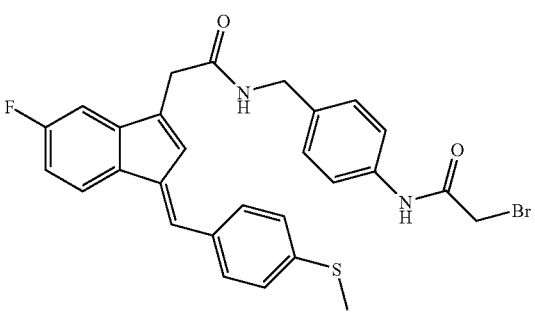 | C₂₈H₂₄BrFN₂O₂S<br>551.48 |
| 65 | 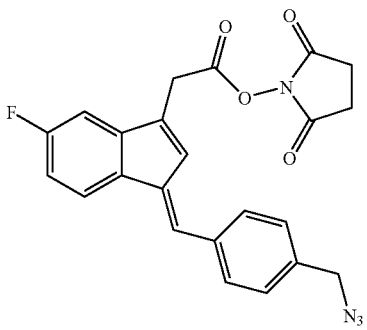 | C₂₃H₁₇FN₄O₄<br>432.4 |

TABLE 3-continued

Representative Derivatives

| Compound No. | Structure | Formula Mol. Wt. |
|---|---|---|
| 66 | 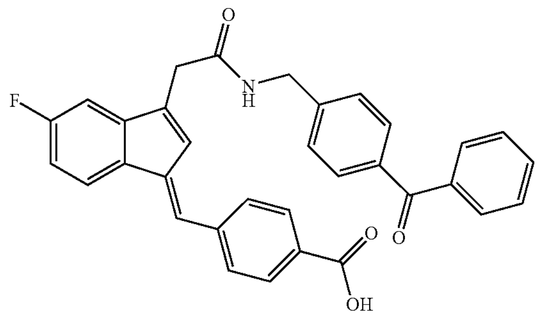 | $C_{33}H_{24}FNO_4$<br>517.55 |
| 67 | 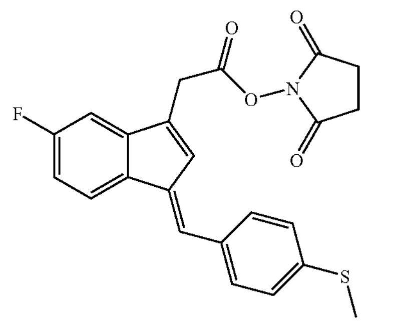 | $C_{23}H_{18}FNO_4S$<br>423.46 |
| 68 | 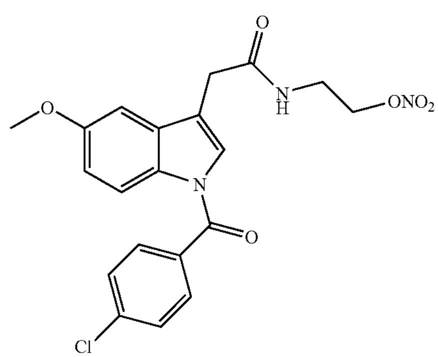 | $C_{20}H_{18}ClN_3O_6$<br>431.83 |
| 69 | 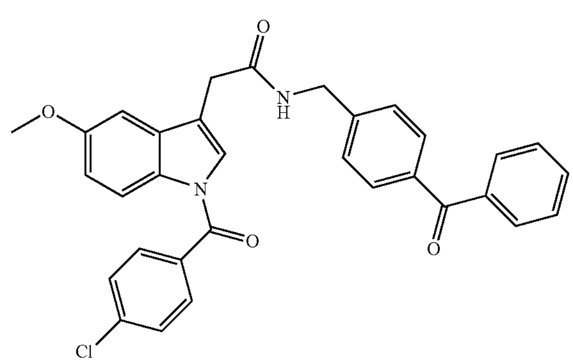 | $C_{32}H_{25}ClN_2O_4$<br>537 |

TABLE 3-continued

Representative Derivatives

| Compound No. | Structure | Formula Mol. Wt. |
|---|---|---|
| 70 | 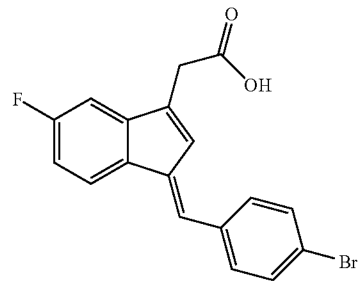 | $C_{18}H_{12}BrFO_2$<br>359.19 |
| 71 | 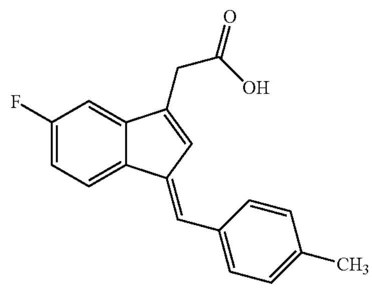 | $C_{19}H_{15}FO_2$<br>294.32 |
| 72 | 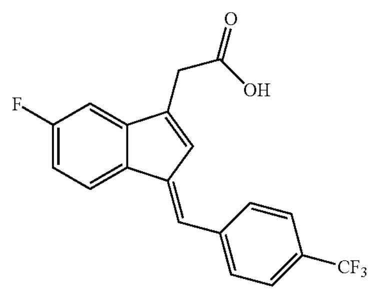 | $C_{19}H_{13}F_4O_2$<br>349.30 |
| 73 | 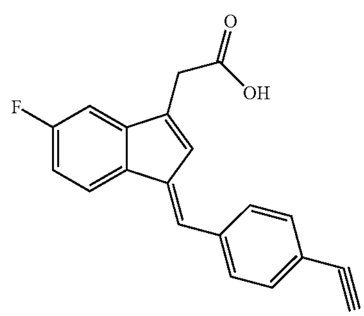 | $C_{20}H_{13}FO_2$<br>304.31 |
| 74 | 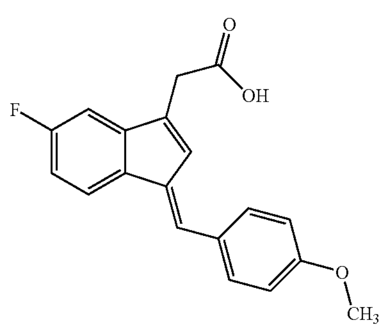 | $C_{19}H_{15}FO_3$<br>310.32 |

TABLE 3-continued

Representative Derivatives

| Compound No. | Structure | Formula Mol. Wt. |
|---|---|---|
| 75 | 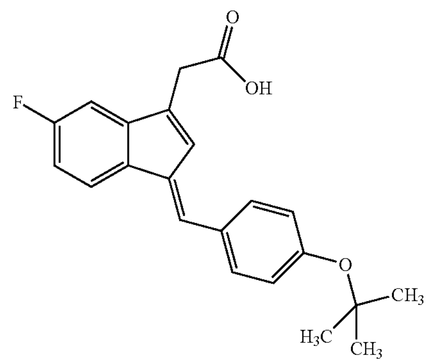 | $C_{22}H_{21}FO_3$ 352.42 |
| 76 | 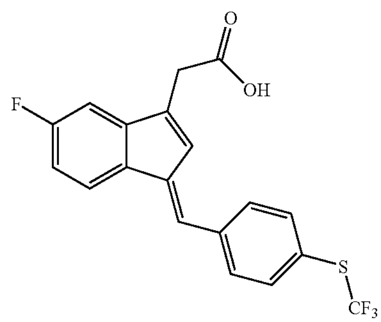 | $C_{19}H_{12}F_4O_2S$ 380.36 |
| 77 | 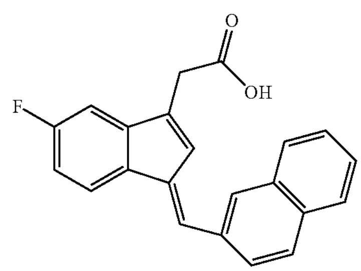 | $C_{22}H_{15}FO_2$ 330.35 |
| 78 | 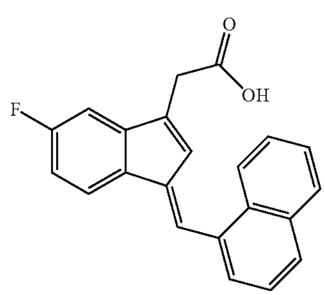 | $C_{22}H_{15}FO_2$ 330.35 |
| 79 | 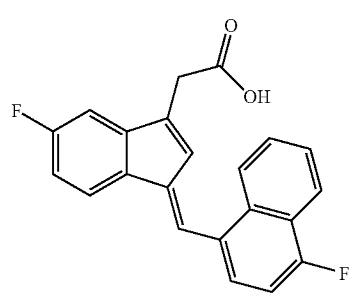 | $C_{22}H_{14}F_2O_2$ 348.34 |

TABLE 3-continued

Representative Derivatives

| Compound No. | Structure | Formula Mol. Wt. |
|---|---|---|
| 80 | 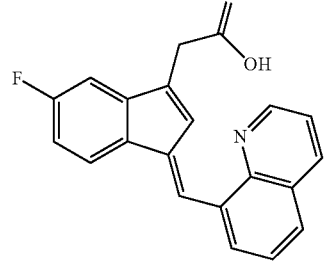 | C₂₁H₁₄FNO₂ 331.34 |
| 81 | 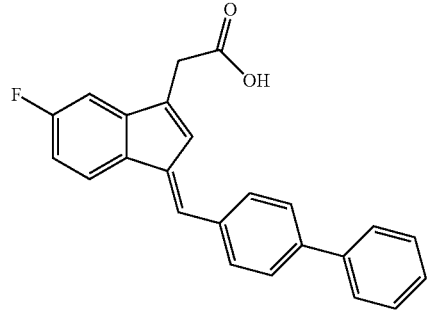 | C₂₄H₁₇FO₂ 356.39 |
| 82 | 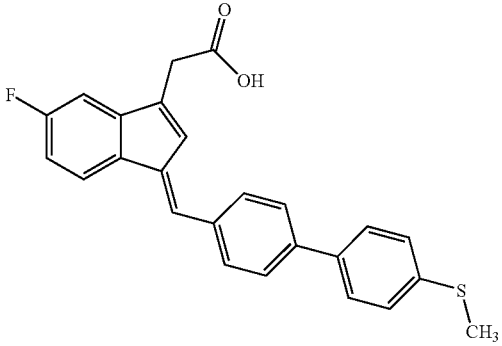 | C₂₅H₁₉FO₂S 402.48 |
| 83 | 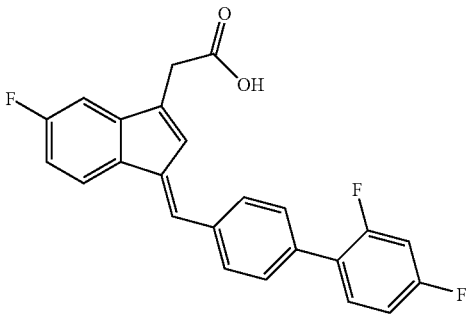 | C₂₄H₁₅F₃O₂ 424.43 |

III.B. Modulation of PPARs

Diabetes mellitus is a condition in which the glucose homeostasis of a subject becomes unbalanced and leads to a hyperglycemic systemic condition. There are two forms of the diabetic condition, Type I and Type II. Type I diabetes usually occurs in individuals under approximately 20 years of age, is insulin-dependent, is commonly accompanied by ketoacidosis and represents about 10% of the diabetic population. Type II diabetes affects approximately 5 percent of the adult American population and represents about 90% of the diabetic population. Type II diabetes is commonly associated with obesity, usually occurs in individuals over approximately 40 years of age and is non-insulin dependent. A subset of type II diabetes can occur in younger individuals and is referred to as maturity onset diabetes of the young (MODY).

PPARs, particularly PPARγ, have been implicated in mediating differentiation of adipocytes and regulating fat metabolism. Additionally, PPARγ has been associated with various pathological conditions related to atherosclerosis, inflammation, obesity, diabetes, the immune response, and ageing. See Kersten et al., 2000; Celi & Shuldiner, 2002.

In some embodiments, the presently disclosed subject matter provides a method of modulating the activity of a PPAR (e.g., PPARγ). In this embodiment, a treatment effective amount of a derivative of the presently disclosed subject matter is administered to a subject having a PPAR, whereby the activity of the PPAR is modulated.

III.C. Modulation of Cell Growth

Peroxisome proliferators-activated receptors (PPARS) have been associated with various pathological conditions related to atherosclerosis, inflammation, obesity, diabetes, the immune response, and ageing. Activation of one particular member of this family of receptors, PPARγ, by cyclopentenone prostaglandins (PGs) such as 15-deoxy-$\Delta^{12,14}$-prostaglandin $J_2$ (15d-$PGJ_2$), causes anti-proliferation, apoptosis, differentiation, and anti-inflammatory responses in certain types of cancer cells.

In some embodiments, the presently disclosed subject matter provides a method of modulating the activity of a PPAR (e.g., PPARγ). In this embodiment, a treatment effective amount of a derivative of the presently disclosed subject matter is administered to a subject having a PPAR, whereby the activity of the PPAR is modulated.

III.D. Modulation of Secretases

As discussed in more detail hereinabove, secretases are involved in the processing of Aβ peptide, including the generation of Aβ42, the purported etiologic agent in Alzheimer's disease. In some embodiments, the presently disclosed subject matter provides a method of modulating the activity of a secretase (e.g., γ-secretase). In this embodiment, a treatment effective amount of a derivative of the presently disclosed subject matter is administered to a subject having a secretase, whereby the activity of the secretase is modulated.

IV. TREATMENT METHODS

IV.A. Subjects

The presently disclosed subject matter also provides a method for treating a disease in a subject, wherein the disease is selected from the group consisting of a cancer, a neurodegenerative disease, and diabetes, the method comprising administering to the subject a treatment effective amount of a derivative of a compound, wherein the compound comprises a cyclooxygenase inhibitor comprising an indoleacetic acid or indenacetic acid functional group having a 2' methyl group and the derivative substantially lacks cyclooxygenase inhibitory activity as a result of modifying the 2' methyl group to a moiety selected from the group consisting of hydrogen, halo, and $C_2$ to $C_6$ alkyl or branched alkyl.

As used herein, the phrase "treating a disease in a subject" refers to both intervention designed to ameliorate the symptoms of causes of the disease in a subject (e.g., after initiation of the disease process) as well as to interventions that are designed to prevent the disease from occurring in the subject. Stated another way, the terms "treating" and grammatical variants thereof are intended to be interpreted broadly to encompass meanings that refer to reducing the severity of and/or to curing a disease, as well as meanings that refer to prophylaxis. In this latter respect, "treating" refers to "preventing" or otherwise enhancing the ability of the subject to resist the disease process.

The subjects treated in the presently disclosed subject matter in its many embodiments is desirably a human subject, although it is to be understood that the principles of the presently disclosed subject matter indicate that the presently disclosed subject matter is effective with respect to invertebrate and to all vertebrate animals, including mammals, which are intended to be included in the term "subject". Moreover, a mammal is understood to include any mammalian species in which treatment or prevention of a disease is desirable, particularly agricultural and domestic mammalian species. For example, the presently disclosed subject matter is applicable to the treatment of livestock.

The methods of the presently disclosed subject matter are particularly useful in the treatment of warm-blooded vertebrates. Thus, the presently disclosed subject matter concerns mammals and birds.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

IV.B. Formulation

The compositions of the presently disclosed subject matter comprise in some embodiments a composition that includes a carrier, particularly a pharmaceutically acceptable carrier. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

IV.C. Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a composition of the presently disclosed subject matter include but are not limited to intravenous injection. The particular mode of administering a composition of the presently disclosed subject matter depends on various factors, including the distribution and abundance of cells to be treated, the compound employed, additional tissue- or cell-targeting features of the compound, and mechanisms for metabolism or removal of the compound from its site of administration.

IV.D. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). In some embodiments, an activity that inhibits amyloid aggregate formation is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples provide illustrative embodiments. Certain aspects of the following Examples are described in terms of techniques and procedures found or contemplated by the present inventors to work well in the practice of the embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Mutagenesis and Purification of mCOX-2

Site-directed mutagenesis, expression, and purification of murine COX-2 (mCOX-2) nucleic acids and polypeptides were performed as described in Rowlinson et al., 1999. Briefly, PCR-mediated site-directed mutagenesis was performed on a mCOX-2 coding sequence present in a BLUESCRIPT® vector (Stratagene, La Jolla, Calif., United States of America) using the QUIKCHANGE® Site-Directed Mutagenesis Kit (Stratagene). The GTG codon encoding a valine at position 335 in wild type mCOX-2 (referred to herein as Val-349 based on the numbering convention discussed hereinabove) was changed to encode an alanine, a leucine, or an isoleucine, creating three mutant nucleic acids encoding mCOX-2 polypeptides referred to herein as mCOX-$2^{V349A}$ or V349A, mCOX-$2^{V349L}$ or V339L, and mCOX-$2^{V349I}$ or V349I, respectively.

In order to express the mutant polypeptides, sequences containing the mutagenized codons were removed from the mCOX-2-containing BLUESCRIPT® vector and subcloned into a pVL1393 baculovirus expression vector (BD Biosciences PharMingen, San Diego, Calif., United States of America) encoding mCOX-2 using the BamHI restriction site present in both the mCOX-2-containing BLUESCRIPT® and pVL1393 vectors. The subcloned region was fully sequenced to ensure that no additional mutations were incorporated into the expression vectors.

Wild type and mutant protein was then expressed by homologous recombination of the mCOX-2z/pVL1393 vector with the BACULOGOLD™ vector (BD Biosciences PharMingen) in Sf9 cells (EMD Biosciences, Inc.—Novagen, Madison, Wis., United States of America). After virus amplification, 4 liters of Sf9 cells (95-100% viable) were grown in TNM-FH medium supplemented with 10% fetal bovine serum (FBS; HyClone, Logan, Utah, United States of America), 1% L-glutamine, and 0.1% (v/v) pluronic F68 and then infected with fresh viral stock. Upon reaching 65-70% viability, the 4-liter total volume was harvested by centrifugation at 2500 rpm in a Sorvall RC-3B centrifuge, and the pellet was washed in ice-cold phosphate-buffered saline and re-centrifuged. The final cell pellet was stored at −80° C.

Purification of wild type and mutant mCOX-2 polypeptides was performed at 4° C. in a manner similar to that described in Gierse et al., 1996. Briefly, frozen cells were resuspended to 30×$10^6$ cells/ml in 80 mM Tris-HCl, 2 mM EDTA, 0.5 mM phenylmethylsulfonyl fluoride, and 0.1 mM diethyldithiocarbamic acid, pH 7.2. After centrifugation at 100,000 g for 45 minutes, the pellet was resuspended using a Dounce homogenizer to a final volume of 72 ml. Solubilization of the COX protein from the membrane was initiated by the dropwise addition of 8 ml of 11% (w/v) CHAPS. After stirring for 1 hour, the sample was re-centrifuged as described above and the supernatant removed and then diluted 4-fold by the addition of 20 mM Tris-HCl, 0.4% CHAPS, 0.1 mM EDTA, and 0.1 mM diethyldithiocarbamic acid, pH 8.0 (Buffer B). The diluted sample was then loaded onto a 25 ml Macro-prep High-Q ion exchange column equilibrated with Buffer B. COX enzyme was eluted with a linear gradient (500 ml) of increasing KCl to 0.3 M. An analytical 7.5% SDS-polyacrylamide gel electrophoresis was run of candidate COX-containing fractions to determine the fractions to pool for the gel filtration procedure. Appropriate tubes were concentrated in an Amicon concentrator (Amicon, Beverly, Mass., United States of America) to a final volume of 1.5 ml. The sample was then loaded onto a 90 ml Sephacryl-200 column that was pre-equilibrated with 20 mM Tris-HCl, 0.4% CHAPS, 0.15 M NaCl, pH 8.0. Fractions containing COX enzyme, as determined from SDS-polyacrylamide gel electrophoresis analysis, were concentrated to approximately 2 mg/ml and stored at −80° C. The purity of wild type and mutant COX-2 proteins was evaluated by analysis of a Coomassie-stained 7.5% SDS-polyacrylamide gel using an E-C Apparatus Model EC910 scanning densitometer (E-C Apparatus Corp., Holbrook, N.Y., United States of America). All proteins were over 80% pure.

Example 2

Reagents and Solvents

Unlabeled arachidonic acid (AA) was purchased from Nu Chek Prep (Elysian, Minn., United States of America), and [1-$^{14}$C]-AA was purchased from PerkinElmer Life Sciences Inc. (Boston, Mass., United States of America). Ram seminal vesicles were purchased from Oxford Biomedical Research (Oxford, Mich., United States of America). Oligonucleotides were purchased from Qiagen, Inc. (Valencia, Calif., United States of America) and all molecular biology enzymes were obtained from New England Biolabs (Beverly, Mass., United States of America). Baculovirus reagents were purchased from BD Biosciences Pharmingen (San Diego, Calif., United States of America). Unless otherwise stated, all other chemicals were obtained from Sigma/Aldrich (St. Louis, Mo., United States of America). HPLC grade solvents used for column chromatography were obtained from Fischer Scientific (Pittsburgh, Pa., United States of America). N,N-Dimethylformamide was distilled from calcium hydride. All other chemicals were used without further purification. Thin layer chromatography was performed on silica plates obtained from Analtech (Newark, Del., United States of America; Silica Gel 60 $F_{254}$ precoated). The plates were read by UV fluorescence (254 nm) or by staining with phosphomolybdic acid (PMA) followed by heating. Column chromatography was performed using silica gel 200-300 mesh (Fisher Scientific).

Example 3

Instrumental Analysis

Mass spectra were obtained by electrospray ionization (ESI-MS) on a Finnigan TSQ 7000 triple-quadrupole spectrometer (Thermo Electron Corp., Waltham, Mass., United States of America). $^1$H-NMR were obtained on a Bruker AC 300 NMR spectrometer (Bruker BioSpin Corporation, Billerica, Mass., United States of America) using CDCl$_3$ or DMSO-d$_6$ as the solvent and tetramethylsilane (TMS) as an internal standard. All chemical shifts are reported in parts per million (ppm) downfield from TMS and coupling constants are reported in hertz.

Example 4

Synthesis of 2-Des-methylindomethacin

Figure 6:
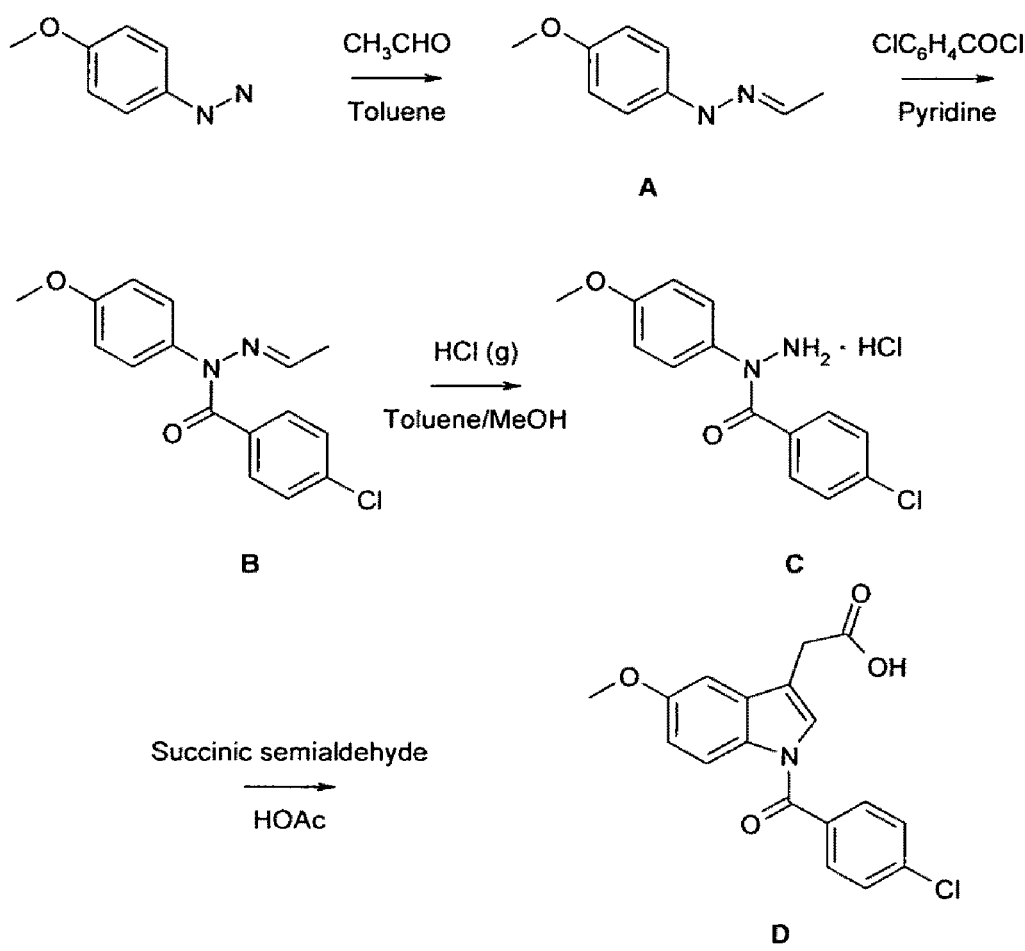
FIG. 6 depicts a scheme for synthesizing 2-Des-methylindomethacin (DM-INDO).

2-Des-methylindomethacin was synthesized according to the steps outlined in FIG. 6. These steps are presented in more detail as follows:

N-Ethylidene-N'-(4-methoxy-phenyl)-hydrazone (Compound A in FIG. 6). 4-Methoxyphenylhydrazine (10.34 g, 0.075 mol) was dissolved in toluene (76 mL) in a flame dried round-bottomed flask. The flask was purged with argon and cooled to 0° C. Acetaldehyde (8.4 mL, 0.15 mol) in toluene (17 mL) was added dropwise and stirring at room temperature was continued for 30 minutes. The solution was decanted through filter paper into a round-bottomed flask and concentrated in vacuo to give 11.2 g of the crude hydrazone (Compound A in FIG. 6).

4-Chloro-benzoic acid N'-ethylidene-N-(4-methoxy-phenyl)-hydrazide (Compound B in FIG. 6). To a solution of the crude hydrazone (Compound A in FIG. 6; 0.424 g, 2.58 mmol) in pyridine (2.2 mL) under argon at 0° C. was added 4-chlorobenzoyl chloride (0.904 g, 5.17 mmol) in one portion. The reaction mixture was stirred at room temperature for 3 hours. Water (25 mL) was added and the solution extracted with CH$_2$Cl$_2$ (3×20 mL). The combined organic phases were dried (MgSO$_4$), filtered, and concentrated in vacuo. Purification by flash chromatography (hexane/ethyl acetate 3:1) afforded the title compound (Compound B in FIG. 6) as an orange solid (0.266 g). $^1$H NMR (CDCl$_3$) δ 7.70 (d, J=7.2 Hz, 2H), 7.36 (d, J=8.2 Hz, 2H), 7.11 (d, J=8.7 Hz, 2H), 7.01 (d, J=8.5 Hz, 2H), 6.82 (d, J=5.0 Hz, 1H), 3.84 (s, 3H), 1.89 (d, J=5.0 Hz, 3H); ESI-CID 325, 327 (M-Na$^+$[$^{35/37}$Cl]).

4-Chloro-benzoic acid N-(4-methoxy-phenyl)-hydrazide hydrochloride (Compound C in FIG. 6). The hydrazide (Compound B in FIG. 6; 0.166 g, 0.55 mmol) was dissolved in toluene (6.6 mL) and methanol (0.33 mL) in a 2 neck flask equipped with a condenser. The mixture was cooled to 0° C. and HCl gas was bubbled through for 1.5 hours. The excess gas and solvent were removed in vacuo. The solid was swirled with toluene and filtered to give a white solid. The solid was washed with ethyl acetate to give the hydrochloride salt (Compound C in FIG. 6) without further purification (0.131 g, 76%). $^1$H NMR (DMSO-d$_6$) δ 7.41 (m, 4H), 7.33 (d, J=8.4 Hz, 2H), 6.92 (d, J=8.9 Hz), 3.74 (s, 3H).

2-Des-methylindomethacin (Compound D in FIG. 6). The hydrochloride salt (Compound C in FIG. 6; 0.111 g, 0.35 mmol) and succinic semialdehyde (0.047 g, 0.46 mmol) were dissolved in acetic acid (AcOH; 2 mL) and heated to reflux for 4 hours. The reaction was allowed to cool to room temperature overnight. Water (5 mL) and CH$_2$Cl$_2$ (5 mL) were added and the organic phase was removed. The aqueous phase was extracted with an additional portion of CH$_2$Cl$_2$ and the combined organics were washed with water and extracted with a saturated solution of NaHCO$_3$ (2×20 mL). The combined aqueous extracts were acidified with 15% HCl and the resulting mixture was extracted with CH$_2$Cl$_2$ (3×20 mL). The combined organics were dried (MgSO$_4$), filtered, and concentrated in vacuo. Recrystallization of the crude product (isopropanol) afforded the title compound (i.e., [1-(4-Chlorobenzoyl)-5-methoxy-1H-indol-3-yl]-acetic acid; Compound D in FIG. 6) as a gray solid (0.058 g, 48%). $^1$H NMR (DMSO-d$_6$) δ 8.24 (d, J=8.9 Hz, 1H), 7.82 (d, J=8.5 Hz, 2H), 7.73 (d, J=8.4 Hz, 2H), 7.39 (s, 1H), 7.19 (d, J=2.3 Hz, 1H), 7.06 (dd, J=2.4, 8.9 Hz, 1H), 3.87 (s, 3H), 3.73 (s, 2H); ESI-CID 342, 344 (M-H$^-$[$^{35/37}$Cl]). Anal. Calcd for C$_{18}$H$_{14}$ClNO$_4$: C, 62.89; H, 4.10; N, 4.07; Cl 10.31. Found: C, 62.80; H, 4.11; N, 4.06; Cl, 10.12.

Example 5

Synthesis of Eindenic Acid Sulfide

Figure 7:
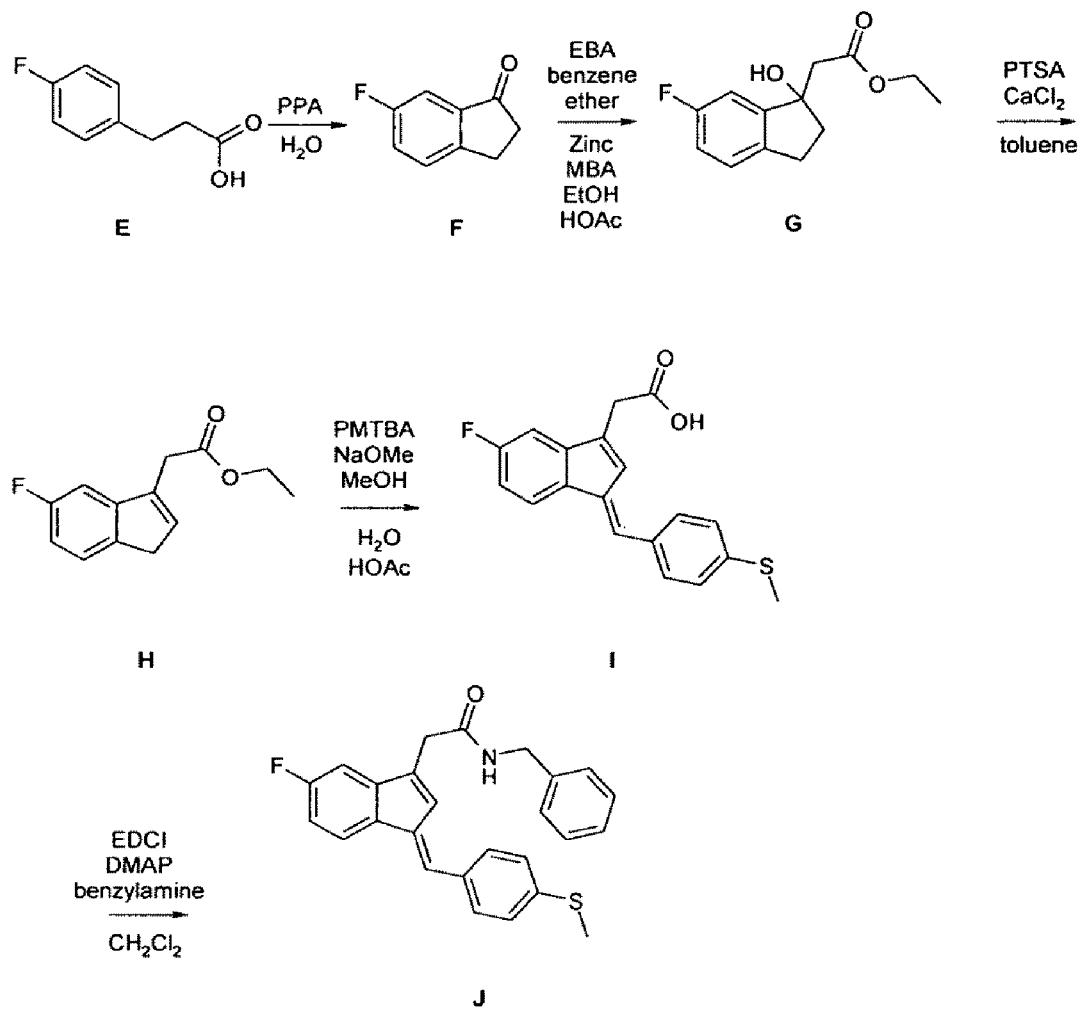
FIG. 7 depicts a scheme for synthesizing eindenic acid sulfide (Compound I) and a derivative of eindenic acid sulfide, N-Benzyl-2-[6-fluoro-3-(4-methylsulfanyl-benzylidene)-3H-inden-1-yl]-acetamide (Compound J).

Eindenic acid sulfide was synthesized according to the steps outlined in FIG. 7. These steps are presented in more detail as follows:

83

6-Fluoro-indan-1-one (Compound F in FIG. 7). 3-(4-Fluoro-phenyl)-propionic acid (5 g, 29.7 mmol; Compound E in FIG. 7) was added to polyphosphoric acid (PPA; 65.4 g, 0.654 mol) at 50° C. The viscous mixture was heated at 90° C. for 2 hours. The syrup was poured into ice water and stirred for 30 minutes. The aqueous mixture was extracted with ether (3×50 mL) and the combined organics were washed with $H_2O$ (2×50 mL) and $NaHCO_3$ until neutralized. The resulting organic phase was washed with $H_2O$ (50 mL), dried ($MgSO_4$), filtered, and concentrated in vacuo. Purification using flash chromatography (7:1 hexane/ethyl acetate (EtOAc)) afforded the indanone (Compound F in FIG. 7) as a yellow solid (2.06 g, 46%). $^1$H NMR ($CDCl_3$) δ 7.45 (ddd, J=0.5, 4.5, 8.4 Hz, 1H), 7.39 (ddd, J=0.3, 2.6, 7.8 Hz, 1H), 7.30 (td, J=2.6, 8.6 Hz, 1H), 3.12 (t, J=5.7 Hz, 2H), 2.75 (m, 2H); ESI-CID 151 (M-H$^+$).

(6-Fluoro-1-hydroxy-indan-1-yl)-acetic acid ethyl ester (Compound G in FIG. 7). A solution of the indanone (Compound F in FIG. 7; 2.06 g, 13.7 mmol) and ethyl bromoacetate (EBA; 3.44 g, 20.6 mmol) in benzene (10 mL) was added over a 5 minute period to activated zinc (3.77 g, 57.7 mmol) in benzene (21 mL) and ether (10 mL). A few crystals of iodine were added to initiate the reaction and the mixture was held at reflux. At 3 hour intervals, 2 batches of zinc (1.8 g, 27.5 mmol) and ethyl bromoacetate (EBA; 1.8 g, 10.8 mmol) were added and the mixture was refluxed overnight. The solution was cooled to room temperature and ethanol (5 mL) and acetic acid (23 mL) were added. The solution was poured into 1:1 aqueous acetic acid (100 mL) and the organic layer was separated. The aqueous phase was extracted with diethyl ether ($Et_2O$; 2×25 mL) and the combined organics were washed with water, $NaHCO_3$, water, dried ($MgSO_4$), filtered, and concentrated in vacuo to give the crude product (Compound G in FIG. 7; 3.55 g).

(6-Fluoro-3H-inden-1-yl)-acetic acid ethyl ester (Compound H in FIG. 7). The crude (6-Fluoro-1-hydroxy-indan-1-yl)-acetic acid ethyl ester (Compound G in FIG. 7; 3.55 g), p-toluene sulfonic acid.$H_2O$ (PTSA; 5.67 g, 29.8 mmol), and $CaCl_2$ (4.13 g, 37.2 mmol) in toluene (66 mL) were refluxed overnight. The solution was filtered and the solid residue washed with benzene. The combined organics were washed with water, $NaHCO_3$, water, dried ($MgSO_4$), filtered, and concentrated in vacuo. Purification using flash chromatography (13:1 hexane/EtOAc) afforded the title compound (Compound H in FIG. 7) as an orange solid (0.703 g). $^1$H NMR ($CDCl_3$) δ 7.25 (m, 2H), 7.06 (m, 1H), 6.25 (d, J=2.3 Hz, 1H), 4.24 (q, J=7.0 Hz, 2H), 3.32 (s, 2H), 3.03 (s, 2H), 1.33 (t, J=7.1 Hz, 3H); ESI-CID 221 (M-H$^+$).

Eindenic acid sulfide (Compound I in FIG. 7). To a solution of the (6-Fluoro-3H-inden-1-yl)-acetic acid ethyl ester (Compound H in FIG. 7; 0.668 g, 3.0 mmol) and p-methylthiobenzaldehyde (PMTBA; 0.508 g, 3.3 mmol) in MeOH (18 mL) was added 1N NaOH (9 mL). The mixture was stirred at reflux for 2 hours. The solution was cooled, diluted with water, and extracted with ether (3×). Residual ether was blown off the aqueous phase with nitrogen and the aqueous solution acidified with 50% acetic acid. The precipitated product was filtered and washed with $H_2O$. Recrystallization from methanol afforded the title compound (i.e., [6-Fluoro-3-(4-methylsulfanyl-benzylidene)-3H-inden-1-yl]-acetic acid (i.e., eidenic acid sulfide; Compound I in FIG. 7) as an orange solid (0.163 g, 17%) $^1$H NMR (DMSO-d$_6$) δ 7.83 (dd, J=5.2, 8.4 Hz, 1H), 7.64 (d, J=8.4 Hz, 2H), 7.59 (s, 1H), 7.36 (d, J=8.4 Hz, 2H), 7.16 (dd, J=2.4, 9.6 Hz, 1H), 7.13 (s, 1H), 7.06 (td, J=2.4, 9.6 Hz, 1H), 3.68 (s, 2H), 2.54 (s, 3H); ESI-CID 325 (M-H$^-$).

84

Example 6

Synthesis of a Derivative of Eindenic Acid Sulfide

To a solution of [6-Fluoro-3-(4-methylsulfanyl-benzylidene)-3H-inden-1-yl]-acetic acid (Compound I in FIG. 7; 0.02 g, 0.06 mmol) in dry $CH_2Cl_2$ (1.5 mL) was added N-(3-dimethylaminopropyl)-N'-ethyl carbodiimide (EDCI; 0.014 g, 0.07 mmol), dimethylaminopyridine (DMAP; 0.75 mg, 0.006 mmol) and benzylamine (7.9 mg, 0.07 mmol). The reaction was stirred at room temperature overnight. The mixture was diluted with water and extracted with $CH_2Cl_2$ (2×). The combined organics were washed with $H_2O$, dried ($MgSO_4$), filtered, and concentrated in vacuo. Purification using flash chromatography (5:2 hexane/EtOAc) afforded the title compound (N-Benzyl-2-[6-fluoro-3-(4-methylsulfanyl-benzylidene)-3H-inden-1-yl]-acetamide; Compound J in FIG. 7) as an orange solid. (0.02 g, 79%).

Example 7

Cyclooxygenase Preparation and Assay

COX Inhibition Screening Assay

PCR based site-directed mutagenesis of murine COX-2 changed the valine at position 349 (ovine COX-1 numbering) to alanine, isoleucine, or leucine as outlined in Example 1. These mutated genes were used to assemble baculoviral constructs for large-scale expression in Sf9 cells. Purification of the expressed COX-2 protein was performed through traditional cellular fractionation and classical column chromatography. Activity or inhibition assays were performed in 100 mM Tris-HCl buffer containing 500 μM phenol, with hematin-reconstituted protein. Quantification of cyclooxygenase activity was performed by monitoring substrate (arachidonate or oxygen) consumption in a thermostatted cuvette at 37° C. using a polarographic electrode with a 5300 oxygen monitor (Yellow Springs Instrument Co. Inc., Yellow Springs, Ohio, United States of America). All inhibitors and substrates were solubilized in dimethyl sulfoxide (DMSO). Activity or inhibition assays were performed in 100 mM Tris-HCl buffer containing 500 μM phenol, with hematin-reconstituted protein. Maximal reaction velocity data were obtained from the linear portion of the oxygen uptake curves, and the data were analyzed by nonlinear regression with Prism 4.0 (GraphPad Software, San Diego, Calif., United States of America).

Reactions were run with reconstituted protein at final concentrations adjusted to give approximately 40% substrate consumption (ovine COX-1 (oCOX-1)=35 nM, wild type mCOX-2=55 nM, V349A=250 nM, V349I=250 nM, and V349L=100 nM). Time-dependent inhibition reactions were performed by pre-incubating the inhibitor and enzyme for 17 minutes at 25° C., followed by 3 minutes at 37° C. prior to the addition of 50 μM [1-$^{14}$C]-AA for 30 seconds at 37° C. Assays were terminated and analyzed for substrate consumption by thin layer chromatography as previously described (Kalgutkar et al., 2000a). All inhibitor concentrations for 50% enzyme activity ($IC_{50}$) were determined graphically and were the average of at least two independent determinations.

Competitive inhibition assays were performed in a similar manner, except substrate and inhibitor were added prior the initiation of the reaction by addition of protein. The peroxidase activity of purified proteins was measured by the guaiacol method as described in Markey et al., 1987. The $K_m$'s and $V_{max}$'S for COX activity and the relative peroxidase activity of COX-2 mutants are shown in Table 4.

TABLE 4

Characterization of Val-349 mutant COXs.[a]

| Enzyme | Peroxidase Activity (% wild type mCOX-2) | $K_m$ (μM) | Cyclooxygenase $V_{max}$[b] (μM of AA · min$^{-1}$ · mg$^{-1}$) |
|---|---|---|---|
| wild type mCOX-2 | 100 | 4.2 ± 1.5 | 16.3 ± 1.5 |
| V349A | 51 | 13.0 ± 4.2 | 1.2 ± 0.1 |
| V349I | 65 | 9.0 ± 2.8 | 1.9 ± 0.2 |
| V349L | 88 | 15.2 ± 7.3 | 6.0 ± 1.0 |

[a]Peroxidase activity was analyzed with the guaiacol peroxidase assay, and cyclooxygenase kinetic parameters were determined using at least 7 concentrations of substrate.
[b]The cyclooxygenase $V_{max}$ was normalized to protein concentration and represented as specific activity. The values are the average of three determinations ± standard error (S.E.).

Maximal reaction velocity data were obtained from the linear portion of the oxygen uptake curves, and the data were analyzed by nonlinear regression. Instantaneous inhibition assays were performed with substrate and inhibitor added prior the initiation of the reaction by addition of protein. Time-dependent screening assays were performed by pre-incubating the inhibitor and enzyme for 17 minutes at 25° C., followed by 3 minutes at 37° C. prior to the addition of 50 μM [1-$^{14}$C]-arachidonic acid (AA) for 30 seconds at 37° C.

Assays were terminated and analyzed for substrate consumption by thin layer chromatography. All inhibitor concentrations for 50% enzyme activity ($IC_{50}$) were the average of at least two independent determinations. Time-dependent COX inhibition reactions were pre-incubated at 37° C. for varying lengths of time (0-30 minutes) with various concentrations of inhibitor. All reactions were performed with [1-$^{14}$C]-AA for 30 seconds at 37° C.; reactions were terminated and analyzed as described above.

Example 8

Time-Dependent COX Inhibition Assays

As described in Example 1, to investigate the interactions of the 2' methyl group with the methyl-binding pocket, a series of mutations were made at position 349 in mCOX-2 to increase or decrease the volume of the pocket (Val→Ala, Ile, Leu) and the kinetics of inhibition of these enzymes by INDO were determined. Initially, a time-dependent $IC_{50}$ assay was used, in which the enzymes were pre-incubated with inhibitor for 20 minutes before the addition of 50 μM AA. The COX reaction was allowed to proceed for 30 seconds before termination. The $IC_{50}$ values indicated that the potency of INDO increased when the volume of the pocket increased (V349A) and decreased when the volume of the pocket decreased (V349I, V349L; Table 5).

TABLE 5

Time-dependent $IC_{50}$ determinations of INDO and DM-INDO.[a]

| Enzyme | INDO (μM) | DM-INDO (μM) |
|---|---|---|
| V349A | 0.08 | >16 |
| wild type mCOX-2 | 0.25 | 4 |
| V349I | 0.45 | 3 |
| V349L | 4 | >16 |
| wild type oCOX-1 | 0.04 | >16 |

[a]Values are the average of two independent determinations

Figure 2:
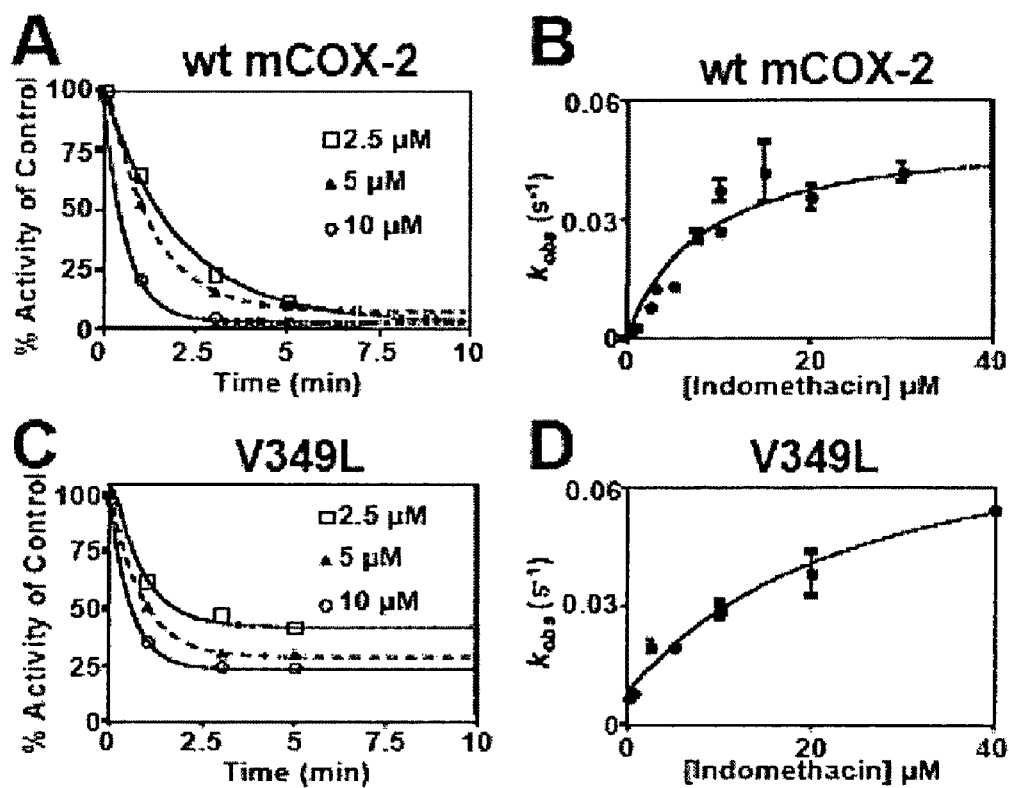
FIGS. 2A-2D depict the kinetics of the time-dependent inhibition of COX-2 mutants by INDO. Assays were performed with various concentrations of either INDO or DM-INDO as described in Example 7.

The time-dependence of inhibition of wild type and mutant COXs by INDO was determined by adding AA (50 μM) to the various enzyme preparations following preincubation with INDO for different times. To ensure that pseudo-first-order conditions were maintained, the enzymatic oxygenation reactions were terminated after 30 seconds to prevent extensive consumption of substrate. The decline of substrate conversion at different INDO concentrations was plotted against the preincubation times and fit to a single exponential decay with a plateau to determine $k_{obs}$ (FIG. 2). The time-dependent inhibition curves for wild type mCOX-2 approached 0% remaining activity. The graphs for V349A and V349I also approached 0% remaining activity, although V349A displayed a faster rate of inhibition. Interestingly, V349L approached a non-zero asymptote of nearly 20% remaining activity, which suggested that the second step of binding was reversible (FIG. 2C). The dependence of $k_{obs}$ on the INDO concentration for the two-step, time-dependent mechanism shown in equation (1) is represented by equation (2) (see also Timofeevski et al., 2002).

$$E + I \underset{k_{-1}}{\overset{k_1}{\rightleftharpoons}} E - I \underset{k_{-2}}{\overset{k_2}{\rightleftharpoons}} E - I^* \quad K_I = k_{-1}/k_1 \tag{1}$$

$$k_{obs} = \frac{k_2 \cdot [I]}{(K_I + [I])} + k_{-2} \tag{2}$$

The rate constant $k_2$ represents the limiting forward rate constant for functionally irreversible inhibition, and $K_I$ corresponds to the inhibitor concentration that yields a rate equal to half of the limiting rate. The reverse rate constant of the second step $k_{-2}$ is equal to the y-intercept, and is equal to zero for compounds that display functionally irreversible inhibition. For wild type mCOX-2, V349A, and V349I enzymes, the y-intercept was effectively zero, indicating that the inhibition was functionally irreversible (FIG. 2B). In contrast, the secondary plot of data for V349L exhibited a non-zero y-intercept, which was equal to $k_{-2}$.

Kinetic parameters for wild type mCOX-2 (Table 6) were in good agreement with previously reported values of $K_I$ (5 μM) and $k_2$ (0.045 s$^{-1}$; Gierse et al., 1999). The values for oCOX-1 indicate that INDO displayed higher affinity ($K_I$=1.7 μM) and a faster rate of inactivation ($k_2$=0.25 s$^{-1}$; Kulmacz & Lands, 1985). These observations are further supported by the higher potency of INDO towards oCOX-1 compared to mCOX-2 (Table 5). The $K_I$ of V349A for INDO decreased almost four-fold, which suggested a higher affinity of binding. This mutation also slightly increased $k_2$, which corresponded to the three-fold reduction in the $IC_{50}$ value for INDO against the V349A enzyme (Table 5). As noted in Table 5, the V349I mutation had little effect on the kinetic parameters of INDO. V349L demonstrated the greatest impact on inhibition, increasing $K_I$ threefold and introducing a measurable $k_{-2}$. The slight rise in $k_2$ suggested a faster rate to equilibrium, which was attributed to the emergence of $k_{-2}$ (FIG. 2C).

TABLE 6

Kinetic parameters of time-dependent inhibition by INDO.[a]

| Enzyme | $K_I$ (μM) | $k_2$ (s$^{-1}$) | $k_{-2}$ (s$^{-1}$) | $K_{-2}$[b] (s$^{-1}$) |
|---|---|---|---|---|
| wild type | 7.9 ± 2.2 | 0.052 ± 0.005 | ND | ND |
| V349A | 1.9 ± 0.4 | 0.074 ± 0.005 | ND[c] | ND |

TABLE 6-continued

Kinetic parameters of time-dependent inhibition by INDO.[a]

| Enzyme | $K_I$ (μM) | $k_2$ (s$^{-1}$) | $k_{-2}$ (s$^{-1}$) | $K_{-2}$[b] (s$^{-1}$) |
|---|---|---|---|---|
| V349I | 5.3 ± 1.8 | 0.045 ± 0.004 | ND | ND |
| V349L | 26 ± 10 | 0.074 ± 0.013 | 0.008 ± 0.002 | 0.010 ± 0.002 |

[a]Kinetic parameters ± S.E. were determined from inhibition assays.
[b]Rate constant determined by reversible inhibition.
[c]Values were not detectable (ND).

Example 9

Time-Dependent COX Inhibition by DM-INDO

Figure 4:
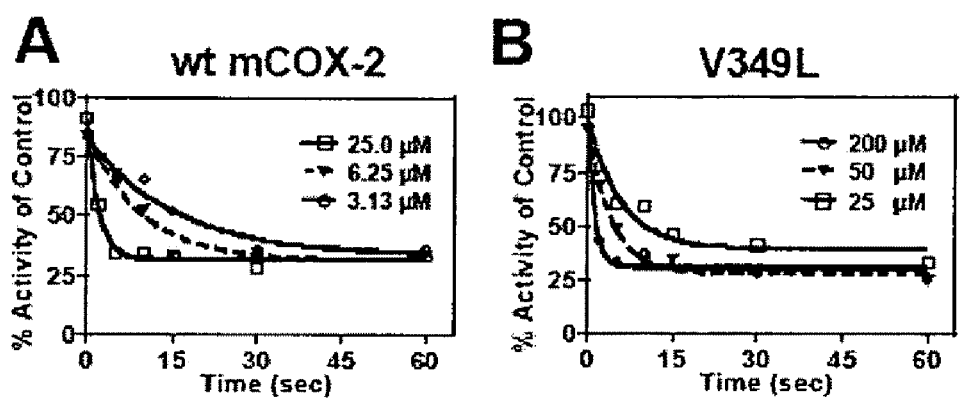
FIGS. 4A and 4B depict the kinetics of the time-dependent inhibition of COX-2 mutants by DM-INDO. Assays were performed as described in Example 7. Representative data are expressed as percent activity of the uninhibited control with non-linear regression curves.

The experiments described in Examples 7 and 8 suggested that insertion of the 2' methyl group of INDO into the hydrophobic pocket is an important contributor to the time-dependence of inhibition. To further test this, DM-INDO (FIG. 1C) was synthesized according to the scheme depicted in FIG. 6. In the time-dependent IC$_{50}$ assay, DM-INDO weakly inhibited wild type mCOX-2 and V349I but exhibited less than 20% inhibition of V349A, V349L, and wild type oCOX-1 (Table 5). The time- and concentration-dependence of inhibition of wild type enzyme and the V349L mutant exhibited a plateau of about 30% remaining activity for both enzymes, consistent with an appreciable $k_{-2}$ (FIG. 4). Importantly, V349L required nearly 10-fold higher concentrations of DM-INDO to achieve similar levels of inhibition of wild type mCOX-2. Analysis of the data for inhibition of wild type enzyme by DM-INDO yielded values for $K_I$, $k_2$, and $k_{-2}$ of 26±7 μM, 0.80±0.03 s$^{-1}$, and 0.05±0.02 s$^{-1}$, respectively. Thus, the on-rate constant ($k_2$) is 14-fold faster for DM-INDO than INDO and the off-rate constant ($k_2$) is only 14-fold slower than the on-rate.

The kinetics of V349L inhibition by DM-INDO were not amendable to analysis using equation (2), because the graph did not plateau. Linear regression analysis yielded a y-intercept value for $k_{-2}$ of 0.0025±0.0003 s$^{-1}$ (Copeland, 2000). The $K_I$ of DM-INDO for V349L must have been much greater than the equilibrium constant for the second step. Therefore, the first step in equation (1) was not saturated to allow for the time-dependent isomerization of E-1 to E-1*(Copeland, 2000).

Example 10

Reversibility of Cox Inhibition

Reversibility of COX inhibition by INDO

The reversibility of the second step in equation (1) could be directly evaluated by the amount of enzyme activity recovered after a prolonged incubation time with substrate. To test the reversibility of INDO inhibition, wild type mCOX-2 and the three Val-349 mutants were exposed to the same conditions used for the time-dependent IC$_{50}$ assay. The enzymes were pre-incubated for 20 minutes with DMSO or 10 μM INDO, prior to the addition of 50 μM AA. After addition of AA, the oxygenation reactions were allowed to proceed for varying lengths of time. As the reaction time increased, the extent of inhibition decreased if INDO binding was reversible. The time course for recovery of AA oxygenation was fit to a single exponential (FIG. 3A). As anticipated, significant reversibility of INDO inhibition was observed for the V349L mutant but not for wild type, V349A, or V349I enzymes. The value of $k_{-2}$ calculated from the activity recovery assay (0.01 s$^{-1}$) corresponded closely to the $k_{-2}$ value calculated from the time-dependent inhibition assay for INDO (0.008 s$^{-1}$; Table 6). This relationship suggested that the reversibility of the second step in the time-dependent mechanism is the principle determinant of inhibition by INDO in the presence of 50 μM AA.

Reversibility of COX Inhibition by DM-INDO

Figure 3:
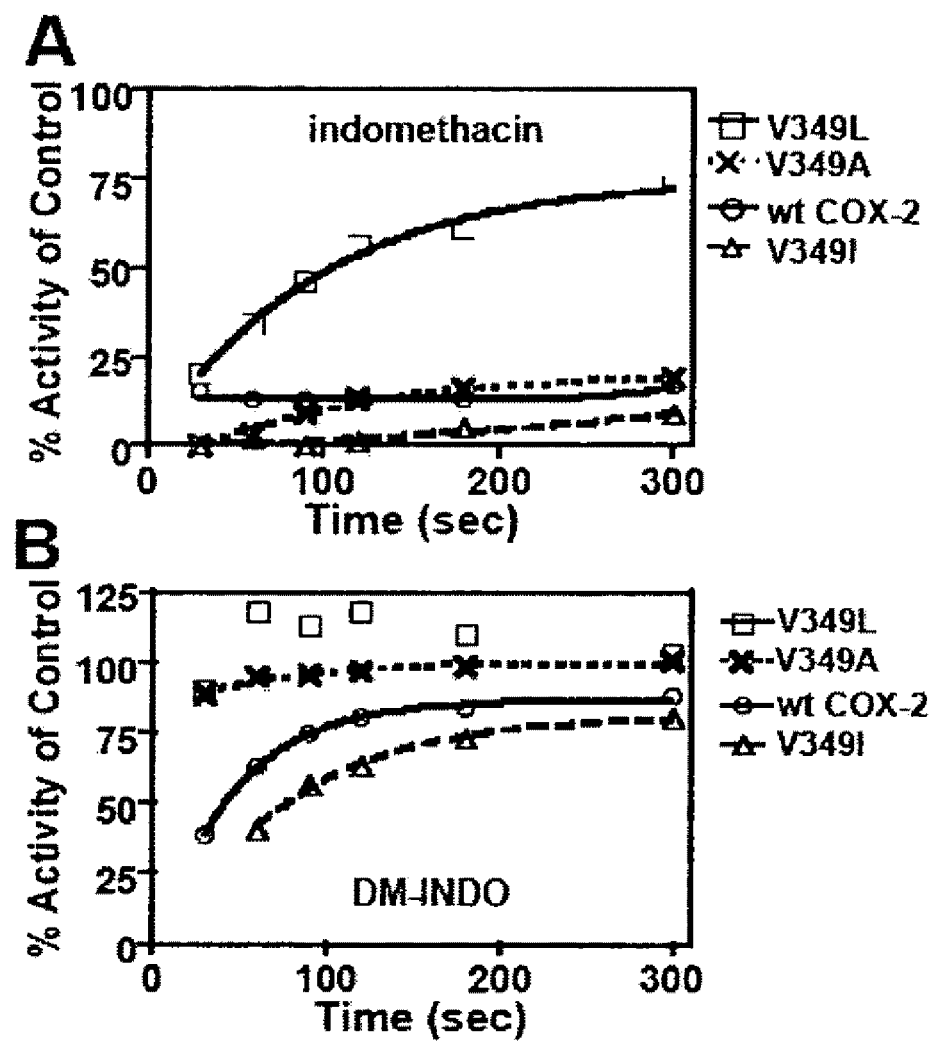
FIGS. 3A and 3B depict the effects of the three Val-349 mutations on the reversibility of COX-2 inhibition by INDO and DM-INDO. Assays were performed with 10 μM of either INDO or DM-INDO as described in Example 7. Representative data are expressed as percent activity of the uninhibited control.

The reversibility of DM-INDO inhibition was evaluated similarly to INDO using the activity recovery assay (FIG. 3). The experiments and analysis were performed as described above. DM-INDO displayed reversibility of inhibition for wild type mCOX-2 and V349I, with the $k_{-2}$ values of 0.023±0.001 s$^{-1}$ and 0.015±0.005 s$^{-1}$, respectively (FIG. 3B). The small amount of activity lost for V349A and V349L by pre-incubation with 10 μM DM-INDO, was quickly recovered upon addition of 50 μM AA (FIG. 3B).

Example 11

Steady-State Quenching of COX Intrinsic Fluorescence

Fluorescence quenching experiments with INDO and DM-INDO were performed with a Spex Fluorolog-3 spectrofluorometer (Jobin Yvon Inc., Edison, N.J., United States of America) as described in Houtzager et al., 1996. The excitation (280 nm) and emission (327 nm) bandwidths were 4 nm and 6 nm respectively. Steady-state measurements were performed at 37° C. in a 3.5 ml fluorescence cuvette with continuous stirring. All apo-proteins were diluted to 200 nM, and displayed less than 2% activity of an equivalent amount of holoenzyme. Data were collected over 240 or 360 seconds with 2-second integration times. The reversibility of quenching was analyzed in the same manner, with subsequent addition of 50 μM AA as competitor. The ligands were dissolved in DMSO before further dilution into buffer. The organic component in the buffer was below 0.4%.

Discussion of Example 11

Quenching of COX Intrinsic Fluorescence by INDO and DM-INDO

Houtzager et al. monitored inhibitor binding to COX-2 by fluorescence quenching of the apo-protein and demonstrated that the binding kinetics closely resembled the inhibition kinetics (Houtzager et al., 1996). This assay provided a method to directly monitor the binding of INDO and DM-INDO to COXs. Various concentrations of INDO and DM-INDO were added to apo-proteins and the rate of fluorescence decrease was monitored over time. After the mixture reached equilibrium, 50 μM of AA was added as competitor to monitor the reversibility of binding. The kinetic data for quenching were analyzed in the same manner as those for inhibition. For clarity, the equilibrium constant for the first step of fluorescence quenching is referred to as $K_d$, and $k_2$ and $k_{-2}$ from the second step of quenching are represented by $k'_2$ and $k'_{-2}$, respectively.

As expected, INDO bound in a time-dependent fashion and was functionally irreversible for all enzymes except V349L; the latter displayed reversible, time-dependent binding (FIG. 4). In agreement with the kinetics of inhibition, INDO quenched the V349A mutant more quickly than wild type mCOX-2. INDO bound similarly to wild type mCOX-2 and V349I. Addition of AA could only compete INDO off V349L (FIG. 5D). The kinetic parameters derived from INDO quenching correspond to those measured for INDO inhibition (Tables 6, 7).

Figure 5:
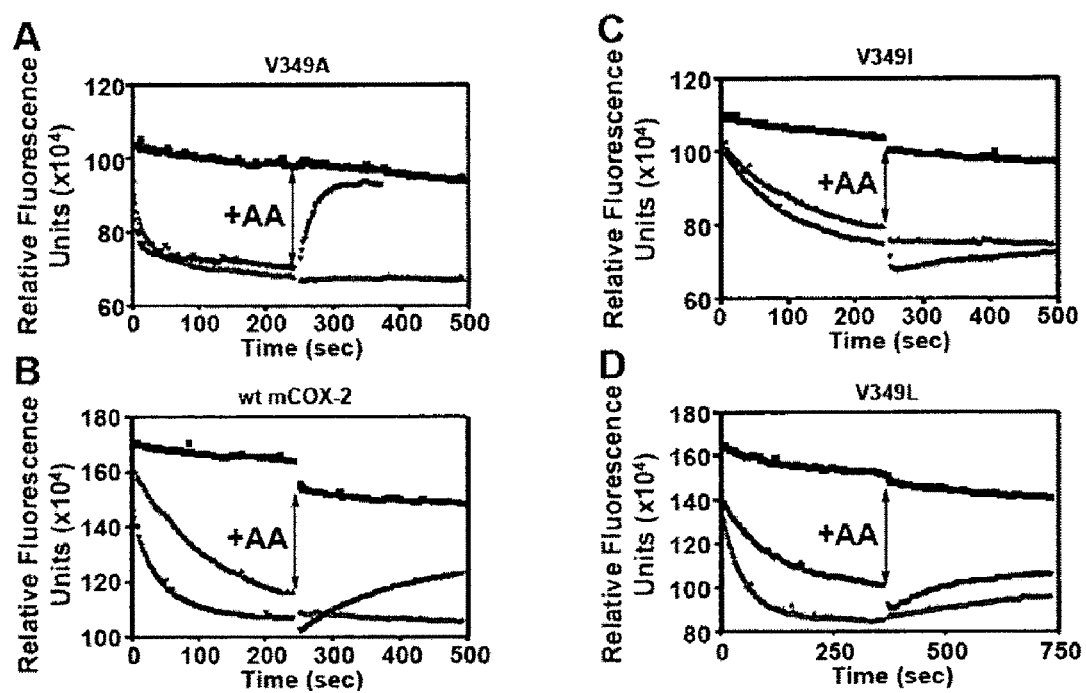
FIGS. 5A-5D depict fluorescence quenching of apo-COX-2 by INDO compared to DM-INDO, and competition by arachidonic acid (AMINO ACID). Assays were performed under conditions described in Example 9. Apo-protein at 0.2 μM was mixed with DMSO (black), INDO (red), or DM-INDO (blue) for 240 seconds (FIGS. 5A-5C) or 360 seconds (FIG. 5D), followed by the addition of 50 μM AA (arrow), and monitored for another 240 seconds (FIGS. 5A-5C) or 360 seconds (FIG. 5D). Traces are the average of 3 determinations.

DM-INDO displayed reversible, time-dependent binding with all four enzymes in the quenching assay. The V349A mutation increased the rate of binding of DM-INDO, and also increased the apparent affinity ($K_d$; Table 8). Strikingly, the value $k'_{-2}$ for V349A was the highest observed for DM-INDO, almost sevenfold higher than the $k'_2$ of wild type mCOX-2 (Table 8). The magnitude of this rate constant helps to explain why little or no inhibition was observed despite the fact that DM-INDO binds to this enzyme. DM-INDO displayed a slightly smaller off-rate constant ($k'_{-2}$) for V349I than wild type mCOX-2, which corresponded to the slight difference in the activity recovery assay observed between these two enzymes (Table 8, FIG. 3B). As with INDO, DM-INDO bound reversibly to the V349L enzyme (FIG. 5). For each enzyme and inhibitor examined, the values of $k'_{-2}$ measured by fluorescence decay and calculated from the equation (2), were equal to the $k'_{-2}$ values measured by fluorescence recovery upon incubation with AA (Tables 7 and 8). Overall, the fluorescence quenching kinetics agreed well with the kinetics of inhibition.

TABLE 7

Kinetic Parameters of Fluorescence Quenching By INDO[a]

| Enzyme | $K_d$ (µM) | $k'_2$ (s$^{-1}$) | $k'_{-2}$ (s$^{-1}$) | $k'_{-2}$[b] (s$^{-1}$) |
|---|---|---|---|---|
| V349A | 1.2 ± 0.3 | 0.12 ± 0.01 | ND[c] | ND |
| wild type mCOX-2 | 12 ± 3 | 0.062 ± 0.009 | ND | ND |
| V349I | 12 ± 2 | 0.078 ± 0.008 | ND | ND |
| V349L | 15 ± 6 | 0.065 ± 0.012 | 0.0016 ± 0.0002 | 0.0020 ± 0.0001 |

[a]Kinetic parameters ± S.E. were determined from fluorescence quenching assays
[b]Rate constant measured by fluorescence increase from competition with 50 µM AA.
[c]Values were not detectable (ND).

TABLE 8

Kinetic Parameters of Fluorescence Quenching by DM-INDO[a]

| Enzyme | $K_d$ (µM) | $k'_2$ (s$^{-1}$) | $k'_{-2}$ (s$^{-1}$) | $k'_{-2}$[b] (s$^{-1}$) |
|---|---|---|---|---|
| V349A | 1.4 ± 0.3 | 0.17 ± 0.04 | 0.045 ± 0.008 | 0.046 ± 0.002 |
| wild type mCOX-2 | 16 ± 9 | 0.16 ± 0.04 | 0.006 ± 0.002 | 0.007 ± 0.001 |
| V349I | 12 ± 5 | 0.09 ± 0.01 | 0.003 ± 0.002 | 0.005 ± 0.001 |
| V349L | 34 ± 19 | 0.05 ± 0.01 | 0.003 ± 0.002 | 0.006 ± 0.001 |

[a]Kinetic parameters ± S.E. were determined from fluorescence quenching assays.
[b]Rate constants measured by fluorescence increase from competition with 50 µM AA.

A hallmark of INDO inhibition of COX enzymes is that it appears to be functionally irreversible. Removal of the 2' methyl group from INDO significantly reduces its potency as an inhibitor of COX-2 and COX-1 and eliminates its ability to serve as a functionally irreversible inhibitor. In fact, ovine COX-1 does not appear to be inhibited at all by DM-INDO at concentrations up to 16 µM. Although the 2' methyl group appears to be a key contributor to time-dependent COX inhibition, it is not the sole determinant of binding. Previous studies have demonstrated that the carboxyl group of the indole-3-acetic acid moiety and the halogen atom of the p-chlorobenzoyl group also contribute to COX inhibition by INDO. See Rome & Lands, 1975. Esterification or amidation of the carboxyl group transforms the molecule into a weak, reversible inhibitor of COX-1 but does not eliminate time-dependent inhibition of COX-2 (Rome & Lands, 1975; Kalgutkar et al., 2000a). However, the mode of binding of INDO esters and amides appears to be different from that of the parent acid. Inhibition of COX-2 by INDO is eliminated by mutations of Arg-120 or Tyr-355 whereas inhibition by INDO esters and amides is eliminated by mutations of Tyr-355 or Glu-524 but not Arg-120 (Kalgutkar et al., 2000a). The absence of a strong ionic interaction can account for the slow reversibility of inhibition observed for certain INDO amides containing bulky substituents in the amide functional group, and for the inability of 2-des-methyl derivatives of INDO esters and amides to exhibit any inhibition of COX-2 (Kalgutkar et al., 2000b; Timofeevski et al., 2002).

The presently disclosed subject matter demonstrates the importance of Val-349 in the interaction of COX enzymes with substrates and inhibitors. Previous studies have revealed that mutations of Val-349 affect the affinities of COX-1 or COX-2 for substrates, the rates of substrate oxygenation, and the regiochemistry and stereochemistry of product formation (Thuresson et al., 2001; Schneider et al, 2002). The decreases in specific activity observed with the various mutants in the presently disclosed subject matter are consistent with previous reports. The reduced activities of the mutants necessitated the adjustment of protein concentration in the inhibition assays to amounts that yielded similar rates of substrate turnover. However, a constant protein concentration was used in the fluorescence quenching assays because differences in specific activities were irrelevant due to the use of apo-enzyme. Despite the differences in protein concentrations and other aspects in the design of the inhibition and fluorescence quenching assays, the values determined for the kinetic parameters of INDO and DM-INDO binding and inhibition were remarkably consistent with the exception of the rate-constants for dissociation where differences of less than sevenfold were observed.

Pharmacological activities of INDO such as its anti-inflammatory activity, analgesic activity, and gastrointestinal toxicity are believed to derive from the ability of INDO to inhibit COX-2 and COX-1. However, INDO has been reported to exert additional biochemical activities in cellular systems and it has been proposed that these non-COX activities might contribute to its in vivo pharmacology (Weggen et al., 2001). The presently disclosed observation that a subtle chemical modification—modifying the 2' methyl group to a moiety selected from the group consisting of hydrogen, halo, and $C_2$ to $C_6$ alkyl or branched alkyl—greatly reduces COX inhibitory activity provides a strategy for optimizing pharmacological effects at COX-independent targets while minimizing undesirable side effects due to COX inhibition.

Example 12

Inhibition of COX Enzymes by 2-Des-Methyl Derivatives

The 2-Des-methyl analog of INDO (DM-INDO) was synthesized as discussed in Example 4, and tested against wild-type COX-1 and COX-2 as well as the Val-349 mutants as described in Example 7. DM-INDO bound to all enzymes tested, but only displayed inhibitory potency against wild type mCOX-2 and the V349I enzyme. Without the 2' methyl group anchoring DM-INDO in the active site, the compound was readily competed off of the enzyme by arachidonic acid (AA). The kinetics of inhibition were comparable to the kinetics of binding as evaluated by fluorescence quenching. These results implicate the importance of the contacts between the 2' methyl group of INDO and the "methyl-binding pocket", in its time-dependent binding and inhibition of COXs.

Example 13

Cell Viability Assay

Figure 8:
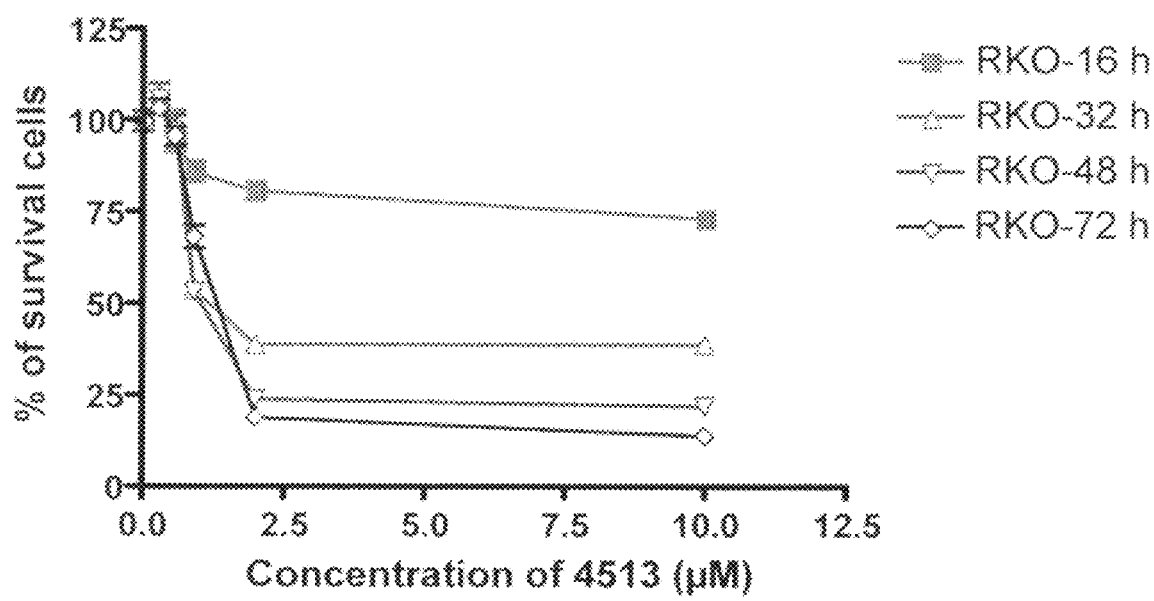
FIG. 8 depicts the results of cell viability assays of RKO cells exposed to various concentrations of N-Benzyl-2-[6-fluoro-3-(4-methylsulfanyl-benzylidene)-3H-inden-1-yl]-acetamide (Compound J).

RKO and HCT-116 cells (human colorectal cancer cell lines) were cultured in microtiter plates (tissue culture grade, 96-well flat) in a final volume of 100 µl culture medium containing $5-8\times10^4$ cells and the final concentrations of chemicals (1-500 µM). Cells were incubated in a humidified atmosphere for 8-24 hours. To the cultures, 10 µl of cell proliferation reagent, WST-1 (Roche Applied Science, Indianapolis, Ind., United States of America) was added, and reincubated for 1-2 hours. The absorbance of the samples was determined using a microtiter plate reader at a wavelength of 405-450 nm against background control. Reference wavelength was 620 nm. The tetrazolium salt, WST-1 (4-[3-(4-Iodophenyl)-2-(4-nitrophenyl)-2H-5-tetrazolio]-1,3-benzene disulfonate) was metabolized to formazan by the "succinate-tetrazolium reductase" system, which exists in mitochondria and is active only in viable cells. Thus, the formation of formazan (dark yellow color) is proportional to the viable cell numbers. The results of this experiment are presented in FIG. 8.

Example 14

Determination of $ED_{50}$ Values for Derivatives

The cell viability assay described in Example 13 was employed with each derivative listed in Table 9. The generated data points were used to calculate $ED_{50}$ values by creating a sigmoidal dose-response curve using non-linear regression. $ED_{50}$ valued were calculated using the statistical analysis program PRISM® (GraphPad Software, Inc., San Diego, Calif., United States of America).

The $ED_{50}$ values for the derivatives are presented in Table 9. $ED_{50}$ values were also calculated for indomethacin and sulindac sulfide using the above referenced cell viability assay. Sulindac sulfide had an $ED_{50}$ value of 98.2±1.4 µM in RKO cells, and 109.4±10.0 µM in HCT-116 cells. Indomethacin had an $ED_{50}$ value of 162.2±11.0 µM in RKO cells, and 448.7±97.6 µM in HCT-116 cells.

TABLE 9

Activities of 2-Des-methyl Derivatives in Cell Viability Assays

| Compound | $R^{11}$ | $R^{12}$ | $ED_{50}$ (µM) RKO | $ED_{50}$ (µM) HCT-116 |
|---|---|---|---|---|
| 2 | HN–phenyl | S(=O)-phenyl | >3 | >3 |
| 3 | HN–CH₂–phenyl | S(=O)-phenyl | 1.1 ± 0.7 | 3.9 ± 0.9 |
| 4 | HN–CH₂CH₂–phenyl | S(=O)-phenyl | >3 | >3 |
| 5 | HN–CH₂CH₂CH₂–phenyl | S(=O)-phenyl | >3 | >3 |

TABLE 9-continued
| | | | | |
|---|---|---|---|---|
| 6 | 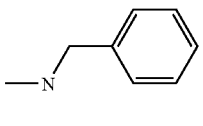 | 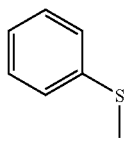 | >3 | >3 |
| 7 | 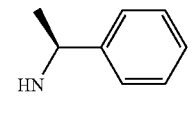 | 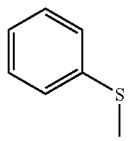 | >3 | >3 |
| 8 | 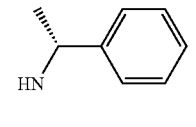 | 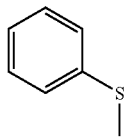 | >3 | >3 |
| 9 | 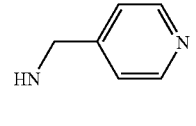 | 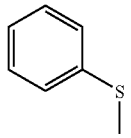 | >3 | >3 |
| 10 | 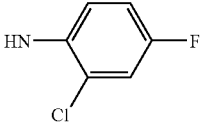 | 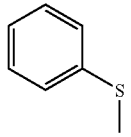 | >3 | >3 |
| 11 | 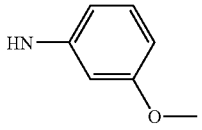 | 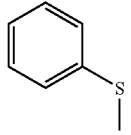 | >3 | >3 |
| 12 | 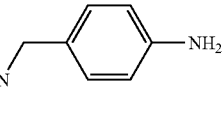 | 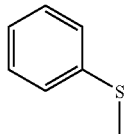 | 2.30 ± 0.03 | >3 |
| 13 | 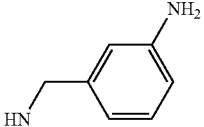 | 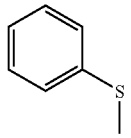 | 0.99 ± 0.03 | 2.08 ± 0.08 |
| 14 | 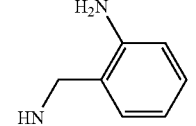 | 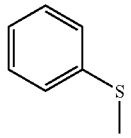 | >3 | >3 |
| 15 | 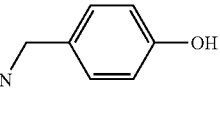 | 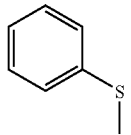 | 0.10 ± 0.04 | 1.2 ± 0.2 |
| 16 | 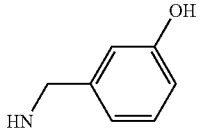 | 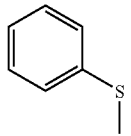 | 0.83 ± 0.06 | 1.47 ± 0.03 |

TABLE 9-continued
| | | | | |
|---|---|---|---|---|
| 17 | 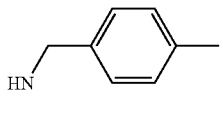 | 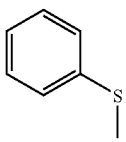 | 0.73 ± 0.06 | 1.2 ± 0.1 |
| 18 | 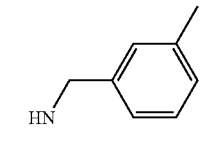 | 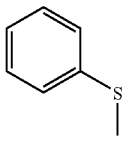 | >3 | >3 |
| 19 | 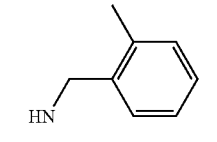 | 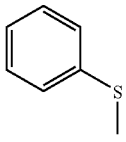 | >3 | >3 |
| 20 | 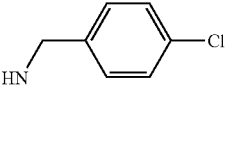 | 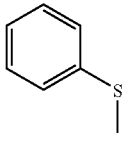 | 0.63 ± 0.07 | 0.8 ± 0.1 |
| 21 | 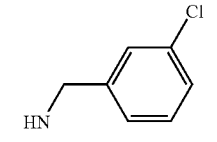 | 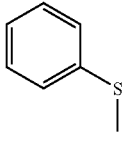 | >3 | >3 |
| 22 | 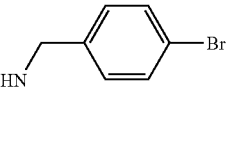 | 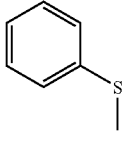 | 0.67 ± 0.07 | 1.3 ± 0.2 |
| 23 | 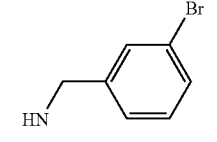 | 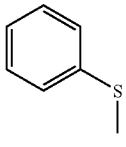 | >3 | >3 |
| 24 | 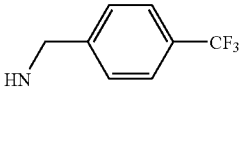 | 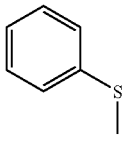 | >3 | >3 |
| 25 | 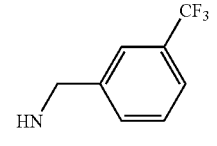 | 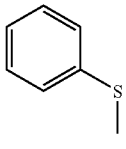 | >3 | >3 |
| 26 | 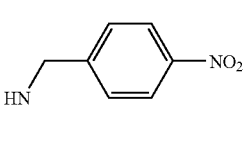 | 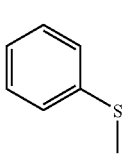 | 0.54 ± 0.07 | 2.1 ± 0.7 |

TABLE 9-continued

| | | | RKO | HCT-116 |
|---|---|---|---|---|
| 27 | 3-nitrobenzylamine (HN-CH2-C6H4-NO2) | PhSMe (thioanisole) | >3 | >3 |
| 28 | 2-nitrobenzylamine | PhSMe | >3 | >3 |
| 29 | 4-(2-B-acetamido)benzylamine | PhCH2-N3 (benzyl azide) | >3 | >3 |
| 30 | 4-benzoylbenzylamine | PhSMe | 0.04 ± 0.02 | 0.18 ± 0.04 |
| 31 | 4-(2-phenyloxiran-2-yl)benzylamine | PhCH2-N3 | >3 | >3 |

<br>

Structure: 5-fluoro-1-(=CHR¹²)-indene-3-yl-CH2-C(=O)-NH-CH2-Ph

| | | ED$_{50}$ (µm) | |
|---|---|---|---|
| Compound | R¹² | RKO | HCT-116 |
| 32 | PhS(=O)Me (methyl phenyl sulfoxide) | 2.4 ± 0.2 | 6 ± 1 |
| 33 | PhSO$_2$Me (methyl phenyl sulfone) | 0.8 ± 0.1 | 1.2 ± 0.3 |
| 34 | Ph | 5.4 ± 0.5 | n.d. |
| 35 | 4-methoxyphenyl | 0.7 ± 0.1 | 1.0 ± 0.8 |
| 36 | 4-carboxyphenyl (—COOH) | 6.4 ± 0.6 | n.d. |

TABLE 9-continued

| | | | |
|---|---|---|---|
| 37 | phenyl-Br | >10 | n.d. |
| 38 | cyclohexyl | 6.7 ± 0.1 | n.d. | n.d.: not determined

Example 15

Caspase-3 Colorimetric Assay

Figure 9:
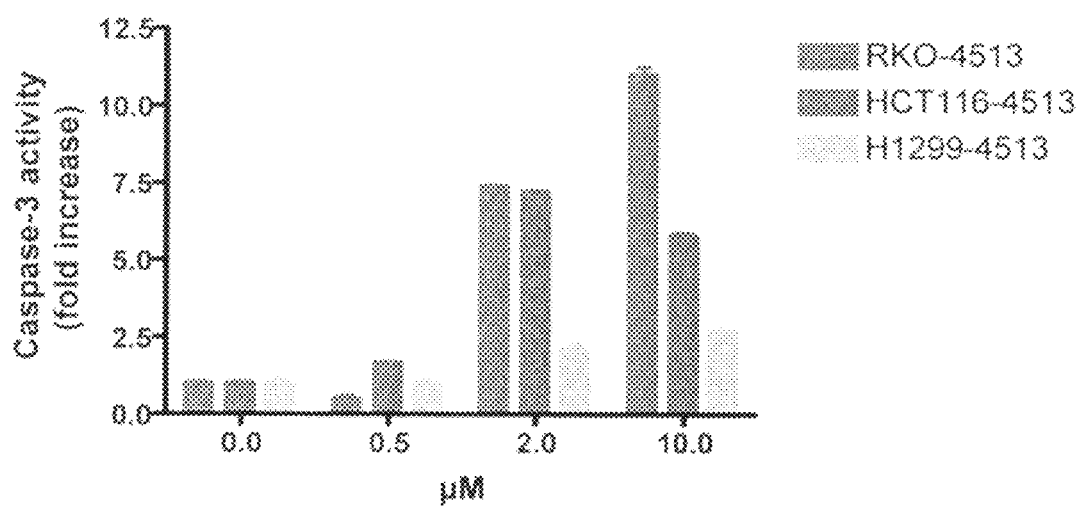
FIG. 9 depicts the results of increased caspase-3 activity in three different cell lines exposed to various concentrations of N-Benzyl-2-[6-fluoro-3-(4-methylsulfanyl-benzylidene)-3H-inden-1-yl]-acetamide (Compound J).

RKO, HCT-116 (another human colorectal cancer cell line), and H1299 (a human non-small cell cancer line) cells that had been treated with test compounds for various times were washed twice with ice-cold PBS and lysed in a lysis buffer (BioVision) on ice for 10 minutes, followed by centrifugation at 15,000×g for 10 minutes. Caspase-3 activity, which is a measure if the initiation of apoptotic cell death, was determined in the supernatant by a colorimeric assay kit (BioVision Inc., Palo Alto, Calif., United States of America) using the p-nitroanilide-labeled peptide, DEVD-pNA, as substrate. Caspase-3 activity was monitored by the release of p-nitroanilide from the substrate at 405 nm. The fold increase in caspase-3 activity is shown in FIG. 9, and was calculated by comparing the absorbance of p-nitroanilide from vehicle treated controls and those treated with sulindac sulfide and its analogs.

Example 16

Preparation of Protein Lysates and Western Blotting Analysis

Cells that had been treated with test compounds for various times were washed twice with ice-cold phosphate buffered saline (PBS) and lysed in kinase lysis buffer [50 mM Tris buffer (pH 7.5) 150 mM NaCl, 0.1% Triton X-100, 0.1% Nonidet P-40, 4 mM ethylenediamine tetraacetic acid (EDTA), 50 mM NaF, 0.1 mM sodium orthovanadate, 1 mM dithiothreitol (DTT) and protease inhibitors: antipain, leupeptin, pepstatin A, and chymostatin (5 µg/mL), phenylmethylsulfonyl fluoride (50 µg/mL) and 4-(2-aminoethyl)-benzenesulfonylfluoride (100 µg/mL)] for 30 minutes at 4° C. Cell lysates were cleared by centrifugation at 15,000 g for 15 minutes, and the resulting supernatant was collected. Cellular protein (30-50 µg) was mixed with an equal volume of 2× Laemmli sample buffer [125 mM Tris (pH 6.8), 10% β-mercaptoethanol, 20% glycerol, 4% sodium dodecyl sulfate (SDS), and 0.05% bromophenol blue] and boiled for 5 minutes. The proteins were resolved by sodium dodecyl sulfate-polyacrylamide gel electrophoresis (SDS-PAGE) and electrophoretically transferred onto polyvinylidene difluoride membranes (Millipore Corp., Bedford, Mass., United States of America). The membranes were blocked with 5% non-fat milk in Tris-buffered saline (50 mM Tris pH 7.5, 150 mM NaCl) containing 0.1% Tween 20, then incubated with anti-poly(ADP-ribose) polymerase (PharMingen, San Diego, Calif., United States of America) for 1-2 hours. The primary antibody was then stained with either donkey anti-rabbit or goat anti-mouse horseradish peroxidase-conjugate secondary antibodies. Enhanced chemiluminescence was performed (ECL Western blotting detection system: Amersham Biosciences, Piscataway, N.J., United States of America) and protein bands detected by autoradiography. The detection of a band corresponding to cleaved poly(ADP-ribose) polymerase indicated the initiation of apoptotic cell death.

Example 17

PPARγ Reporter Assays

Human embryonic kidney cells (HEK293 cells) were purchased from American Type Culture Collection (ATCC) and maintained in Dulbecco's modified Eagle's medium (DMEM) with GIBCO™ GLUTAMAX™ (Invitrogen Corp., Carlsbad, Calif., United States of America) and 10% heat-inactivated FBS (Atlas Biological, Fort Collins, Colo., United States of America) or 10% charcoal-stripped FBS (HyClone, Logan, Utah, United States of America) in a 5% $CO_2$ constant humidity 37° C. incubator. $9 \times 10^5$ HEK293 cells were plated in DMEM supplemented with 10% charcoal-stripped FBS. 18-24 hours after plating, cells were transfected with a control *Renilla* luciferase expressing plasmid (0.2 µg pCMV-*renilla* luciferase from Promega Corp., Madison, Wis., United States of America), 0.4 µg PPARγ-GAL4, and 0.4 µg UAS-tk-luc using a lipid ratio of 8 µL Effectene Transfection Reagent (Qiagen Inc., Valencia, Calif., United States of America) per 1 µg DNA in 3 mL of DMEM+10% charcoal-stripped FBS. Cells remained in the transfection mixture overnight until the transfection media was replaced with DMEM+10% charcoal-stripped serum containing ligands of interest or vehicle (0.1% DMSO)

Figure 10:
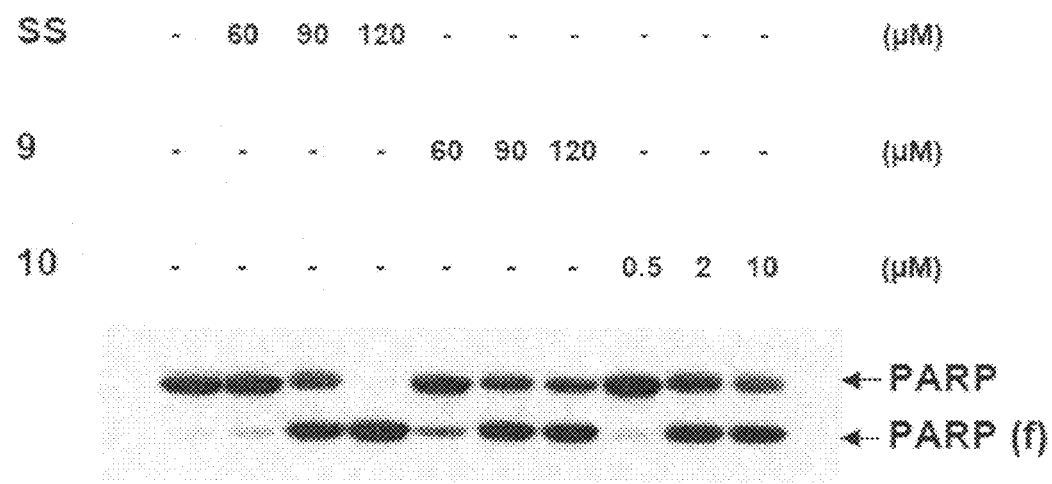
FIG. 10 depicts the Western blot analyses of results of PPARγ reporter assays of HEK293 cells exposed to various concentrations of sulindac sulfide (SS), eindenic acid sulfide (Compound I), or N-Benzyl-2-[6-fluoro-3-(4-methylsulfanyl-benzylidene)-3H-inden-1-yl]-acetamide (Compound J).

Transfected HEK293 cells were treated with various concentrations of eindenic acid sulfide or the N-benzyl amide derivative of eindenic acid sulfide, N-Benzyl-2-[6-fluoro-3-(4-methylsulfanyl-benzylidene)-3H-inden-1-yl]-acetamide, dissolved in DMSO or vehicle alone (0.1% DMSO) for 4 hours. Cells were lysed in Passive Lysis Buffer (Promega Corp.) and lysates were assayed for firefly luciferase and *Renilla* luciferase activity using the DUAL-LUCIFERASE® Reporter (DLR™) Assay system (Promega Corp., Catalog #E1910) according to the manufacturer's instructions. The results of this experiment are presented in FIG. 10.

Discussion of Example 17

2-Des-methylindomethacin and eindenic acid sulfide and a series of structural analogs were tested for their ability to induce apoptosis of cultured cancer cells and for their ability to activate PPARγ-mediated transcription in transfected cells in culture. Both compounds were demonstrated to be as active or more active than the parent drug. In fact, eindenic acid sulfide is considerably more active than sulindac sulfide in both assays. Similar results were obtained with analogs of eindenic acid sulfide. While the co-inventors do not wish to be limited to any particular theory of operation, the enhanced biological activity of 2-Des-methyl analogs might be due to the alteration in conformation that results from deletion of the 2' methyl group.

Example 18

Toxicity of 2-Des-methylindomethacin In Vivo

The toxicity of indomethacin and 2-Des-methylindomethacin were compared in C57/BL6 mice, which are very sensitive to gastrointestinal toxicity by indomethacin. Daily injections of a series of concentrations of indomethacin and 2-Des-methylindomethacin demonstrated that 2-Des-methylindomethacin is at least 25-fold less toxic than indomethacin, verifying that much higher concentrations of 2-Des-methyl analogs can be administered. Thus, 2-Des-methyl analogs of indomethacin and sulindac sulfide, as well as any prodrug forms (e.g., eindenic acid sulfoxide), appear to be attractive candidates for drugs targeting a range of diseases.

REFERENCES

The references listed below as well as all references cited in the specification are incorporated herein by reference to the extent that they supplement, explain, provide a background for, or teach methodology, techniques, and/or compositions employed herein.

Allison M C, Howatson A G, Torrance C J, Lee F D & Russell R I (1992) Gastrointestinal Damage Associated with the Use of Nonsteroidal Antiinflammatory Drugs. *N. Engl. J. Med.* 327:749-754.

Bowden D W, Sale M, Howard T D, Qadri A, Spray B J, Rothschild C B, Akots G, Rich S S & Freedman B I (1997) Linkage of genetic markers on human chromosomes 20 and 12 to NIDDM in Caucasian sib pairs with a history of diabetic nephropathy. *Diabetes* 46:882-86.

Celi F S & Shuldiner A R (2002) The role of peroxisome proliferator-activated receptor gamma in diabetes and obesity. *Curr Diab Rep* 2:179-85.

Copeland R A (2000) *Enzymes: A Practical Introduction to Structure, Mechanism, and Data Analysis*, Wiley-VCH, New York, N.Y., United States of America.

DeWitt D L & Smith W L (1988) Primary Structure of Prostaglandin G/H Synthase from Sheep Vesicular Gland Determined from the Complementary DNA Sequence. *Proc Natl Acad Sci USA* 85:1412-1416.

Doege H, Schurmann A, Bahrenberg G, Brauers A & Joost H G (2000) GLUT8, a novel member of the sugar transport facilitator family with glucose transport activity. *J Biol Chem* 275:16275-80.

Edelman S (1998) Representation is representation of similarities. *Adv Internal Med* 43:449-500.

Ghosh S, Watanabe R M, Hauser E R, Valle T, Magnuson V L, Erdos M R, Langefeld C D, Balow J Jr, Ally D S, Kohtamaki K, et al. (1999) Type 2 diabetes: evidence for linkage on chromosome 20 in 716 Finnish affected sib pairs. *Proc Natl Acad Sci USA* 96:2198-2203.

Hanis C L, Boerwinkle E, Chakraborty R, Ellsworth D L, Concannon P, Stirling B, Morrison V A, Wapelhorst B, Spielman R S, Gogolin-Ewens K J, et al. (1996) A genome-wide search for human non-insulin-dependent (type 2) diabetes genes reveals a major susceptibility locus on chromosome 2. *Nat Genet.* 13:161-66.

Hansen T, Andersen C B, Echwald S M, Urhammer S A, Clausen J O, Vestergaard H, Owens D, Hansen L & Pedersen O (1997) Identification of a common amino acid polymorphism in the p85 regulatory subunit of phosphatidylinositol 3-kinase. *Diabetes* 46:494-501.

Hla T & Neilson K (1992) Human cyclooxygenase-2 cDNA. *Proc Natl Acad Sci USA* 89:7384-7388.

Ibberson M, Uldry M & Thorens B (2000) GLUTX1, a novel mammalian glucose transporter expressed in the central nervous system and insulin-sensitive tissues. *J Biol Chem* 275:4607-12.

Ji L, Malecki M, Warram J H, Yang Y, Rich S S & Krolewski A S (1997) New susceptibility locus for NIDDM is localized to human chromosome 20q. *Diabetes* 46:876-81.

Kalgutkar A S, Crews B C, Rowlinson S W, Marnett A B, Kozak K R, Remmel R P & Marnett L J (2000a) Biochemically based design of cyclooxygenase-2 (COX-2) inhibitors: facile conversion of nonsteroidal antiinflammatory drugs to potent and highly selective COX-2 inhibitors. *Proc Natl Acad Sci USA* 97, 925-30.

Kalgutkar A S, Marnett A B, Crews B C, Remmel R P & Marnett L J (2000b) Ester and amide derivatives of the nonsteroidal antiinflammatory drug, indomethacin, as selective cyclooxygenase-2 inhibitors. *J Med Chem* 43, 2860-70.

Kersten S, Desvergne B & Wahli W (2000) Roles of PPARs in health and disease. Nature 405:421-4.

Kujubu D A, Fletcher B S, Varnum B C, Lim R W & Herschman H R (1991) TIS10, A Phorbol Ester Tumor Promoter Inducible mRNA from Swiss 3T3 Cells, Encodes a Novel Prostaglandin Synthase/Cyclooxygenase Homologue. *J Biol Chem* 266:12866-12872.

Kulmacz R J & Lands W E (1985) Stoichiometry and kinetics of the interaction of prostaglandin H synthase with anti-inflammatory agents. *J Biol Chem* 260:12572-8.

Kurumbail R G, Stevens A M, Gierse J K, McDonald J J, Stegeman R A, Pak J Y, Gildehaus D, Miyashiro J M, Penning T D, Seibert K, Isakson P C & Stallings W C (1996) Structural basis for selective inhibition of cyclooxygenase-2 by anti-inflammatory agents. *Nature* 384:644-648.

Kusari J, Verma U S, Buse J B, Henry R R & Olefsky J M (1991) Analysis of the gene sequences of the insulin receptor and the insulin-sensitive glucose transporter (GLUT-4) in subjects with common-type non-insulin-dependent diabetes mellitus. *J Clin Invest* 88:1323-30.

Lee S H, Soyoola E, Chanmugam P, Hart S, Sun W, Zhong H, Liou S, Simmons D & Hwang D (1992) Selective Expression of Mitogen-Inducible Cyclooxygenase in Macrophages Stimulated with Lipopolysaccharide. *J Biol Chem* 267:25934-25938.

Mahtani M M, Widen E, Lehto M, Thomas J, McCarthy M, Brayer J, Bryant B, Chan G, Daly M, Forsblom C, Kanninen T, Kirby A, Kruglyak L, Munnelly K, Parkkonen M, Reeve-Daly M P, Weaver A, Brettin T, Duyk G, Lander E S, Groop L C (1996) Mapping of a gene for type 2 diabetes associated with an insulin secretion defect by a genome scan in Finnish families. *Nat Genet.* 14:90-4.

Markey C M, Alward A, Weller P E & Marnett L J (1987) Quantitative studies of hydroperoxide reduction by prostaglandin H synthase. Reducing substrate specificity and the relationship of peroxidase to cyclooxygenase activities. *J Biol Chem* 262, 6266-79.

Meade E A, Smith W L & DeWitt D L (1993) Differential inhibition of prostaglandin endoperoxide synthase (cyclooxygenase) isozymes by aspirin and other non-steroidal anti-inflammatory drugs. *J Biol Chem* 268:6610-6614.

O'Sullivan M G, Huggins E M Jr. & McCall C E (1993) Lipopolysaccharide-Induced Expression of Prostaglandin

What is claimed is:

1. A compound of the following formula:

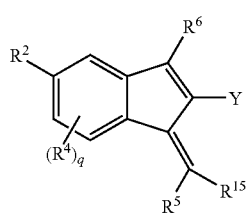

Formula Ib wherein:

$R^2$ is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;

$R^4$ is selected from the group consisting of hydrogen; halo; $CF_3$; $C_1$ to $C_6$ alkyl, branched alkyl, or substituted alkyl; $C_1$ to $C_6$ alkoxy, branched alkoxy, or substituted alkoxy; aryl; substituted aryl; benzyloxy; $SCH_3$; $SOCH_3$; $SO_2CH_3$; and $SO_2NH_2$;

$R^5$ is selected from the group consisting of hydrogen, $C_1$ to $C_6$ alkyl, $C_1$ to $C_6$ branched alkyl, and $C_1$ to $C_6$ substituted alkyl;

$R^6$ is selected from the group consisting of $C_1$ to $C_6$ alkylcarboxylic acid, branched alkylcarboxylic acid, and substituted alkylcarboxylic acid $R^{15}$ is selected from the group consisting of cyclohexyl; an unsubstituted, single substituted, or multiply substituted aryl; and an unsubstituted, single substituted, or multiply substituted heteroaryl;

Y is selected from the group consisting of hydrogen and halo; and q is 0, 1, 2, 3, or 4.

2. The compound of claim 1, wherein $R^{15}$ is an unsubstituted, single substituted, or multiply substituted aryl or an unsubstituted, single substituted, or multiply substituted heteroaryl with multiple aromatic rings that are fused together or covalently linked.

3. The compound of claim 2, the multiple aromatic rings are covalently linked by a moiety selected from the group consisting of an alkylene moiety, a carbonyl, oxygen, diphenylether, and nitrogen.

4. The compound of claim 2, wherein the multiple aromatic rings are selected from the group consisting of naphthyl, biphenyl, diphenylether, diphenylamine, and benzophenone.

5. The compound of claim 1, wherein $R^2$ is selected from the group consisting of halo, $C_1$ to $C_6$ alkyl or branched alkyl, $SCH_3$, $SOCH_3$, $SO_2CH_3$, and $SO_2NH_2$.

6. The compound of claim 5, wherein $R^2$ is F.

7. The compound of claim 1, wherein $R^{15}$ is in the E orientation with respect to the indene ring.

8. The compound of claim 1, wherein $R^{15}$ is one of the following formulas:

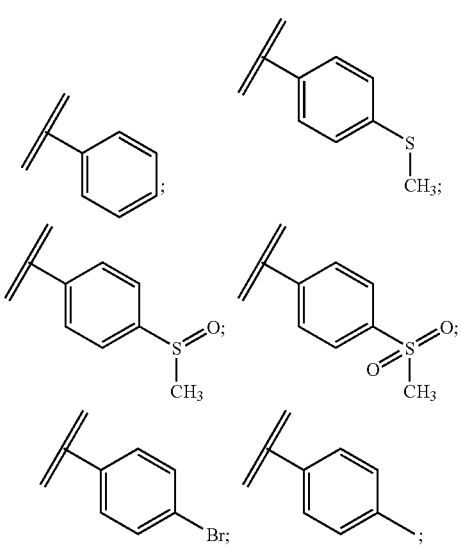

-continued
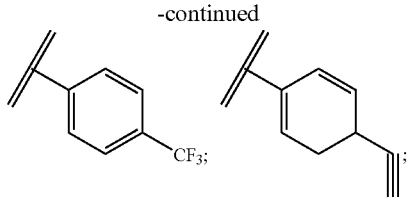
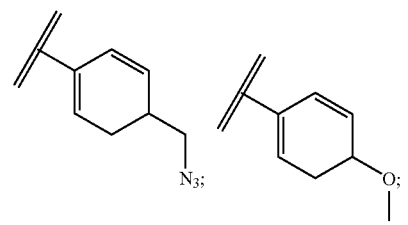
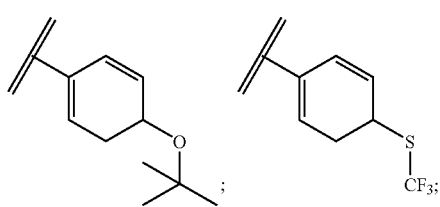
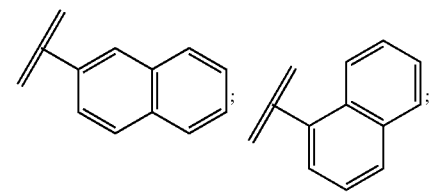
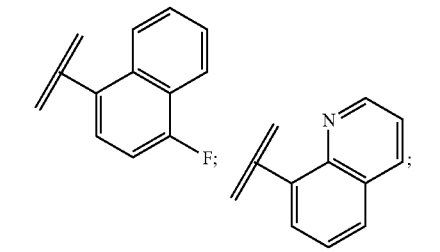
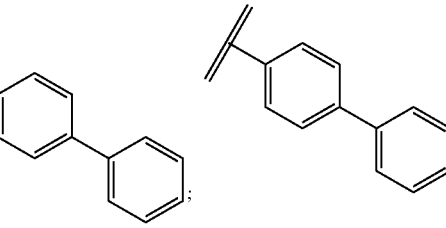
and
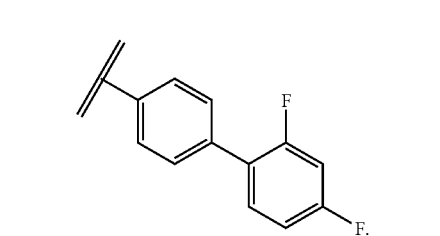
9. The compound of claim 1, wherein the compound has one of the following formulas:
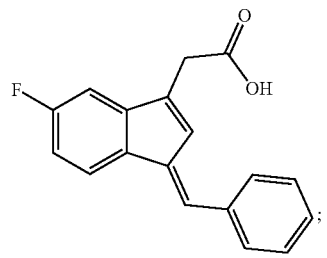
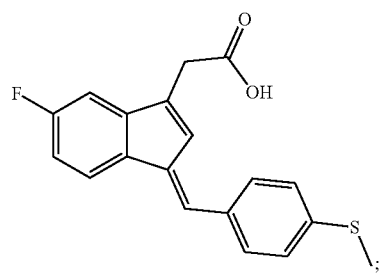
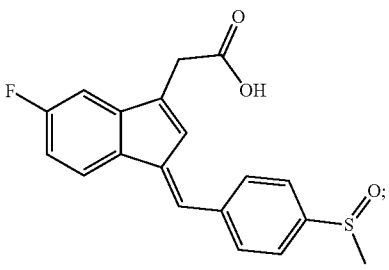
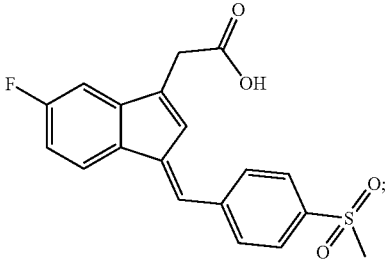
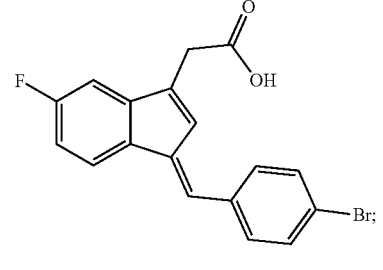
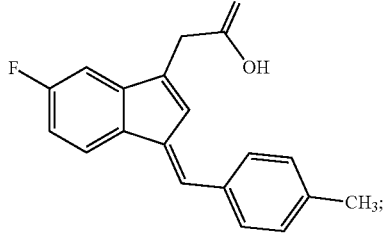

107
-continued
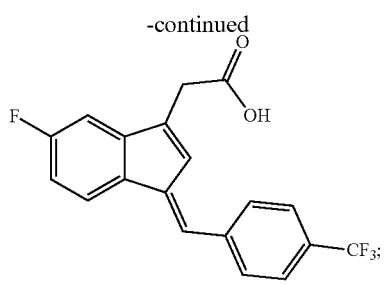
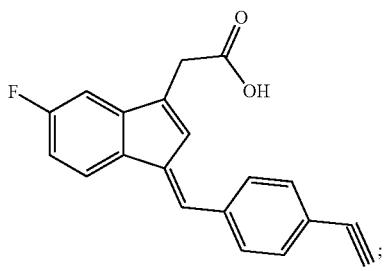
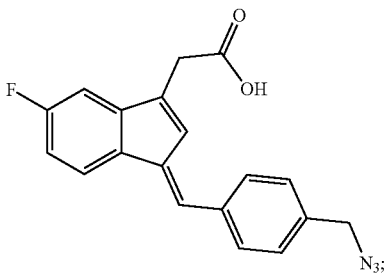
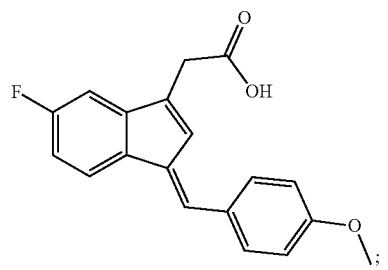
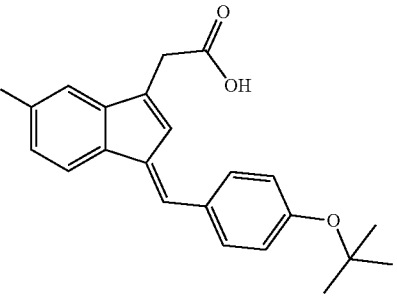
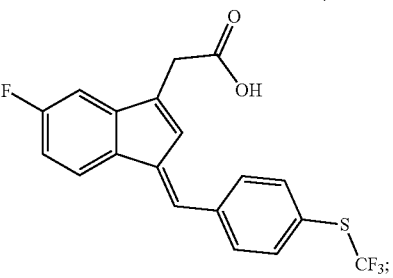
108
-continued
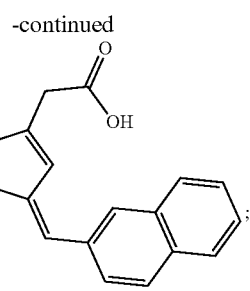
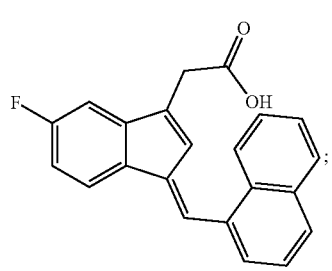
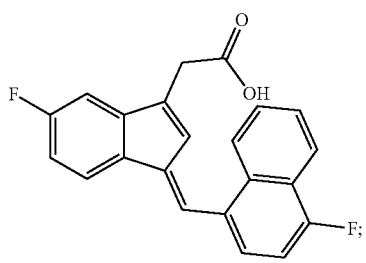
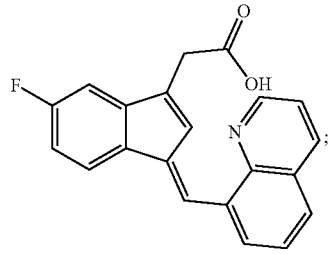
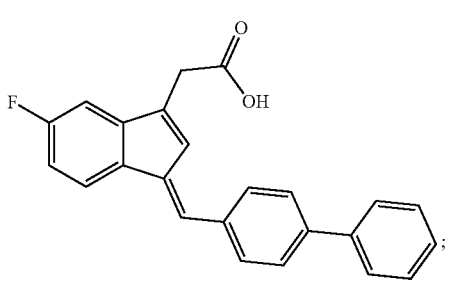
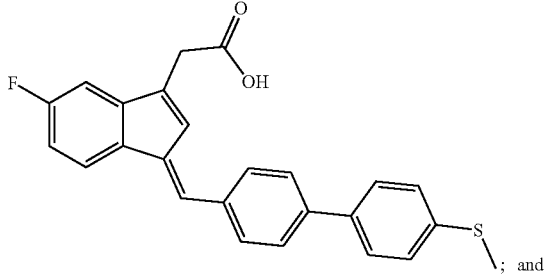

-continued

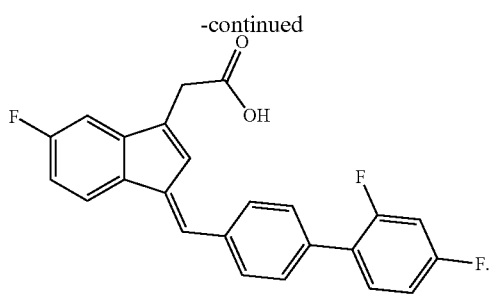

10. A compound of the following formula:

Formula Ib

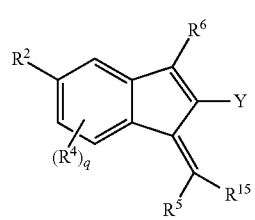

wherein:

R² is selected from the group consisting of hydrogen, halo, $CF_3$; $SCH_3$; $SOCH_3$; $SO_2CH_3$; $SO_2NH_2$; $CONH_2$; $C_1$ to $C_6$ alkyl, branched alkyl, or substituted alkyl; $C_1$ to $C_6$ alkoxy, branched alkoxy, or substituted alkoxy; benzyloxy; $C_1$ to $C_6$ alkylcarboxylic acid, branched alkylcarboxylic acid, or substituted alkylcarboxylic acid; and $CH_2N_3$;

R⁴ is selected from the group consisting of hydrogen; halo; $CF_3$; $C_1$ to $C_6$ alkyl, branched alkyl, or substituted alkyl; $C_1$ to $C_6$ alkoxy, branched alkoxy, or substituted alkoxy; aryl; substituted aryl; benzyloxy; $SCH_3$; $SOCH_3$; $SO_2CH_3$; and $SO_2NH_2$;

R⁵ is selected from the group consisting of hydrogen, $C_1$ to $C_6$ alkyl, $C_1$ to $C_6$ branched alkyl, and $C_1$ to $C_6$ substituted alkyl;

R⁶ is selected from the group consisting of $C_1$ to $C_6$ alkylcarboxylic acid, branched alkylcarboxylic acid, and substituted alkylcarboxylic acid;

Y is selected from the group consisting of hydrogen and halo;

q is 0, 1, 2, 3, or 4; and

R¹⁵ is one of the following formulas:

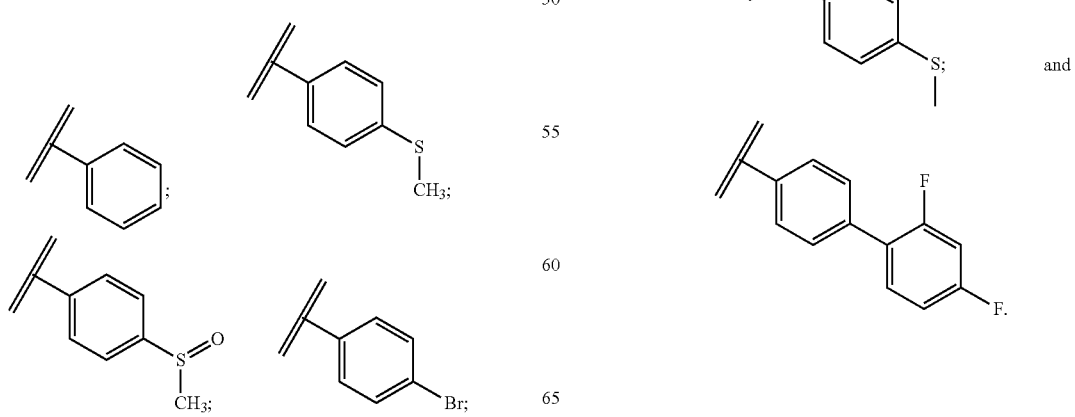

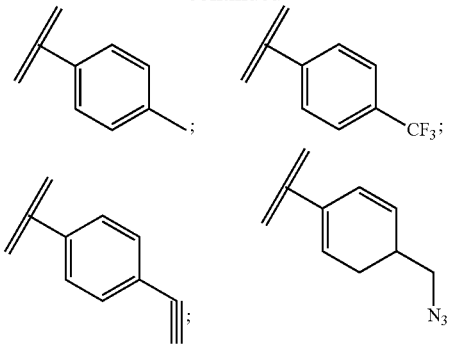

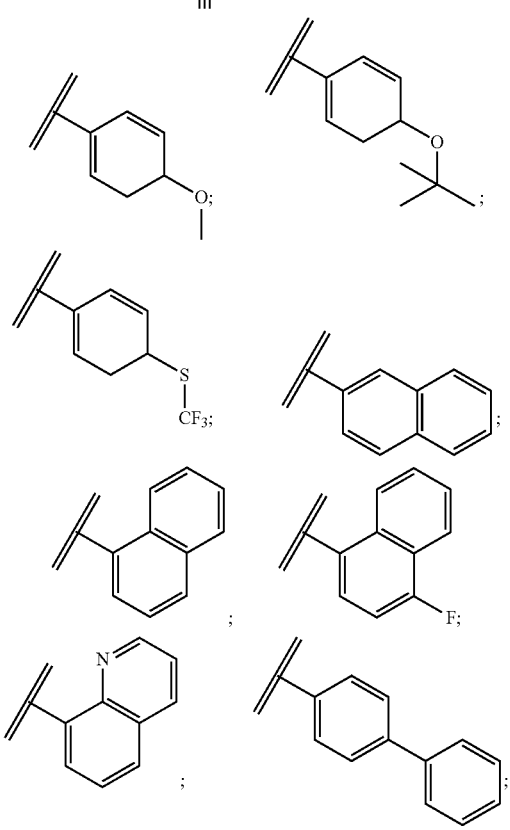

* * * * *